United States Patent
Saraf et al.

(10) Patent No.: US 6,915,621 B2
(45) Date of Patent: Jul. 12, 2005

(54) METHOD AND APPARATUS FOR WRAPPING PADS

(75) Inventors: Moshe Saraf, Menasha, WI (US); Stephen L. Nunn, Appleton, WI (US); Thomas P. Keenan, Appleton, WI (US); Scott D. Dobslaw, Winchester, WI (US); Dale J. Fischer, Neenah, WI (US); Daniel J. Heuer, Fremont, WI (US); James J. Hlaban, Ogdensburg, WI (US); Michael K. Lewis, Kaukauna, WI (US); Richard W. Kubalek, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/272,422

(22) Filed: Oct. 16, 2002

(65) Prior Publication Data

US 2004/0077474 A1 Apr. 22, 2004

(51) Int. Cl.$^7$ ................................................. B65B 9/00
(52) U.S. Cl. ............................. 53/450; 53/550; 53/578; 493/349; 493/352; 493/356
(58) Field of Search .................................. 493/352, 349, 493/344, 356, 395, 397, 401, 405, 408, 476; 156/204, 164, 200; 53/450, 550, 578

(56) References Cited

U.S. PATENT DOCUMENTS

| | | |
|---|---|---|
| 3,231,356 A | 1/1966 | Giffen |
| 3,832,055 A | 8/1974 | Hamaker |
| 3,845,951 A | 11/1974 | Hamaker |
| 3,956,049 A * | 5/1976 | Johnsen ...................... 156/200 |
| 4,468,428 A | 8/1984 | Early et al. |
| 4,595,392 A | 6/1986 | Johnson et al. |
| 4,900,384 A | 2/1990 | Sanders et al. |
| 4,942,003 A | 7/1990 | Bold |
| 5,156,902 A | 10/1992 | Pieper et al. |

(Continued)

FOREIGN PATENT DOCUMENTS

| | | |
|---|---|---|
| DE | 198 56 447 A1 | 6/2000 |
| EP | 0 226 939 A2 | 7/1987 |
| EP | 0 254 393 A1 | 1/1988 |
| JP | 07316965 | 5/1995 |
| WO | WO 00/40197 A1 | 7/2000 |

OTHER PUBLICATIONS

International Search Report for PCT/US 03/19657, dated Feb. 17, 2004, 7 pages.

(Continued)

*Primary Examiner*—Sameh H. Tawfik
(74) *Attorney, Agent, or Firm*—Senniger Powers

(57) ABSTRACT

The invention is directed to method and apparatus for wrapping pads. A web of flexible wrapping material is adapted to be pulled in tension over a forming device. The forming device has first and second folding members having angled folding edges adapted for contact by respective opposite side margins of the web as the web is pulled past the folding edges. A web guide guides the web toward the folding edges. An opening between the web guide and the folding edges is adapted to be spanned by a central portion of the web as the web is pulled past the forming device. A series of pads are conveyed by a conveyor, one after another, and placed on the web as it is pulled past the forming device so that the pads move with the web over the opening and past the folding edges of the forming device. A surface applies a force to the pads to force the pads against the central portion of the web as the pads move across said opening. The force is sufficient to cup the web to position the pads for travel past the first and second folding members with concurrent folding of the side margins of the web by respective folding edges to form a tube around the pads.

29 Claims, 46 Drawing Sheets

U.S. PATENT DOCUMENTS

| | | | |
|---|---|---|---|
| 5,460,638 A | | 10/1995 | Lock |
| 5,492,522 A | * | 2/1996 | Rubar .......................... 493/325 |
| 5,660,662 A | | 8/1997 | Testone |
| 5,799,467 A | * | 9/1998 | Nankervis et al. ............ 53/450 |
| 5,866,173 A | | 2/1999 | Reiter et al. |
| 5,987,860 A | * | 11/1999 | Yang ........................... 53/550 |
| 6,041,579 A | * | 3/2000 | Savoury et al. ............... 53/551 |
| 6,059,710 A | | 5/2000 | Rajala et al. |
| 6,074,333 A | | 6/2000 | Rajala et al. |
| 6,159,882 A | | 12/2000 | Kean et al. |
| 6,165,306 A | | 12/2000 | Rajala |
| 6,220,999 B1 | | 4/2001 | Kugler et al. |
| 6,263,545 B1 | | 7/2001 | Pinto |
| 6,272,275 B1 | | 8/2001 | Cortright et al. |
| 6,330,735 B1 | | 12/2001 | Hahn et al. |
| 6,599,389 B1 | * | 7/2003 | Uneda ..................... 156/379.8 |
| 6,663,807 B2 | | 12/2003 | Klug |

OTHER PUBLICATIONS

Model B Rando–Web Process manual; Rando Machine Corporation of Macedon, N.Y.; 4 pages; admitted prior art.

M–6 Synchro Feeder manual; Fiber Controls Corporation of Gastonica, S.C.; 43 pages; admitted prior art.

D–106 Pneumatic Distributor manual; Fiber Controls Corporation of Gastonica, S.C.; 9 pages; admitted prior art.

Automatic Card Feeding System Masterchute–MC–W manual; Hollingsworth Saco Lowell Inc. of Greenville, S.C.; 13 pages; admitted prior art.

* cited by examiner

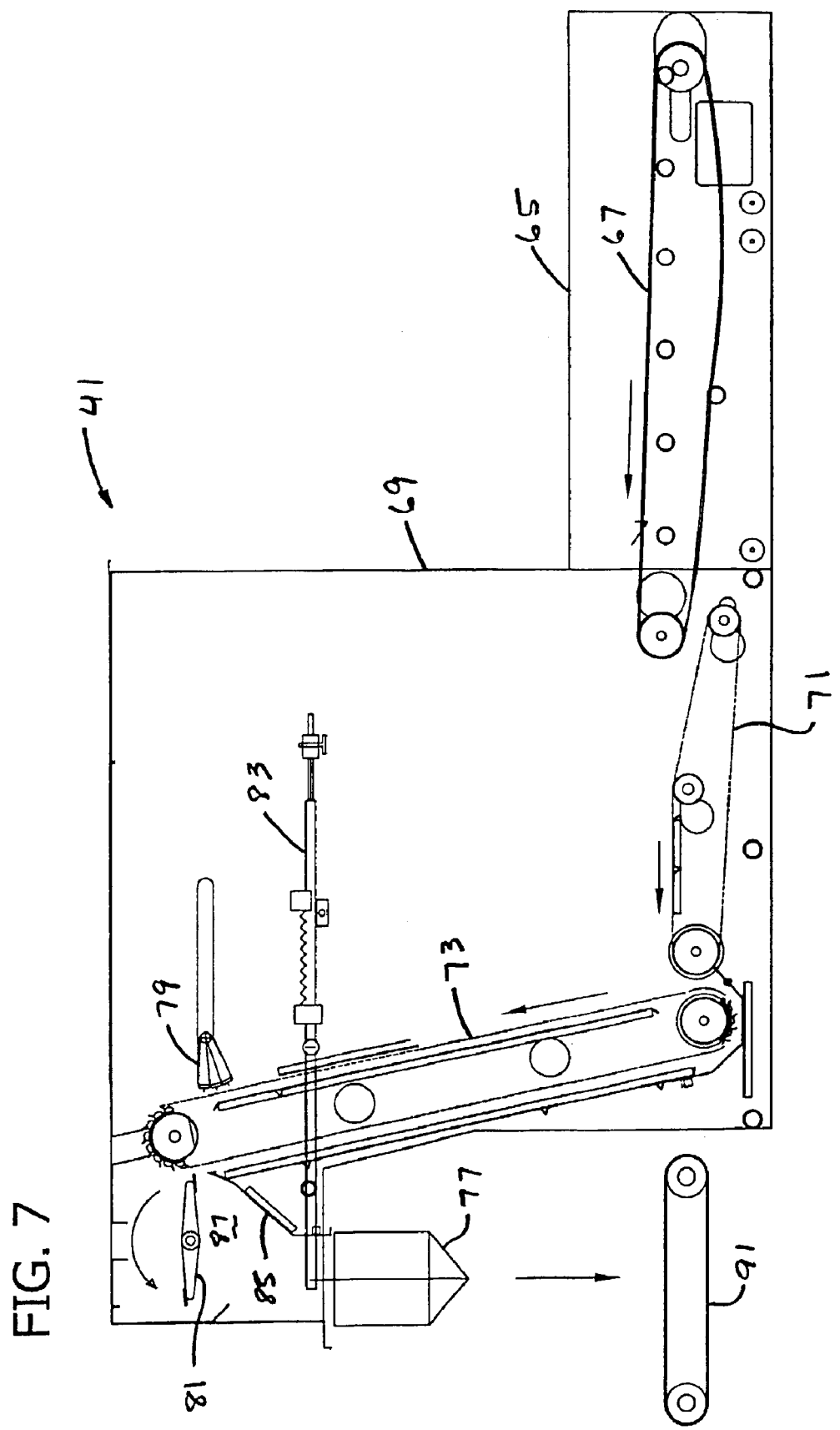

METHOD AND APPARATUS FOR WRAPPING PADS

BACKGROUND OF THE INVENTION

The invention relates generally to a method and system for wrapping pads and, more particularly, to a method and apparatus for wrapping feminine protection pads.

This invention is especially suited for the commercial manufacture of pads of the type shown in U.S. Pat. No. 4,595,392, entitled "Interlabial Pad", and U.S. Pat. No. 4,673,403, entitled "Method and Pad Allowing Improved Placement of Catamenial Device", both of which are assigned to Kimberly-Clark Corporation and incorporated by reference herein for all purposes. The pads described in these patents generally comprise a lamination of a layer of absorbent material (e.g., a blend of fibers, including cotton fibers) disposed between two cover layers, one of which is fluid pervious and faces the body when the pad is in use, and the other of which is typically fluid impervious. The pad is small compared to other feminine protection products and must be manufactured to relatively close tolerances. These size and tolerance requirements pose challenges to the efficient and economic production of this product on a commercial scale.

SUMMARY OF THE INVENTION

The apparatus and methods of the invention provide for the efficient and economic wrapping of pads, including but not limited to relatively small pads (e.g., interlabial pads) of the type described above which require relatively tight manufacturing tolerances. Such apparatus and methods have several aspects.

In one aspect, the invention is an apparatus for wrapping pads. The apparatus includes a forming device over which a web of flexible wrapping material is adapted to be pulled in tension. The forming device includes first and second folding members having angled folding edges adapted for contact by respective opposite side margins of the web as the web is pulled past the folding edges, a web guide for guiding the web toward the folding edges, and an opening between the web guide and the folding edges adapted to be spanned by a central portion of the web as the web is pulled past the forming device. The apparatus also includes a conveyor for conveying a series of pads, one after another, for placement on the web as it is pulled past the forming device so that the pads move with the web over the opening and past the folding edges of the forming device. The apparatus further includes a device for applying a force to the pads to force the pads against the central portion of the web as the pads move across the opening, the force being sufficient to cup the web to position the pads for travel past the first and second folding members with concurrent folding of the side margins of the web by respective folding edges to form a tube around the pads.

In another aspect, the invention is a method of wrapping pads. The method includes pulling a web of flexible wrapping material past a forming device having folding edges adapted for contact by respective opposite side margins of the web as the web is pulled past the folding edges, a web guide for guiding the web toward the folding edges, and an opening between the web guide and the folding edges adapted to be spanned by a central portion of the web as the web is pulled past the forming device. The method further comprises placing a series of pads, one after another, on the web as the web is pulled so that the pads move with the web across the opening and past the folding edges of the forming device. The method also includes applying a force to the pads to force them against the central portion of the web as the pads move across the opening, the force being sufficient to cup the web to position the pads and central portion of the web for travel past the first and second folding members with concurrent folding of the side margins of the web by respective folding edges to form a tube around the pads.

Other features will be in part apparent and in part pointed out hereinafter.

BRIEF DESCRIPTION OF THE DRAWINGS

FIG. 7 is an elevation of weighing apparatus of the fiber blending section;

FIG. 8 is a schematic elevation of a blend opener of the fiber blending section;

Corresponding reference numbers and characters indicate corresponding parts throughout the drawings.

DETAILED DESCRIPTION

Figure 1:
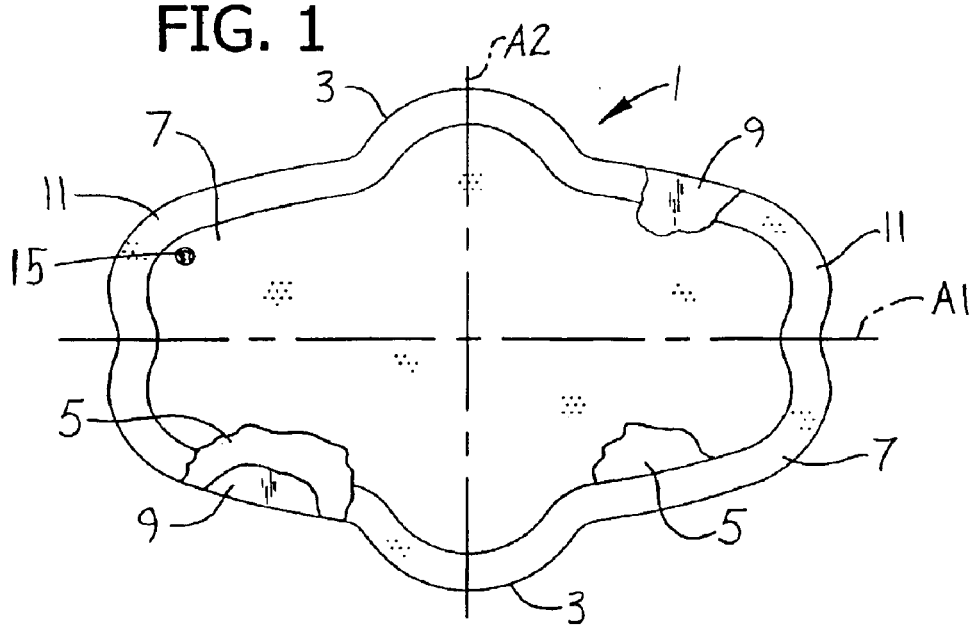
FIG. 1 is a view of one embodiment of an interlabial pad made in accordance with the apparatus and methods of the invention.
Figure 2:
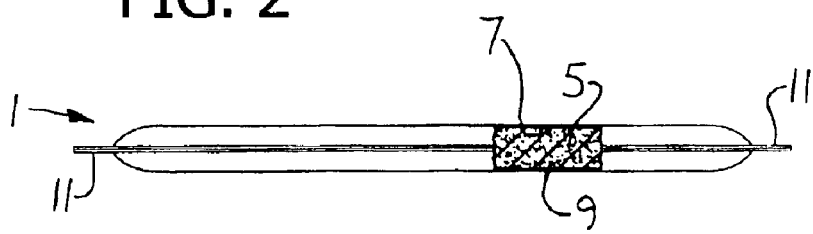
FIG. 2 is a sectional view of the pad of FIG. 1.

Referring to FIGS. 1 and 2, an interlabial pad manufactured in accordance with methods and apparatus of the invention is indicated in its entirety by the reference number 1. In the illustrated embodiment, the pad is generally oval in shape and has lateral projections 3. The pad may be manufactured in different sizes to fit different users. For example, in one size the pad has an overall length along a major axis A1 of about 3.1 in. and an overall width along a minor axis A2 of about 2.7 in. In another size the pad has an overall length along a major axis A1 of about 4.3 in. and an overall width along a minor axis A2 of about 2.7 in. As those skilled in the art will understand, the pad may be manufactured in other sizes and shapes without departing from the scope of this invention.

In general, the pad comprises an absorbent layer or "core" 5 laminated between first and second outer layers 7 and 9. The absorbent layer is preferably a blend of fibers, at least one of which is absorbent. By way of example, the fibers may comprise a blend of cotton fibers providing the requisite absorbency and rayon fibers providing resilience to the pad, with the cotton/rayon blend ratio preferably ranging from 90/10 to about 50/50, more preferably 80/20 to 55/45, and still more preferably about 60/40. Other fibers and blend ratios can also be used. Superabsorbent materials may also be included, as will be understood by those skilled in this field. The thickness of the absorbent layer will also vary, but preferably is in the range of from about 0.025 in. to about 1.5 in., and more preferably from about 0.05 in. to about 0.5 in., and even more preferably about 0.08 in. (approximately 2 mm. for low capacity interlabial pads).

The first outer layer 7 (sometimes referred to as the "cover" or body-side layer since it faces the body when the pad is in use) is a fluid-pervious layer which may comprise a suitable polymer, such as polypropylene BCW, having a basis weight of 22 g/m$^2$. The second outer layer (sometimes referred to as a "baffle" layer) may comprise polyethylene film, for example, having a thickness of 0.75–1.0 mil. Pads having other laminated configurations, including those where the baffle layer is fluid-pervious, are also contemplated. In any event, the lamination is sealed around the periphery of the pad, as indicated at 11.

Figure 3:
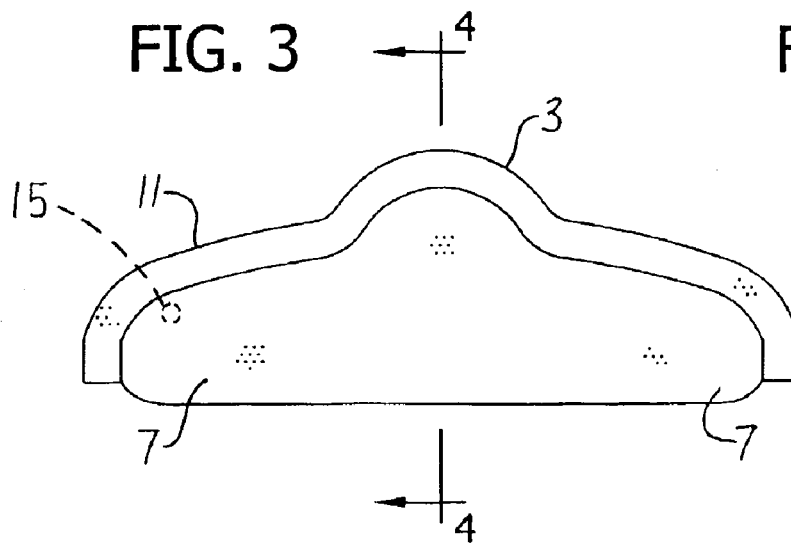
FIG. 3 is a view showing the pad of FIG. 1 in folded condition.
Figure 4:
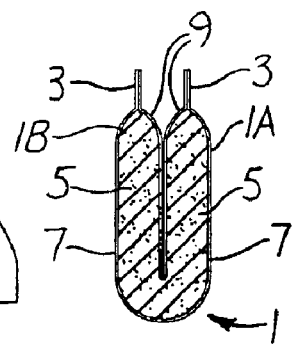
FIG. 4 is a sectional view taken in the plane of line 4—4 of FIG. 3.

FIGS. 3 and 4 illustrate the pad in a folded condition in which the pad is folded along its major axis A1 to a position in which opposite side sections 1A, 1B of the pad face one another, with the cover (body-side) layer 7 facing out for contact with the body when the pad is inserted for use. In one embodiment, the pad is maintained in this folded condition by one or more adhesive spots 15 on the cover (baffle) layer 9. As thus folded, the lateral projections 3 on the pad combine to form an area which can be conveniently gripped by the user of the pad to insert it into proper position in the body.

Figure 5:
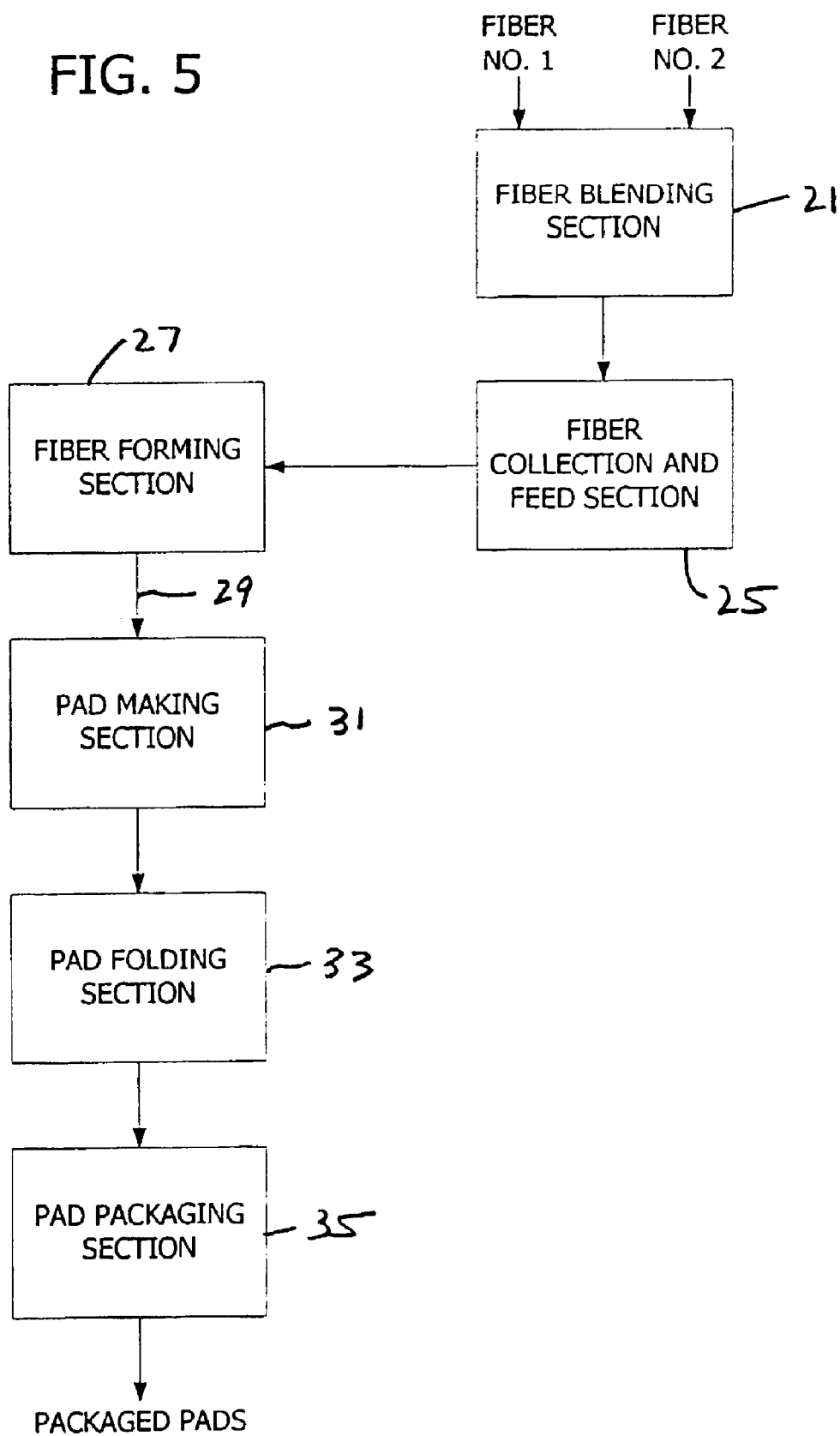
FIG. 5 is a flow diagram illustrating various sections of a manufacturing process of the invention for making pads.

FIG. 5 illustrates various stages in an overall process for the commercial manufacture of absorbent articles of laminated construction, including the interlabial pads 1 described above. This process includes a fiber blending section 21 which blends raw fibers (e.g., cotton and rayon fibers), and a fiber collection and feed section 25 for collecting a supply of blended fibers and feeding them to a fiber forming section 27 where the fibers are formed into a relatively narrow continuous web used to make the fluid-absorbent layers of the final product (e.g., interlabial pad 1). The process also includes a pad-making section 31 which combines the absorbent layer with the fluid-pervious (cover) layer 7 and, if used, the baffle layer 9 to make individual pads. The process also includes a folding section 33 which includes apparatus for folding the pads delivered from the pad-making section 31, and a pad packaging section 35 in which the folded pads are individually wrapped and, optionally, collated into groups and placed in cartons or other suitable bulk packaging. Each of these stages of the process are described in detail below.

Figure 6:
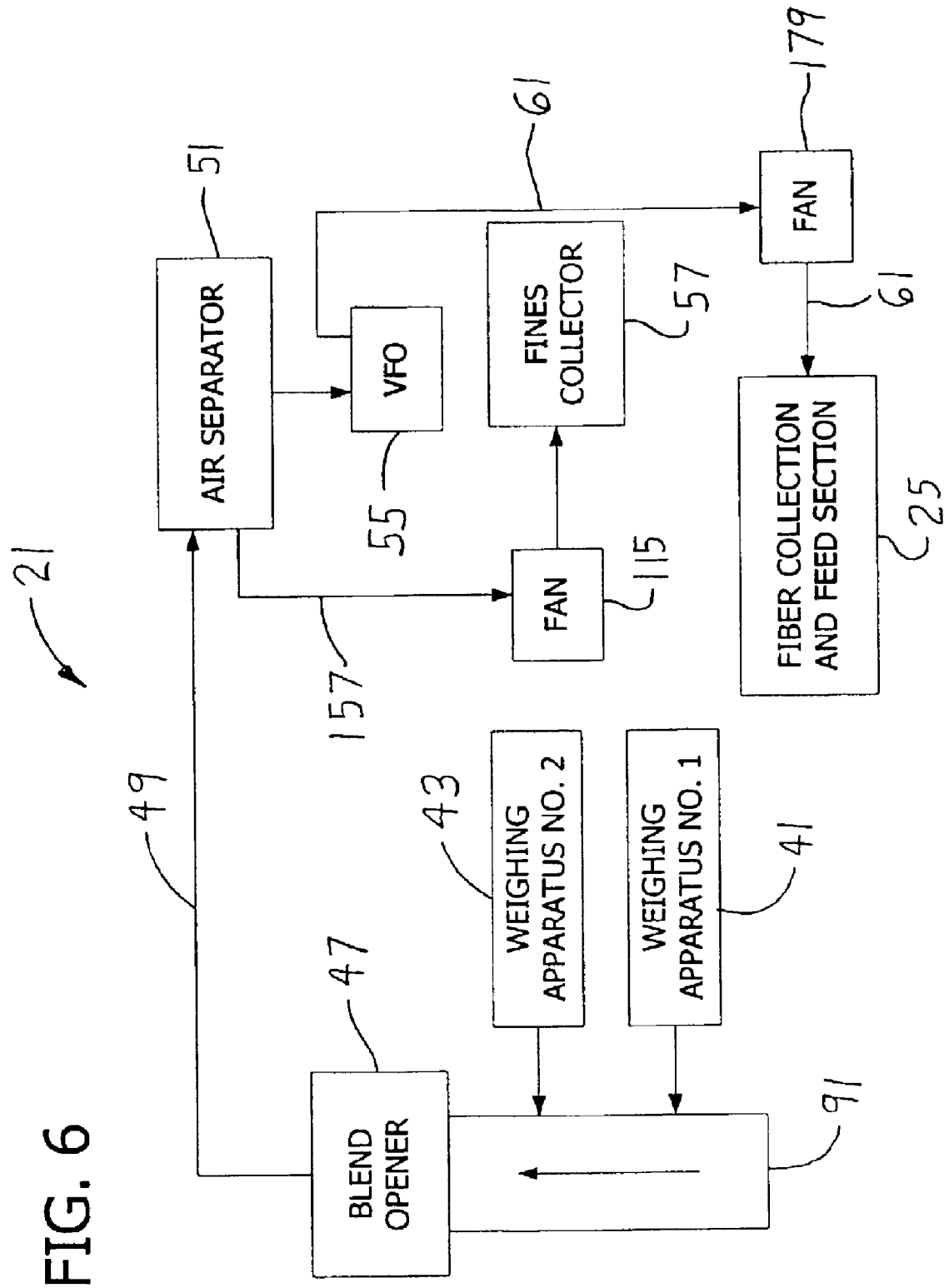
FIG. 6 is a flow diagram illustrating various components of one embodiment of a fiber blending section of the manufacturing process.

FIG. 6 is a flow diagram illustrating one embodiment of the fiber blending section 21. In this particular embodiment, the section 21 comprises first weighing apparatus 41 operable to weigh out and discharge quantities of a first fiber (e.g., cotton) and second weighing apparatus 43 operable to weigh out and discharge quantities of a second fiber (e.g., rayon). The weighed and discharged quantities are conveyed to a blend opener, generally designated 47, where the fibers are separated ("opened"), mixed and then carried away from the blend opener by an air duct 49 of a pneumatic conveyor system. The pneumatic conveyor system includes an air separator 51 which separates the longer fibers from the air stream and delivers them to a fine opener 55. The shorter fibers ("fiber fines") are delivered to a fines collector, such as a bag filter 57. The fine opener 55 further opens and mixes the fibers for conveyance through an air duct 61 to the fiber collection section 25 of the system. Each one of these components of the blending section is described in more detail below.

For purposes of the description, the apparatus of the invention has a machine-direction MD which extends generally in the direction of motion of the machine, a lateral cross-direction CD which extends transversely to the machine direction, and a z-direction Z. As used herein, the machine-direction MD is the direction along which a particular component or material is transported lengthwise along and through a particular, local position of the apparatus. The cross-direction CD lies generally within the plane of the material being transported through the process, and is transverse to the local machine-direction MD. The z-direction Z is aligned substantially perpendicular to both the machine-direction MD and the cross-direction CD, and extends generally along a depth-wise, thickness dimension of the material.

The first weighing apparatus 41 is operable to deliver successive weighed-out quantities of first fibers, such as cotton fibers. The particular unit shown in FIG. 7 is a M-6 "Syncro-Feeder" weigh pan feeder sold by Fiber Controls® Corporation of Gastonia, N.C. The apparatus comprises a hopper 65 for holding a supply of raw fibers, and a conveyor 67 in the hopper for delivering clumps of fibers from the supply to a weigher housing 69 containing a feed conveyor 71 for receiving fibers from the hopper conveyor 67 and conveying them to an inclined lift conveyor 73 having pins or spikes thereon which pick fibers off the feed conveyor 71 and convey them to a weigher comprising a weigh hopper 77 at the outlet of the unit. An oscillating comb 79 adjacent to the upper end of the inclined conveyor 73 combs the fibers on the conveyor and separates ("opens") them to prevent large clumps of fiber from entering the weigh hopper 77. Fibers separated by the comb are carried to the top of the inclined conveyor 73 and discharged onto one or more rotating doffer bars 81 which effect a more uniform distribution of the fibers into the weigh hopper. Excess fibers combed out by the comb 79 fall back onto the feed conveyor 71 for recycling. The degree of fiber separation can be controlled by adjusting the speed of the inclined conveyor 73 and/or the spacing between the comb 79 and the inclined conveyor.

The weigh hopper 77 is equipped with a suitable device 83 for measuring the weight of fibers in the hopper. When a quantity of fibers having a predetermined weight is received in the hopper (e.g., 1120 grams of cotton fibers), a door 85 above the hopper closes to prevent further fibers from entering the weigher until after it has unloaded. When the door is closed, fibers delivered from the conveyor 73 accumulate temporarily in a holding chamber 87 above the weigh hopper 77. At the appropriate time, the weigh hopper opens to deliver a quantity of fibers of predetermined weight onto a conveyor 91 (e.g., an endless belt conveyor) positioned below, after which the door 85 above the weigher opens to admit more fibers into the weigh hopper to repeat the cycle.

The second weighing apparatus 43 is essentially identical to the first weighing apparatus 41 and is operated to discharge successive weighed-out quantities of second fibers. Each of these quantities (e.g., 480 grams of rayon fibers) is combined with a weighed-out quantity of the first fibers. This may be accomplished in a variety of manners, as by dumping a quantity of second fibers directly on a pile of first fibers as the latter pile is conveyed beneath the weigher of the second unit. The combined quantities are then conveyed by the conveyor 91 (FIG. 6) to the blend opener.

Referring to FIG. 8, the blend opener 47 may be of the type sold as Model B1X24/30 Opening Blender" from Fiber Controls® Corporation of Gastonia, N.C. As shown, the machine comprises a housing 97 having an inlet in one side wall receiving the discharge end of the conveyor 91 from the weighers 41, 43, and an outlet in its top wall connected to the air duct 49 of the pneumatic conveyor system which generates a high-velocity stream of air flow through the duct in a direction away from the outlet. Mounted in the housing 97 immediately above the discharge end of the conveyor 91 is a feed roll 101 which is driven to match the speed of the conveyor 91. The feed roll 101 is formed with a series of axial ridges or flutes 103 along its outer surface and is preferably spring biased in a downward direction against a stop (not shown) to a position in which it is spaced a predetermined distance (e.g., 3 in.) from the upper reach of the conveyor belt 91. The function of the feed roll 101 is to spread the fibers as a layer across the width of the conveyor 91, and to press the fibers down against the conveyor for a controlled feed of the fibers forward at a relatively slow speed (e.g., 9 fpm). At this point in the process, the fibers making up the layer on the conveyor 91 are relatively stratified, with the fiber dumped first on the conveyor (e.g., cotton) being on the bottom and the fiber dumped second being on top. The feed roll 101 and conveyor 91 are preferably driven at the same speed by a common drive the speed of which is adjustable as needed.

A large cylindric beater roll 105 having an axial dimension generally corresponding to the full width of the conveyor 91 (e.g., 24 in.) is mounted for rotation in the housing 97 upstream from the conveyor 91 and feed roll 101. A multiplicity of pins or teeth 107 are mounted on the outer surface of the roll, each pin being threaded in a mounting block 109 secured to the roll. Preferably, the pins 107 are arranged in a number of parallel rows extending along the outer surface of the roll in an axial direction. (For example, a beater roll having a diameter of 24 in. may have 12 rows of pins mounted at equal angular intervals around the roll.) A cut-off blade 111 is mounted adjacent the outlet of the housing and extends the full axial length of the roll closely adjacent the tips of the pins (e.g., the clearance may be about 0.02 to 0.05 in.).

The beater roll 105 is rotated at relatively high speed (e.g., about 750 rpm) by a suitable motor and drive train (not shown). Fibers fed toward the roll 105 by the conveyor 91 and feed roll 101 are pulled and combed at high speed by the pins 107 and carried to the outlet of the housing 97 where they are drawn into the air duct 49 and entrained in the air stream generated by the pneumatic conveyor system. The cut-off blade 111 assists in the removal of fibers from the roll 105. The high-speed pulling and combing action on the fibers, combined with the pneumatic conveyance of the fibers from the outlet of the machine, further separates ("open") and mixes the fibers, as will be understood by those skilled in this field.

Figure 9:
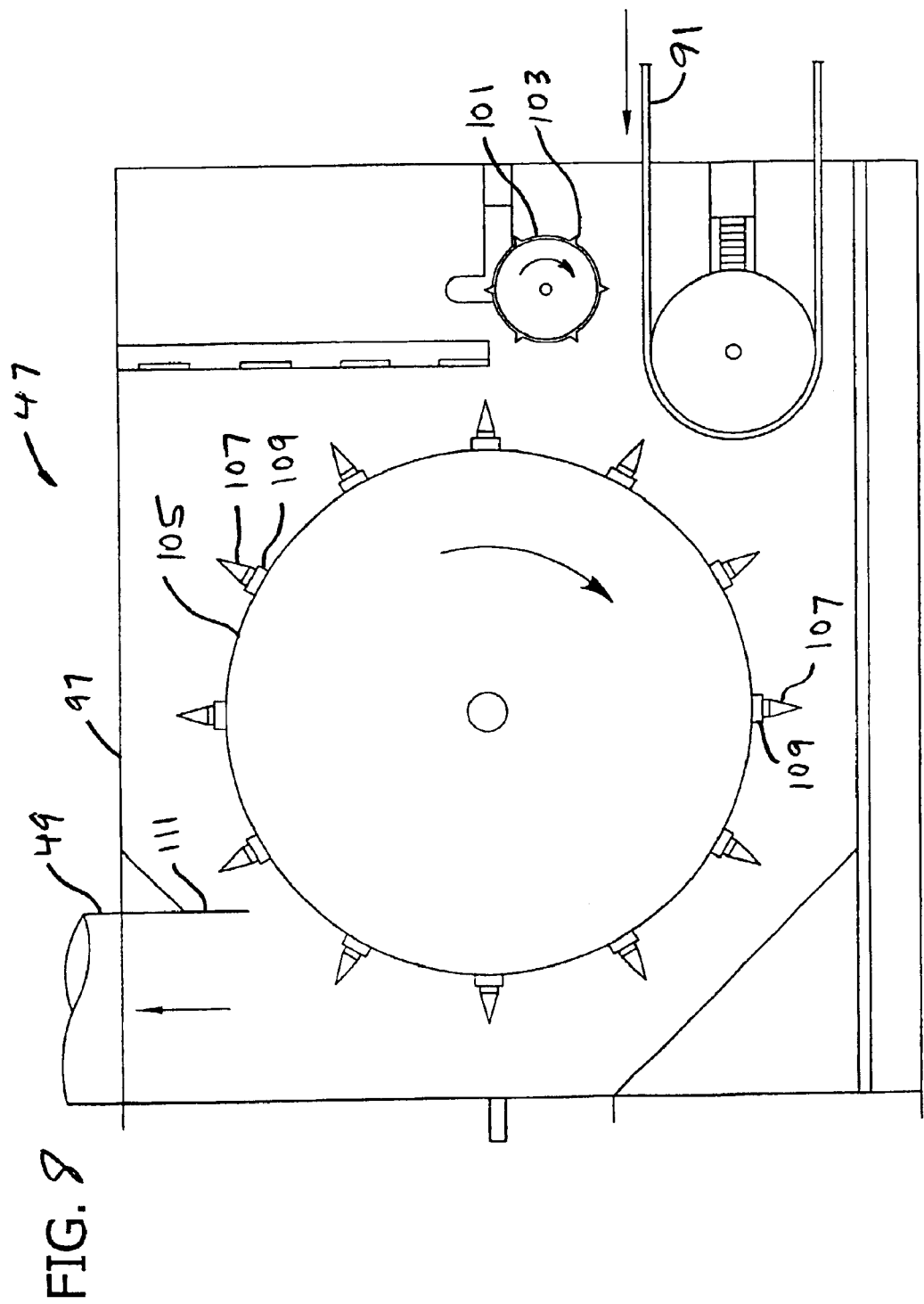
FIG. 9 is a schematic elevation of a separator of the blending section.
Figure 9:
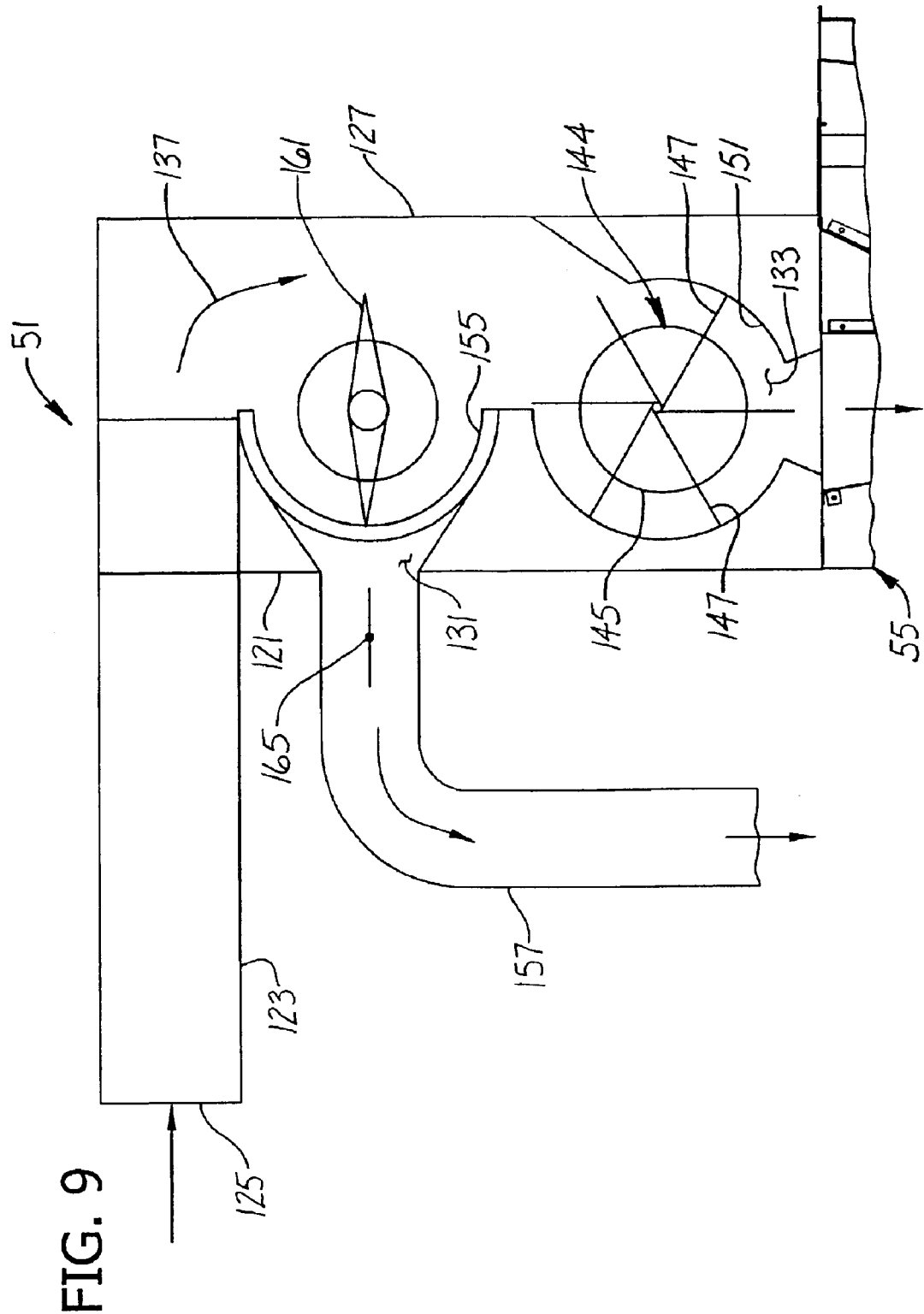

The air duct 49 conveys the fibers from the blend opener 47 to the air separator 51 by means of a high-speed air stream generated by a first transfer fan 115 located downstream from the separator (see FIG. 6). In one embodiment, for example, the air moves at a velocity in the range of 2500–4000 FPM and at a flow rate of 1300–3500 CFM. As shown in FIG. 9, the air separator 51 in the preferred embodiment comprises a housing 121 having an inlet section 123 with an inlet 125 for receiving airborne fibers from the blend opener 47 and an outlet section 127. The outlet section 127 has an upstream air outlet 131 for the exit of air from the separator and a downstream fiber outlet 133 for exit of fibers from the separator into the fine opener 55.

The inlet and outlet sections 123, 127 of the housing 121 are configured to direct the air stream entering the inlet along a path 137 which turns a corner, e.g., a 90° corner at the junction of the inlet and outlet sections in a preferred embodiment. As a result of this change in direction, many of the heavier fibers are moved by centrifugal force toward the outside of the turn and continue on to the fiber outlet 133. A rotary air lock 144 at the fiber outlet 133 substantially inhibits the flow of air through the outlet while allowing for the passage of such fibers, thus "separating" the fibers from the air. Similar to a revolving door, the air lock 144 comprises a central hub 145 and a plurality of sealing arms 147 extending radially out from the hub which wipe against a wall 151 defining the outlet 133 to substantially seal against the passage of air. In the preferred embodiment, the air lock 144 is motor driven at a speed which may be varied to meet the fiber feed requirements of the system. As the air lock rotates, it sweeps fibers deposited between the arms 147 through the outlet 133.

Because the flow of air through the fiber outlet 133 is substantially blocked by the rotary air lock 144, essentially all of the air entering pneumatic distributor 51 exits through the air outlet 131. A screen 155 is mounted in the housing 121 adjacent this air outlet 131 to catch the larger fibers while permitting small fibers or "fines" to pass through the air outlet to an air duct 157 which leads to the fines collector 57, which may be of any suitable construction, such as a Model AF-2 bag filter sold by Fiber Controls® Corporation of Gastonia, N.C. The mesh size of the screen 155 can vary, depending on the desired characteristics of the final product, but preferably the openings in the screen have a maximum dimension of about 0.125 in. Fibers collected on the screen are removed by a rotatable blade 161 mounted in the housing 121. The blade carries the fibers away from screen and delivers them back to the air stream for transport to the fiber outlet 133.

A damper 165 in the air duct 157 connected to the fines collector 57 is movable between an open position, as shown, for permitting air flow through the air outlet 131 to the collector, and a closed position for blocking the flow of air through the air outlet. It will be noted in this regard that if the pneumatic conveyor system comprises multiple air separators and associated equipment, there may be occasions where a particular unit(s) is not needed, in which case the damper 165 can be closed to block the flow of air through that particular separator. The first transfer fan 115 is mounted in the air duct 157 between the air separator 51 and the fines collector 57.

Figure 10:
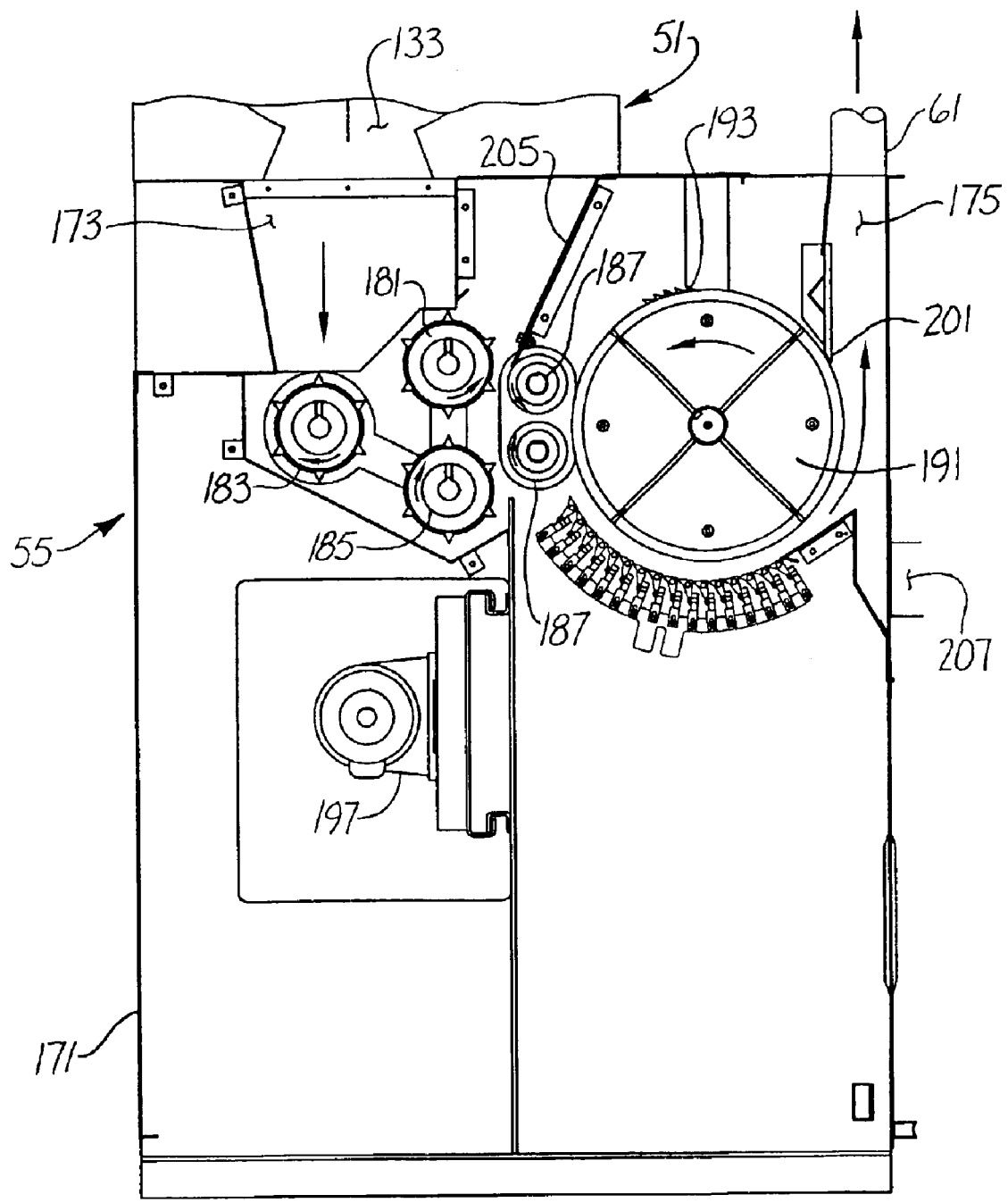
FIG. 10 is a schematic elevation of a fine opener of the blending section.

FIG. 10 illustrates one embodiment of the fine opener 55, which is sold as Model VFO 36 from Fiber Controls® Corporation of Gastonia, N.C. The fine opener comprises a housing 171 having an inlet 173 connected to the fiber outlet 133 of the air separator 51, and an outlet 175 connected by air duct 61 to the fiber collection and feed section 25, a second transfer fan 179 being mounted in this air duct 61 to generate an air stream for transporting fibers from the fine opener 55 to the fiber collection and feed section 25.

A plurality of fluted nip rolls (e.g., three such rolls 181, 183, 185 are shown in FIG. 10) are mounted in the housing 171 immediately downstream from the inlet 173 and rotate to transport fibers entering the fine opener 55 along a path between a pair of closely spaced feed rolls 187, also having fluted surfaces. (The flutes on the nip rolls 181, 183, 185 are typically relatively narrow, resembling blades or fins extending the full length of each roll at spaced circumferential intervals around the roll, while the flutes on the feed rolls 187 are preferably somewhat wider, resembling gear teeth with flat tops.) The feed rolls 187 feed the fibers to a clothing cylinder 191 which rotates in the housing 171 at high speed, e.g., 1000 rpm. Suitable card clothing 193 (e.g., teeth or hooks) is mounted on the clothing roll 191 along a continuous spiral path from one end of the cylinder to the other, as will be understood by those skilled in this art. The nip and feed rolls are preferably driven by a common DC motor 197, the output of which is adjustable to vary the speed of these rolls, as needed. The clothing roll 191 is preferably driven by an AC motor (not shown) for rotation of the roll at a constant speed.

As the clothing roll 191 rotates at high speed past the feed rolls 187, the clothing on the roll functions to further open the fibers and to transport them to the outlet 175 of the machine, where the fibers are drawn up and through the outlet. A cut-off blade 201 mounted adjacent the outlet has an edge positioned closely adjacent the roll 191 for substantially preventing fibers from being carried by the clothing roll past the outlet 175. A similar blade 205 is mounted with its tip end adjacent the upper feed roll 187 for preventing build-up of fibers on the feed roll. Air flows into the housing 171 through an air inlet 207.

A fiber-level sensor (e.g., photocell), not shown, is mounted in the housing 171 of the fine opener 55 for controlling the level of fiber delivered to the inlet 173. In the event the fibers back up to a level considered excessive, the sensor is operable to signal the upstream weighing apparatus 41, 43 and blend opener 47 to stop further delivery of fibers until the level of fibers drops below a predetermined level (e.g. the level of the sensor), after which the upstream equipment is signaled to resume operation. Other sensing devices operating in different manners may be used.

Figure 11:
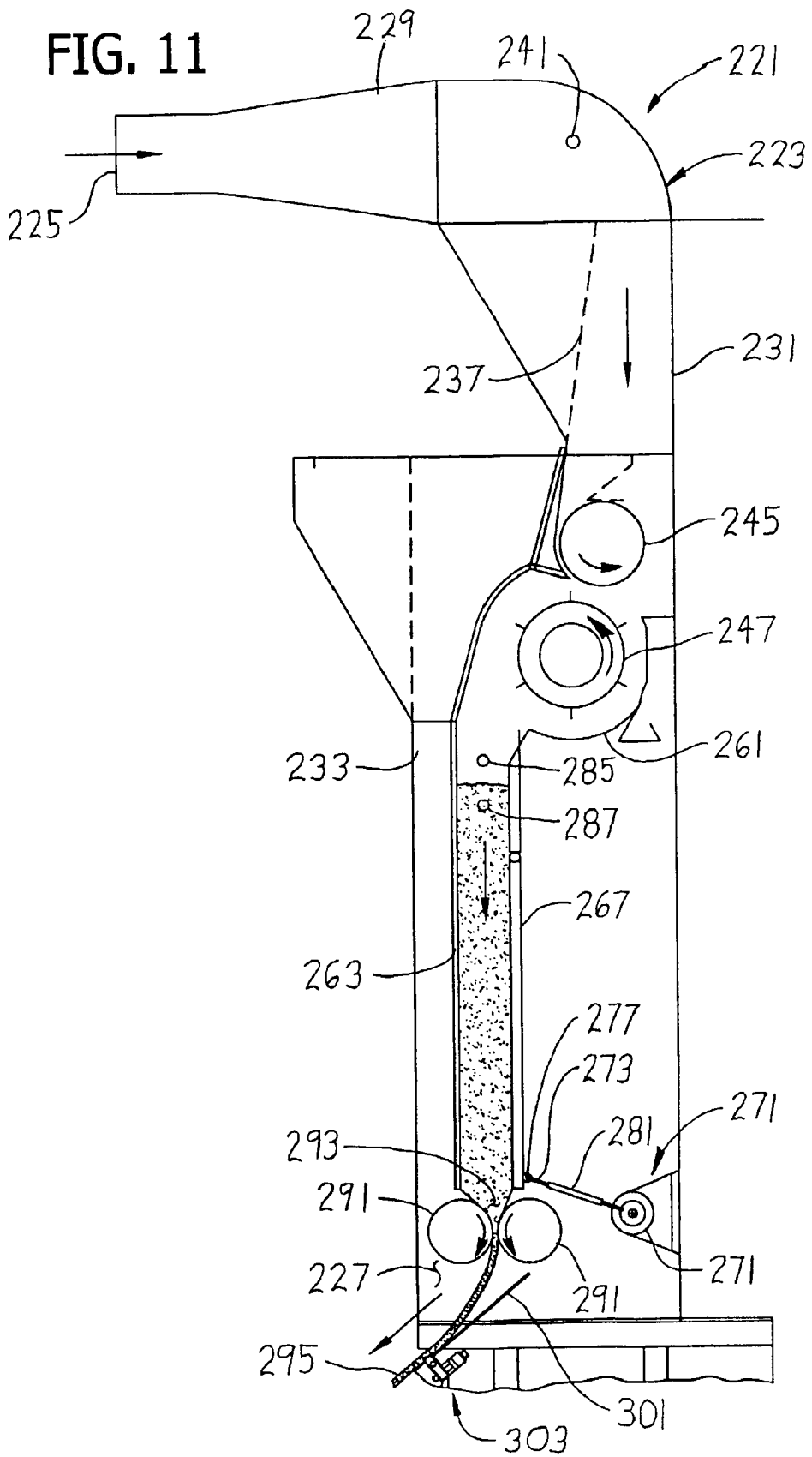
FIG. 11 is a side elevation of a feed chute of the fiber collection and feed section.
Figure 12:
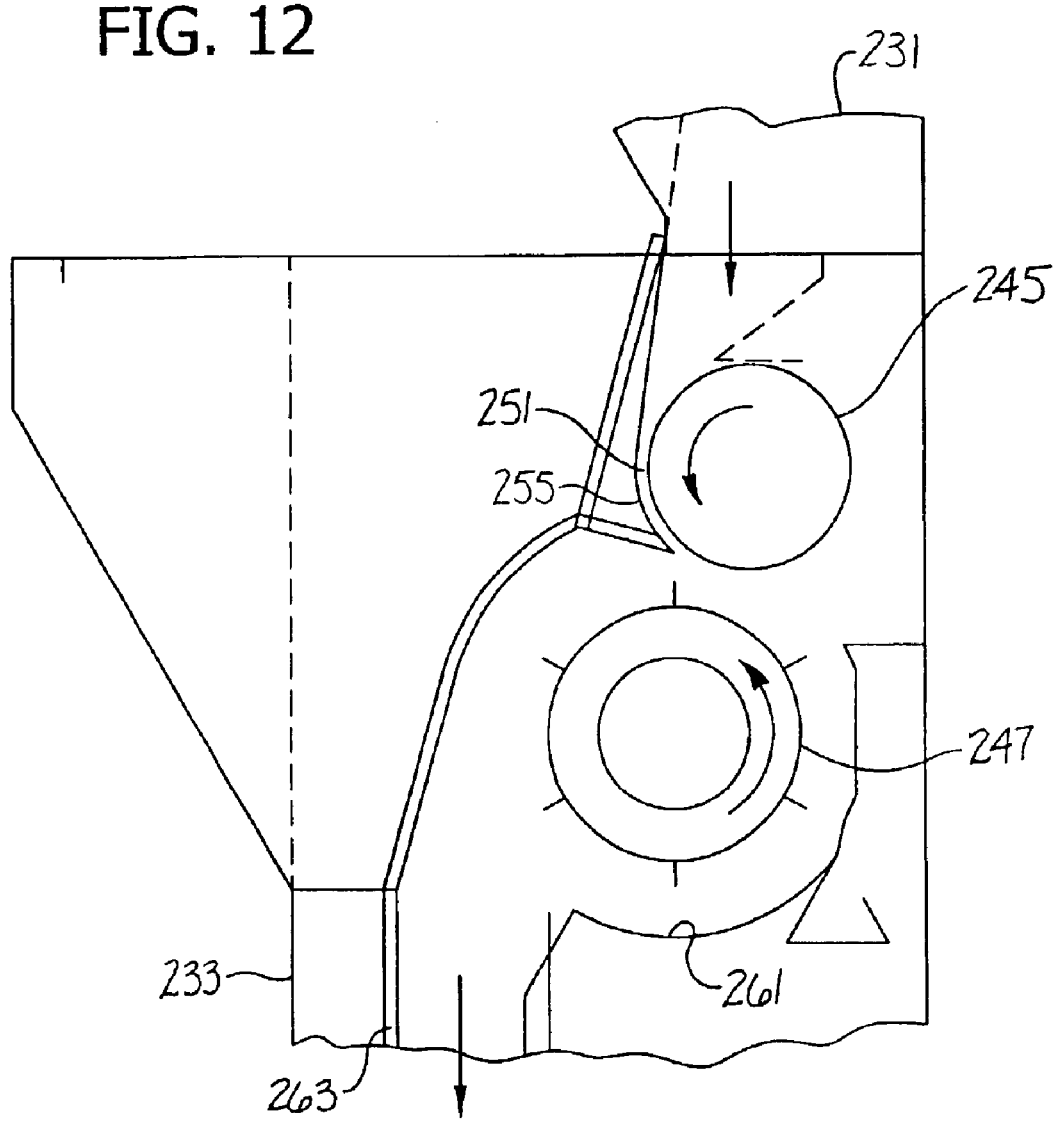
FIG. 12 is an enlarged view showing feed and beater rolls of the feed chute of FIG. 11.

FIGS. 11 and 12 illustrate apparatus at the fiber collection and feed section 25 of the system downstream from the fine opener 55. This apparatus comprises, in one embodiment, a feed chute, generally designated 221. The feed chute collects (accumulates) a supply of blended fibers and feeds the fibers as an initial layer or mat of blended fibers to the fiber forming section 27. More specifically, the feed chute 221 comprises a housing 223 having an inlet 225 connected to the air duct 61 for receiving fibers from the fine opener 55, and an outlet 227 through which a continuous supply of blended fibers is discharged to the forming section. The particular feed chute 221 shown in this embodiment is a Model FCF-40 chute feeder sold by Platt-Saco-Lowell, formerly of Greenville, S.C.

The housing has an upper section 229 which includes an upper chute 231 for holding a supply of fibers delivered through the inlet 225, and a lower section 233. One wall 237 of the upper chute 231 is perforated (e.g., the wall may be a screen of fine mesh) to permit the escape of incoming air from the chute. The level of fiber in the upper chute 231 is controlled by suitable means, such as a pressure switch 241 adjacent the inlet operable to signal a shutoff of the upstream equipment (e.g., weighing apparatus 41, 43, blend opener 47 and fine opener 55) in the event the air pressure in the upper housing section 229 exceeds a predetermined pressure, indicating that the upper chute 231 is full, and to signal activation of the upstream equipment when the pressure falls below a predetermined pressure, indicating that the supply of fiber in the upper chute has fallen to a level requiring replenishment.

A feed roll 245 is rotatably mounted in the lower section 233 of the housing immediately below the upper chute 231 to feed fibers from the upper chute 231 to a beater roll 247. The fiber is fed past the feed roll 245 through a gap 251 (FIG. 12) defined by a guide surface 255 spaced from the feed roll 245 a suitable distance (e.g., about 0.25 in.). The feed roll 245 is preferably equipped with card clothing (not shown) similar to the clothing cylinder of the fine opener 55, and the beater roll 247 has a construction similar to the beater roll 105 in the blend opener 47, although it is preferably somewhat smaller (e.g., a diameter of 10.5 in. with twelve rows of pins or teeth). The feed roll 245 is preferably rotated by a variable speed motor (not shown) to feed the fiber to the beater roll 247 at the desired rate. The beater roll 247 is preferably rotated at a suitable speed (e.g., 1800 rpm) by a constant speed motor to feed the blended fibers into the lower section 233 of the feed chute and to perform an additional opening step on the fibers. Fibers on the beater roll 247 are directed by an adjacent guide wall 261 in the housing to the upper end of a fiber accumulation chute 263 in the lower section 233 of the housing 223.

Referring to FIG. 11, the lower accumulation chute 263 is defined, in a preferred embodiment, by vertical walls, one of which comprises a shaker plate 267 pivoted at its upper end for back-and-forth oscillation by means of a shaker arm assembly generally designated 271 adjacent the lower end of the plate. The shaker arm assembly 271 comprises one or more shaker arms 273 each of which has an inner end connected to a wheel 275 at an off-center location, and an outer end connected (as by a clevis 277) to the shaker plate 267, the arrangement being such that rotation of the wheel causes the shaker arm and the shaker plate to oscillate back and forth. This movement prevents the bridging of fibers in the lower chute 263 and facilitates the uniform feed and packing of fiber in the chute to provide a supply of blended fibers, e.g., a column of substantially uniform density or "basis weight" (typically measured in grams/square meter). The length of the shaker arm 273 is adjustable by means of a turnbuckle 281 or the like, so that the amplitude of the oscillating movement can be varied, as needed. The shaker arm wheel 275 (or wheels) is preferably driven at the desired speed by a variable speed DC motor (not shown). Other means may be used instead of the shaker plate and shaker arm assembly 271 for facilitating the flow and packing of fibers in the lower chute 263.

The level of fibers in the lower accumulation chute 263 is controlled by suitable means, such as a pair of upper and lower sensors, e.g., upper and lower photo cells indicated at 285 and 287, respectively, in FIG. 11. The upper photo cell 285 is operable to signal a shutoff of the upstream equipment (e.g., weigh apparatus 41, 43, blend opener 47 and fine opener 55) in the event the height of the column of fibers in the lower chute 263 exceeds a predetermined height, indicating that the lower chute is full. The lower photo cell 287 is operable to signal activation of the upstream equipment when the height of the column falls below a predetermined level, indicating that the need for additional fibers. The upper and lower sensors 285, 287 are preferably closely spaced for maintaining the height of the fiber column relatively constant so that the density of fibers discharged from the chute is substantially uniform.

Fibers in the lower chute 263 are fed through the outlet 227 by feed means comprising, in one embodiment, a pair of compression rolls 291 defining a compression nip 293 immediately adjacent the outlet of the housing. These compression rolls 291 preferably function to compress the fibers into a continuous mat or layer 295 of blended fibers which is discharged through the outlet 227 for delivery to the fiber forming section 27 of the system.

Figure 13:
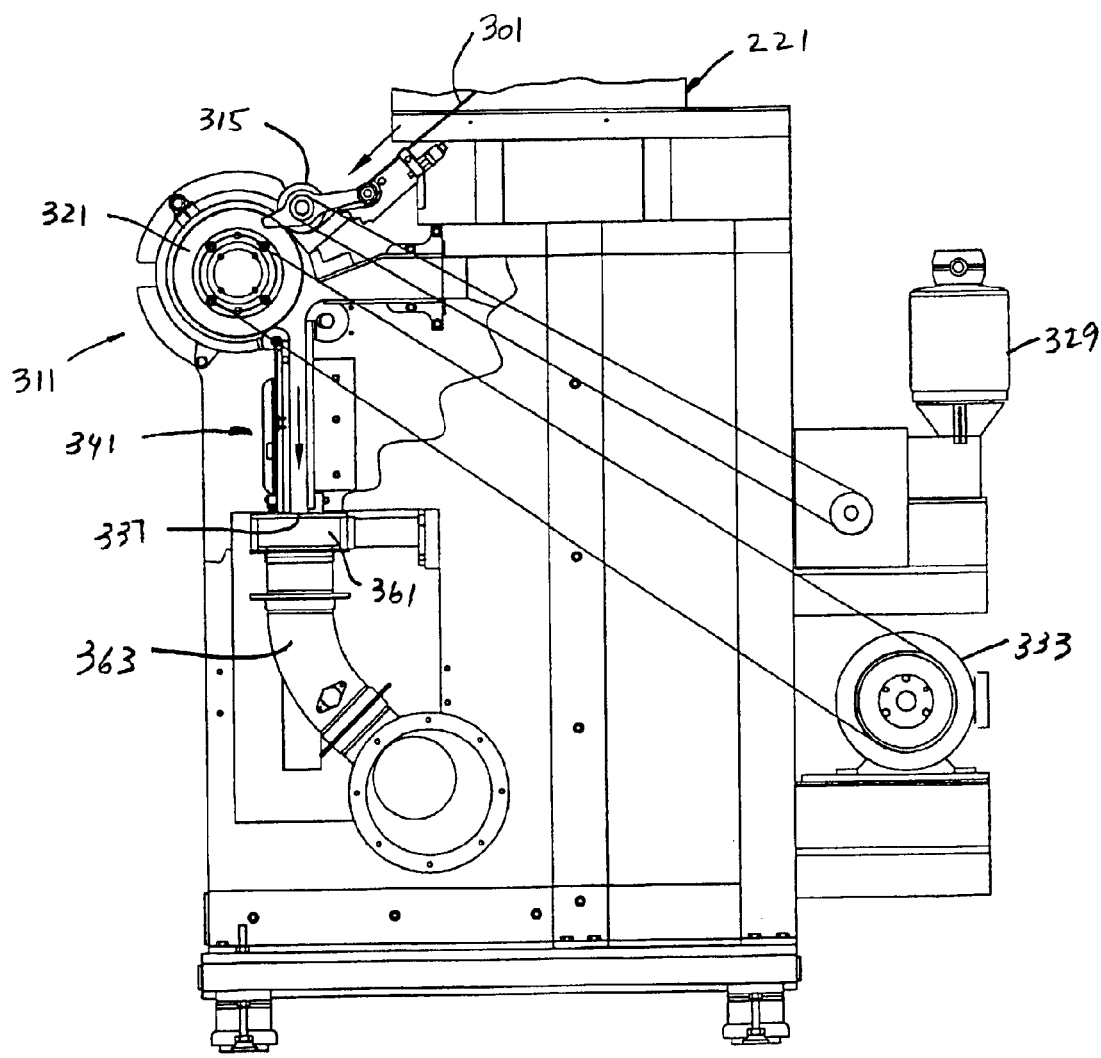
FIG. 13 is a side elevation of apparatus in the fiber forming section of the invention.
Figure 14:
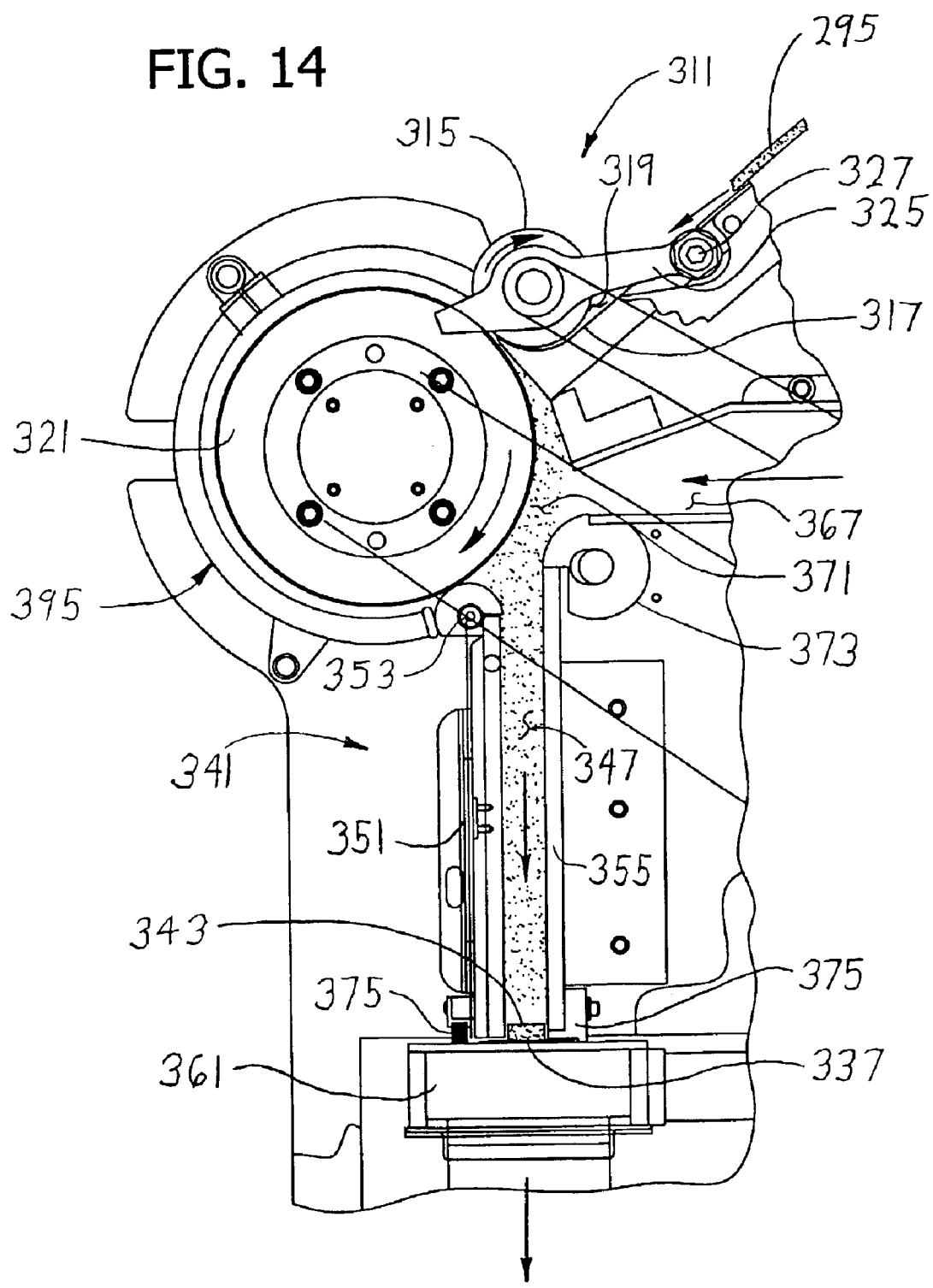
FIG. 14 is an enlarged view of portions of FIG. 13 showing individual fibers being "air laid" onto a moving conveyor.
Figure 15:
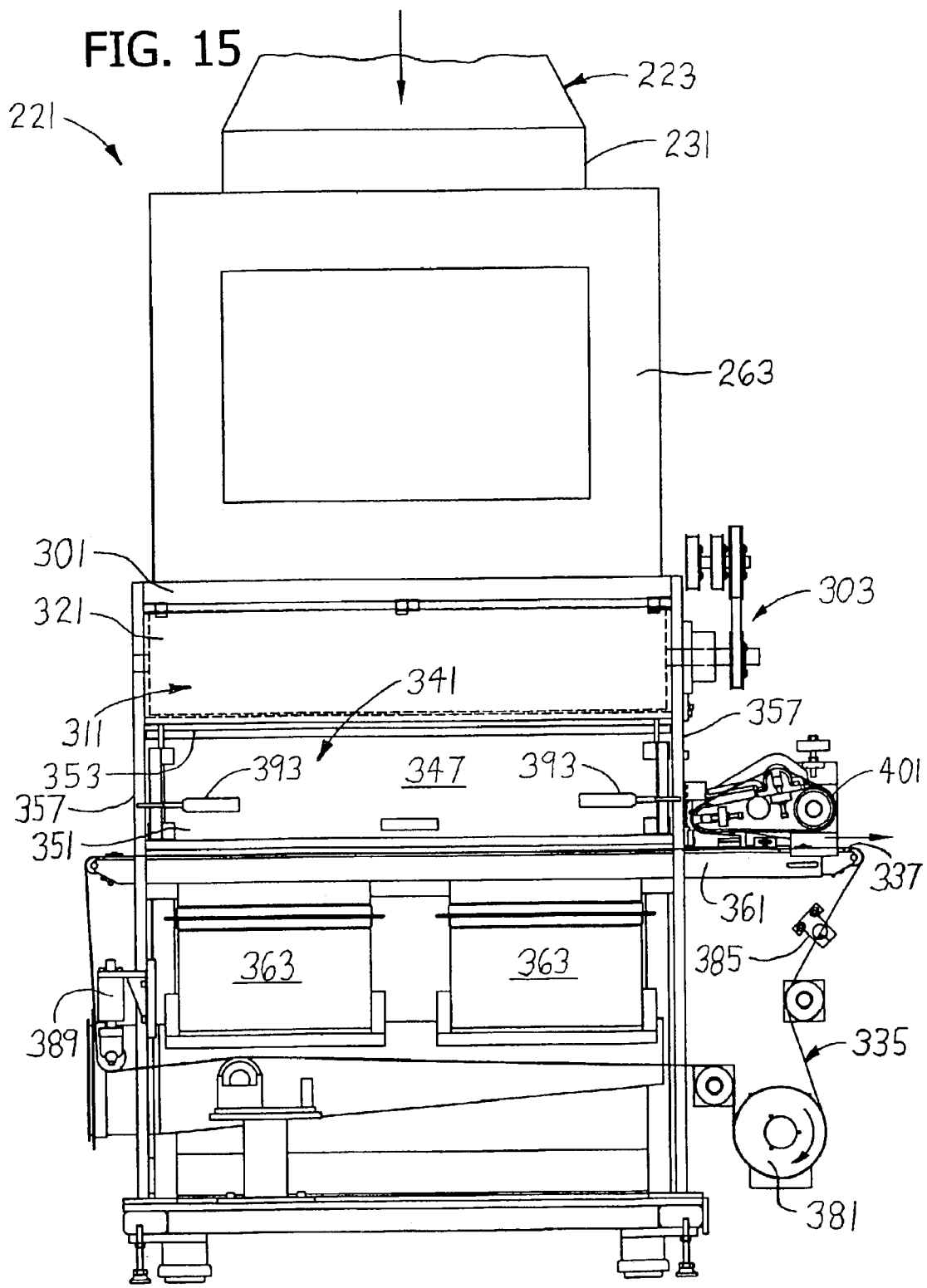
FIG. 15 is a left end elevational view of FIG. 13.

FIGS. 13–15 illustrate one embodiment of the forming section 27 of the system of the invention. In this section, the layer 295 of fiber delivered from the outlet 227 of the feed chute 221 is broken up and reformed as a preferably (but not necessarily) narrower layer having a width generally corresponding to the width of the absorbent layer of the final product (e.g., layer 5 of pad 1). In general, the fiber forming section 27 of this particular embodiment comprises a transfer device 301 for feeding the layer of fiber from the outlet 227 of the feed chute to a fiberizing station 303 at the downstream end of the transfer device. In the preferred embodiment, the transfer device is a slide (also designated 301) down which the layer gravitates. Alternatively, the transfer device could be an endless conveyor or other device.

Apparatus generally designated 311 is provided at the fiberizing station 303 for breaking up the incoming layer 295 into individual fibers, a process which may be referred to as "fiberizing". As illustrated, this fiberizing apparatus 311 comprises a feed mechanism including a feed roll 315 spaced from a guide surface 317 (FIG. 14) to form a gap 319 through which the layer 295 of fibers is fed to a fiberizing mechanism comprising, in one embodiment, a roll 321 having teeth, e.g., a lickerin roll, mounted immediately adjacent the gap. Alternatively, a rotary hammer mill or other device may be used.

The feed roll 315 is carried by a pair of levers 325 (only one shown in FIG. 14), each of which has a pivot connection 327 with the machine frame for adjusting the size of the gap 319. Preferably, the gap is set to be less than the thickness of the incoming layer 295 (e.g., 0.012 in. compared to about 2.5 in.) so that the layer of fibers is compressed and fed forward to the fiberizing roll 321 at a controlled rate of speed (e.g., 6 fpm). The feed roll 315 is preferably driven by a variable speed DC motor 329 (FIG. 13). The fiberizing roll 321 preferably rotates in a direction opposite the rotational direction of the feed roll 315, and the teeth on the roll 321 function to break up or "fiberize" the layer 295 into small tufts and individual fibers. The fiberizing roll is preferably driven by an AC motor 333 at a constant, relatively high speed (e.g., 1800 to 2400 rpm).

The fiber forming section 27 also includes a conveyor 335 (FIG. 15) having foraminous forming surface 337 positioned below the fiberizing roll 321 and preferably running in a direction generally transverse (e.g., at right angles) to the direction of feed to the fiberizing roll, and fiber-directing apparatus, generally designated 341, for directing fibers from the fiberizing roll to the surface 337 on which they are reconstituted as a "reformed" layer 343 (FIG. 14) on the conveyor 335, hereinafter referred to as the "reforming" conveyor. In one embodiment, the forming surface 337 of the reforming conveyor 335 comprises an endless belt made of wire mesh or screen, the openings being appropriately sized for the forming (e.g., 11% open area). The forming surface 337 is preferably substantially narrower than the width of the layer 295 fed to the fiberizing roll 321 (e.g., 3 in. versus 40 in.) and, in one embodiment, extends generally parallel to the axis of rotation of the fiberizing roll.

It will be understood that a fiberizing mechanism other than a roll with teeth (e.g., lickerin roll 321) could be used without departing from the scope of this invention. Any mechanism (e.g., a rotary hammer mill) can be used, provided it is capable of breaking up the layer 295 into separate fibers for reformation on the reforming conveyor 337 in substantially random orientation.

Referring to FIGS. 14 and 15, the fiber-directing apparatus 341 comprises, in the preferred embodiment, an air chamber 347 positioned between the fiberizing roll 321 and the reforming conveyor 335. The air chamber 347 has an upper inlet end located adjacent the fiberizing roll 321 and a lower outlet end located immediately above the forming surface 337 of the conveyor 335, although the air chamber could have orientations other than vertical without departing from the scope of this invention.

As viewed in FIG. 15 in which the reforming conveyor 335 transports fibers from right to left, the upper end of the air chamber has a length generally corresponding to the axial length of the fiberizing roll 321 which, in turn, is preferably at least as wide as the layer 295 delivered from the feed chute 221. Referring to FIG. 14, the air chamber 347 has a front (left) wall defined at least in part in one embodiment by a door 351 pivoted at its upper end at 353 so that the door may be swung up and down between open and closed positions, a rear wall 355, and opposite side walls 357 (FIG. 15). The air chamber 347 has a width (i.e., the distance between the front and back walls 351, 355 of the chamber) at its lower end generally corresponding to the width of the reformed layer 343 of fibers formed on the reforming conveyor 335. The forming surface 337 of the conveyor 335 is positioned over an elongate air manifold 361 which communicates with a vacuum fan (not shown) by means of air duct 363. The arrangement is such that operation of the fan generates an air stream down through the air chamber 347 and through the forming surface 337 to "air lay" a layer of fibers on the forming surface. Air is provided to the air chamber 347 via an airway 367 (FIG. 14) adjacent the juncture of the fiberizing roll 321 and the upper inlet end of the air chamber.

The airway has a throat 371 which is adjustable in size to regulate the flow of air to the air chamber, adjustment being effected by means such as a movable sabre bar 373 or other suitable device. Seals are provided to prevent the drawing of air into the air chamber 347, including sealing strips 375 along the sides of the door, the top edge of the door, and strips along the bottom edges of the door and rear wall (FIG. 14). The vacuum fan should be sized to generate a relatively high-speed stream of air through the air chamber 347 sufficient to direct fibers from the fiberizing roll 321 onto the reforming conveyor 335 to form a layer of blended fiber of suitable thickness and density.

The reformed layer 343 may be formed on a conveyor other than an endless belt. For example, the reformed layer could be deposited or "air laid" on a rotatable vacuum drum of the type well known in the art for producing air formed fibrous webs.

The breaking up or disintegration of the layer 295 of fibers by the fiberizing roll 321 and deposit of the fibers as a reformed layer 343 on the reforming conveyor 335 tends to randomize the orientation of the fibers, resulting in good tensional strength of the final product in all directions and more uniform wicking and distribution of bodily fluid in all directions away from the location of impingement on the fibers. Further, reforming the layer 295 at an angle (e.g., 90°) which is transverse to the machine direction MD of feed to the fiberizer 321 tends to average any cross sectional variations in the layer.

As best illustrated in FIG. 15, the reforming conveyor 335 is driven by a drive roll 381 powered by a suitable motor to drive the conveyor at a speed substantially faster than the speed at which the initial layer 295 of fiber is delivered from the feed chute 221 to the fiberizing roll 321. Preferably, the width of the initial layer 295 delivered from the feed chute is at least 5 times greater than the width of the reformed layer 343 on the reforming conveyor 335, and the reforming conveyor preferably runs at a speed at least 10 times greater than the speed at which the initial layer is fed to the fiberizing roll.

By way of example, the initial layer may have a width of about 40 in. and a thickness of about 2.5–3.0 in., and the speed at which the initial layer is fed to the fiberizing roll may be 5–8 fpm. On the other hand, the reformed layer may have a width of about 3 in. and a height of about 0.5 in., and the reforming conveyor 335 may run at a speed of 370 fpm. The speed of the reforming conveyor is preferably adjustable. Fiber dust is removed from the reforming conveyor by a cleaner 385 mounted at a location upstream from a belt drive roll. In one embodiment, the cleaner comprises an air jet which is operable to blow fibers off the conveyor and a vacuum pick-up (not shown) opposite the air jet. Other cleaning mechanisms may be used. The endless belt of the conveyor 335 is maintained under tension by a conventional tensioning device indicated at 389.

The door 351 at the front of the air chamber 347 may be opened to access the reforming conveyor 537 and associated equipment. During normal operation, however, the door 351 is held in its closed position by a pair of locking pins 393. An additional security system, generally designated 395 in FIG. 14, may also be provided to lock the door closed.

Figure 16:
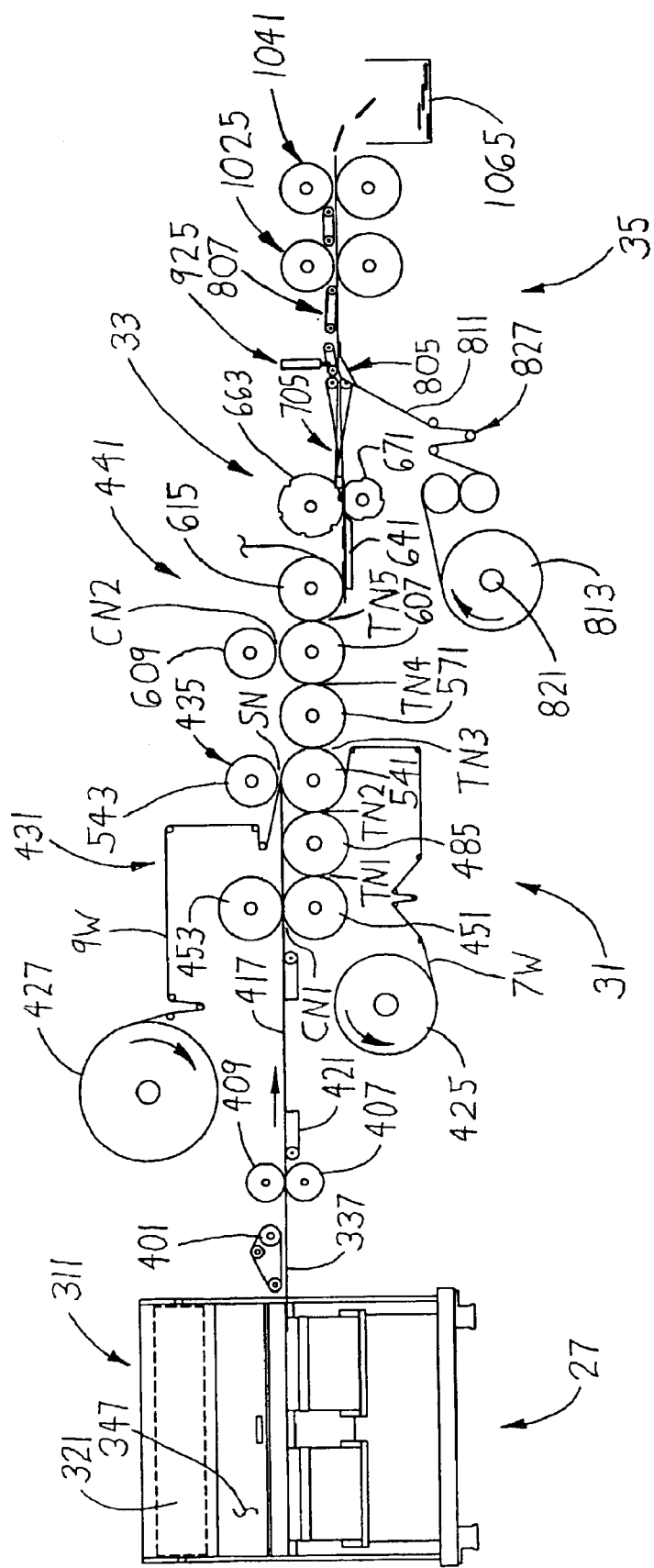
FIG. 16 is a schematic view showing a fiber forming section, pad making section, pad folding section and pad packaging section of the invention.
Figure 17:
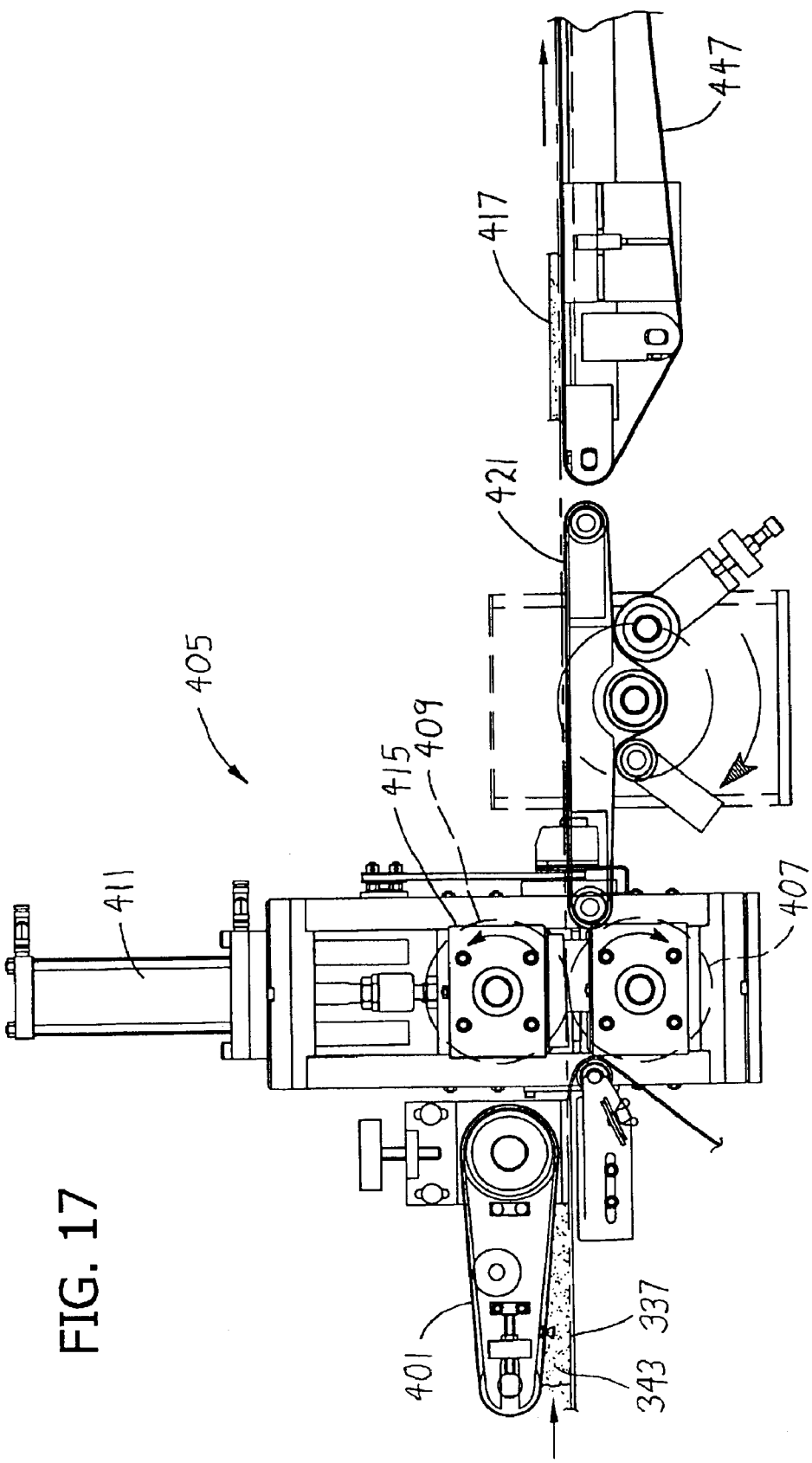
FIG. 17 is a side elevation showing a web of blended fibers being compressed by pressure rolls.

After the fibers are reformed on the reforming conveyor 335 as a preferably narrower layer, the reformed layer 343 is compressed to a final thickness. Preferably, compression occurs in two stages. In a first stage, the reformed layer is lightly compressed by a compression conveyor 401 positioned above the reforming conveyor 335 downstream from the air chamber 347 (FIGS. 15–17). The compression conveyor 401 is preferably an endless belt having a lower reach spaced from the forming surface 337 of the reforming conveyor 335 by a distance sufficient to lightly compress the incoming layer 343 of fibers. The vertical position of the compression conveyor 401 is preferably adjustable to vary the size of the gap between the two belts and thus the magnitude of the compressive forces applied to the layer, as needed.

In the second stage, the layer 343 is more severely compressed by a de-bulking module, generally designated 405 in FIG. 17. In one embodiment, this module 405 comprises a pair of pressure rolls having hardened surfaces, the lower pressure roll 407 being mounted in fixed position and the upper roll 409 being vertically movable relative to the lower roll, as permitted by a power cylinder 411 mounted above the upper roll. The power cylinder exerts a downward force (e.g., 2400 lbs) on bearing blocks 415 at the ends of the upper roll to hold the blocks down against fixed stops (not shown) which maintain a gap of predetermined size between the pressure rolls unless the compressive force exerted by the rolls 407, 409 on the layer 343 exceeds a predetermined force, in which event the upper roll 409 will yield in an upward direction. The size of the gap at the nip of the rolls 407, 409 can be adjusted by changing the position of the fixed stops. The compressive force exerted by the pressure rolls is preferably sufficient to compress the layer 343 to a final thickness (e.g., 0.08 in. for an interlabial pad) which is substantially the same as the thickness of the absorbent layer of the final product (e.g., layer 5 of pad 1). As thus compressed, the layer 343 is conveyed, preferably as a continuous integral web 417 (FIG. 17) of blended fibers, by one or more conveyors 421 to the pad-making section 31.

Referring to FIGS. 16–19, the pad-making section 31 comprises, in general, first and second unwind rolls 425, 427 on which are wound webs 7W, 9W of material corresponding to the cover and baffle layers 7, 9 of the final pad 1, and a first cutting station 431 at which the web 417 of blended fibers is cut to form individual absorbent bodies in the web (e.g., cores 5 for pads 1). Section 31 also includes a web sealing station 435 at which the cover and baffle webs 7W, 9W are applied to opposite faces of the bodies 5 to form a laminated web 437 (FIG. 19) which is sealed around the bodies 5, and a second cutting station 441 at which the laminated web 437 is cut around the pads prior to transport of the pads to the folding section 31. Each of these components is described in detail below.

Figure 18:
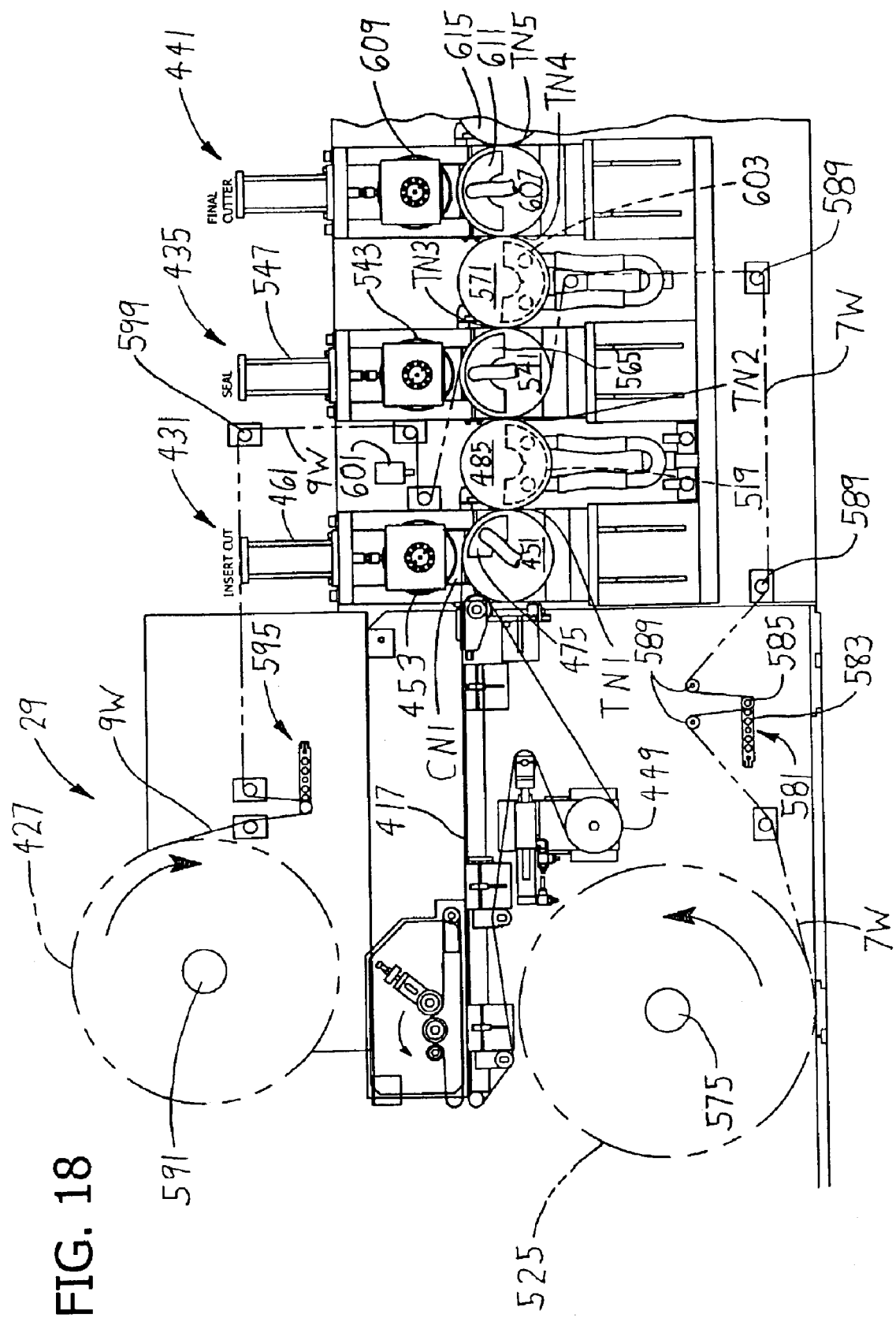
FIG. 18 is a schematic elevation of apparatus in the pad making section.

A conveyor (e.g., an endless belt conveyor 447 including a belt tensioning device 449) receives the blended-fiber web 417 at the entry end of the pad-making section, which is the left end as viewed in FIG. 18, and conveys the web 417 to the first cutting station 431. Cutting apparatus is provided at this station comprising, in one embodiment, opposing cutting rolls 451, 453 which define a first cutting nip CN1. One of these rolls (451) is a knife (die) roll and the other (453) is an anvil roll. In this embodiment, the knife roll 451 is mounted in fixed vertical position below the anvil roll 453 but this orientation may be reversed. The knife roll 451 has a series of cutting dies (blades) 457 (FIG. 20) mounted on the roll in a pattern corresponding to the pattern of absorbent bodies (e.g., cores 5) to be cut in the web. The anvil roll 453 has a hardened, polished metal surface and is preferably positioned so that the gap between the rolls at the first cutting nip CN1 is sufficiently small (e.g., 0.0005 in.) to enable the cutting blades 457 to cut substantially completely through the blended-fiber web 417.

The anvil roll 453 is preferably vertically movable relative to the knife roll 451 in the same manner as described above in regard to the upper pressure roll 409, a power cylinder 461 being provided for this purpose. The cylinder exerts a downward force on bearing blocks of the anvil roll 453 to hold the blocks down against fixed stops (not shown) and thus maintain the size of the gap (if any) at the first cutting nip CN1 unless the compressive force exerted by the rolls 451, 453 on the web 417 exceeds a predetermined force, in which event the upper roll will yield in an upward direction. The size of the gap can be adjusted by changing the position of the fixed stops, as will be understood by those skilled in this field.

After the web 417 has been cut to form the absorbent bodies (e.g., cores 5), it is desirable to maintain the bodies in precise position as they are transported through the pad-making section 31, so that the various components of the final pads (e.g., pads 1) are in substantially precise registration. To this end, the knife roll 451 is a vacuum roll comprising a cylindric body 465 (see FIGS. 20–22) formed with vacuum passages including, in one embodiment, axial passages 467 running from the ends of the body along the length of the body and radial passages 469 extending from the axial passages 467 radially outward to form vacuum openings 471 (FIG. 20) in the outer surface of the body. Vacuum boxes 475 are mounted at opposite ends of the body 465, each box being open adjacent a respective end face of the body. The vacuum boxes 475 communicate by means of air ducts 479 with a vacuum system comprising at least one vacuum fan (not shown) for generating a negative pressure in the vacuum boxes to draw air through the passages 467, 469 in the body. Seals 483 around the opening in each vacuum box 475 are positioned close to the respective end faces of the rotating cylindric body 465 to seal against leakage of air from the box.

Figure 20:
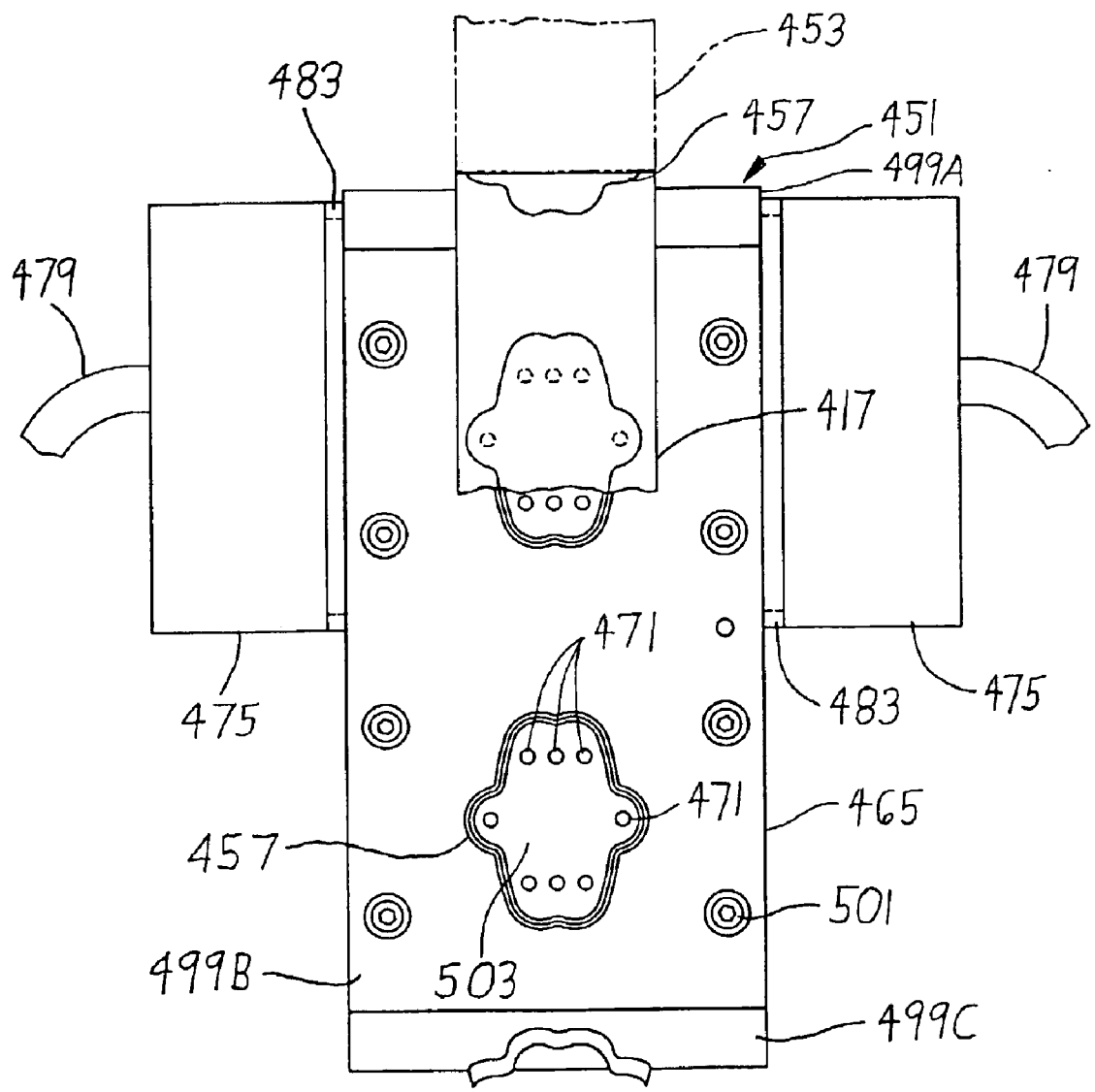
FIG. 20 is a schematic elevation of a knife roll at a first cutting station in the pad making section.

In the embodiment shown in FIGS. 18 and 20, the vacuum boxes 475 extend over about a 90° arcuate segment along the upper part of the knife roll 451 from about the 12:00 position adjacent the first cutting nip CN1 to about a 3:00 position for transfer of the absorbent bodies to a first transfer cylinder 485, the transfer occurring at a first transfer nip TN1 defined by the knife roll 451 and transfer cylinder 485. The vacuum openings 471 in the outer surface of the knife roll 451 are so arranged and located that the absorbent bodies cut from the web are vacuum gripped and held in precise position on the knife roll as it rotates in a clockwise direction from the cutting nip CN1 to the first transfer nip TN1, where the absorbent bodies are transferred to the first transfer cylinder 485 rotating in the same direction, as will be described. Scrap material 491 (i.e., trim from the web 417 around the absorbent bodies) is removed from the knife roll during or after the transfer of the absorbent bodies takes place, as by means of a vacuum duct 493 (see FIG. 22). The duct 493 has an inlet adjacent the knife roll 451 and communicates with the aforementioned vacuum system to draw the scrap material 491 into the duct for delivery to the inlet section of the feed chute 221 for recycling, or to a suitable waste collector for disposal.

Figure 21:
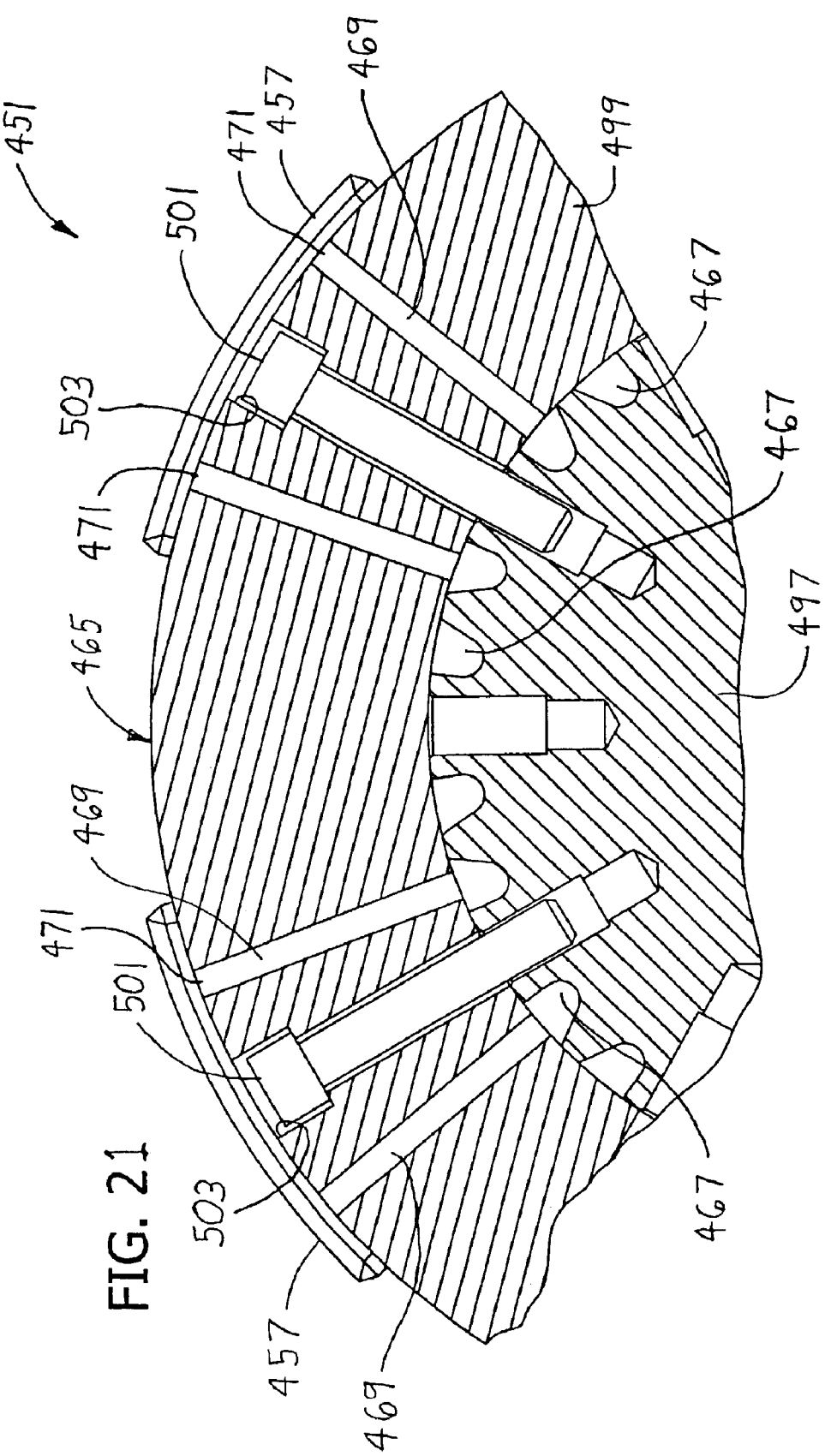
FIG. 21 is a partial sectional view showing the construction of the knife roll of FIG. 20.
Figure 22:
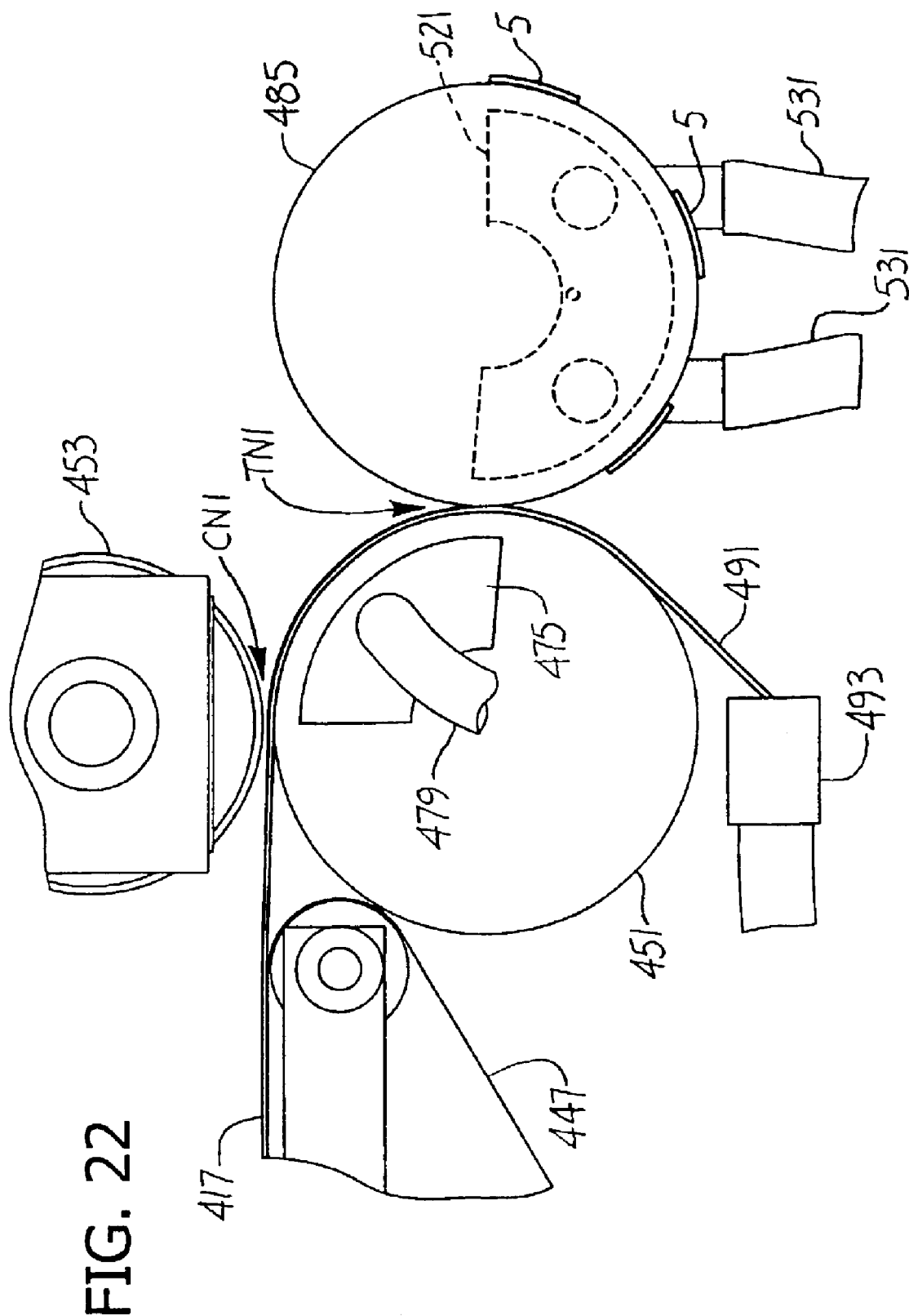
FIG. 22 is a schematic view showing a blended-fiber web passing through a nip between the knife roll and a first transfer cylinder.
Figure 23:
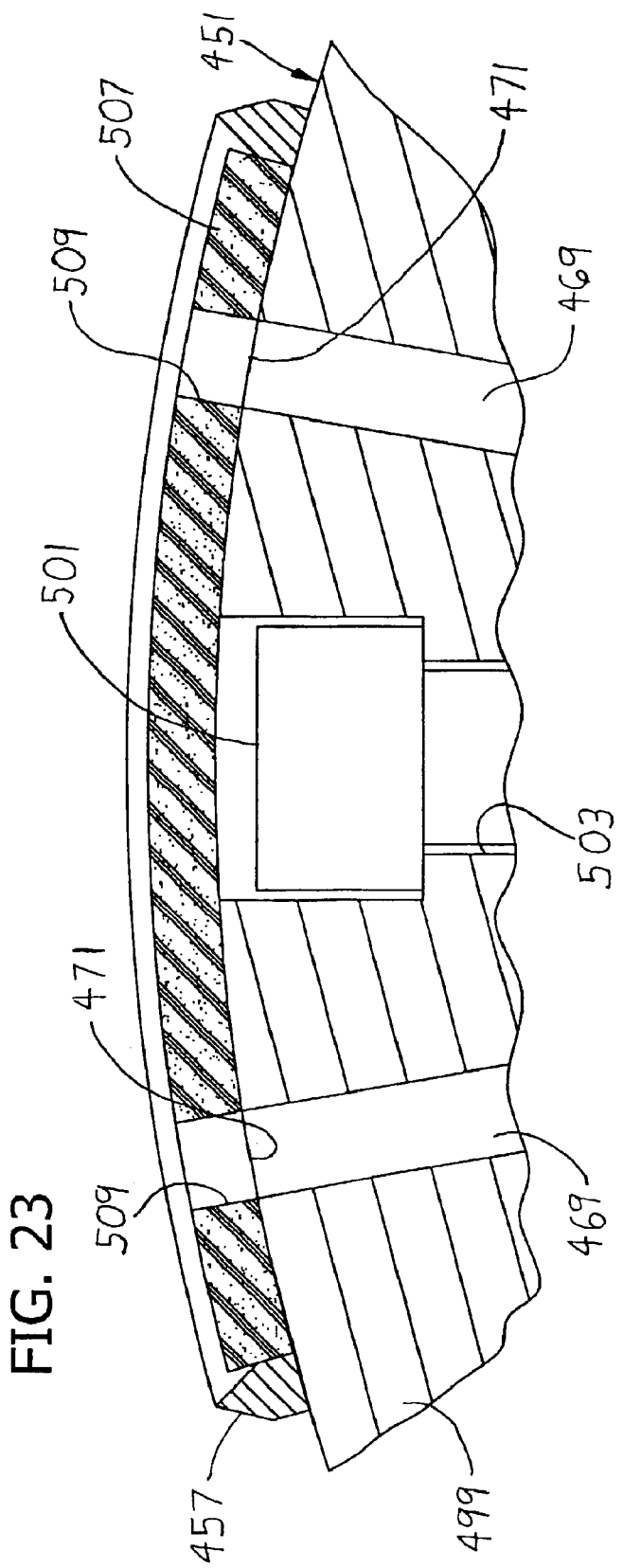
FIG. 23 is a partial sectional view showing a compressible insert in a cutting blade on the knife roll of FIG. 21.

Referring to FIGS. 20 and 21, the body 465 of the knife roll 451 may be of multi-piece construction, comprising a shaft 497 surrounded by a sleeve 499 fabricated as a plurality of arcuate segments (e.g., 3 such segments 499 A–C are illustrated in FIG. 20) affixed to the shaft by suitable fasteners 501 (FIG. 21) which extend through bores 503 in the sleeve 499 and are threaded into the shaft 497. In one embodiment, each segment 499 A–C carries two cutting dies or blades 457, each having an outline corresponding to the shape of the absorbent body 5 to be cut from the web. An insert 507 (FIG. 23) of a compressible but resilient material is secured to the outer surface of the body 465 of the knife roll 451 inside the perimeter of the blade 457, as by a suitable adhesive. The insert 507 may be an adhesive-backed body of cross-linked polyethylene foam, for example, having a tensile strength of 44 to 55 psi and a compression such that the material deflects 25% at a pressure of 12.7 to 15.5 psi. Such a foam is commercially available under the trademark "Volara" from McMaster-Carr Supply Company of Chicago, Ill. In its relaxed (uncompressed) condition or state, as shown in FIG. 23, the insert 507 projects out from the surface of the knife roll 451, preferably a distance slightly less than the height of the cutting blade 457. For example, for a cutting blade 457 having an overall height of 0.19 in., the insert 507 may project out a distance of 0.125 in. The insert 507 is porous (due either to the porous nature of the insert material or to holes 509 made in the insert) to provide for the transfer of vacuum from the vacuum openings 471 in the surface of the knife roll 451 through the insert. When the web 417 of absorbent material passes through the cutting nip CN1, the insert 507 is compressed to permit cutting of the material by the blade 457. After the web passes through the cutting nip, the tendency of the insert 507 to expand to its relaxed state exerts a small outward pushing force on the absorbent body 5 cut by the cutting blade 457. This outward force assists in the clean separation of the absorbent body 5 from the web 417 and the transfer of the absorbent body to the first transfer cylinder 485 at the first transfer nip TN1.

Figure 24:
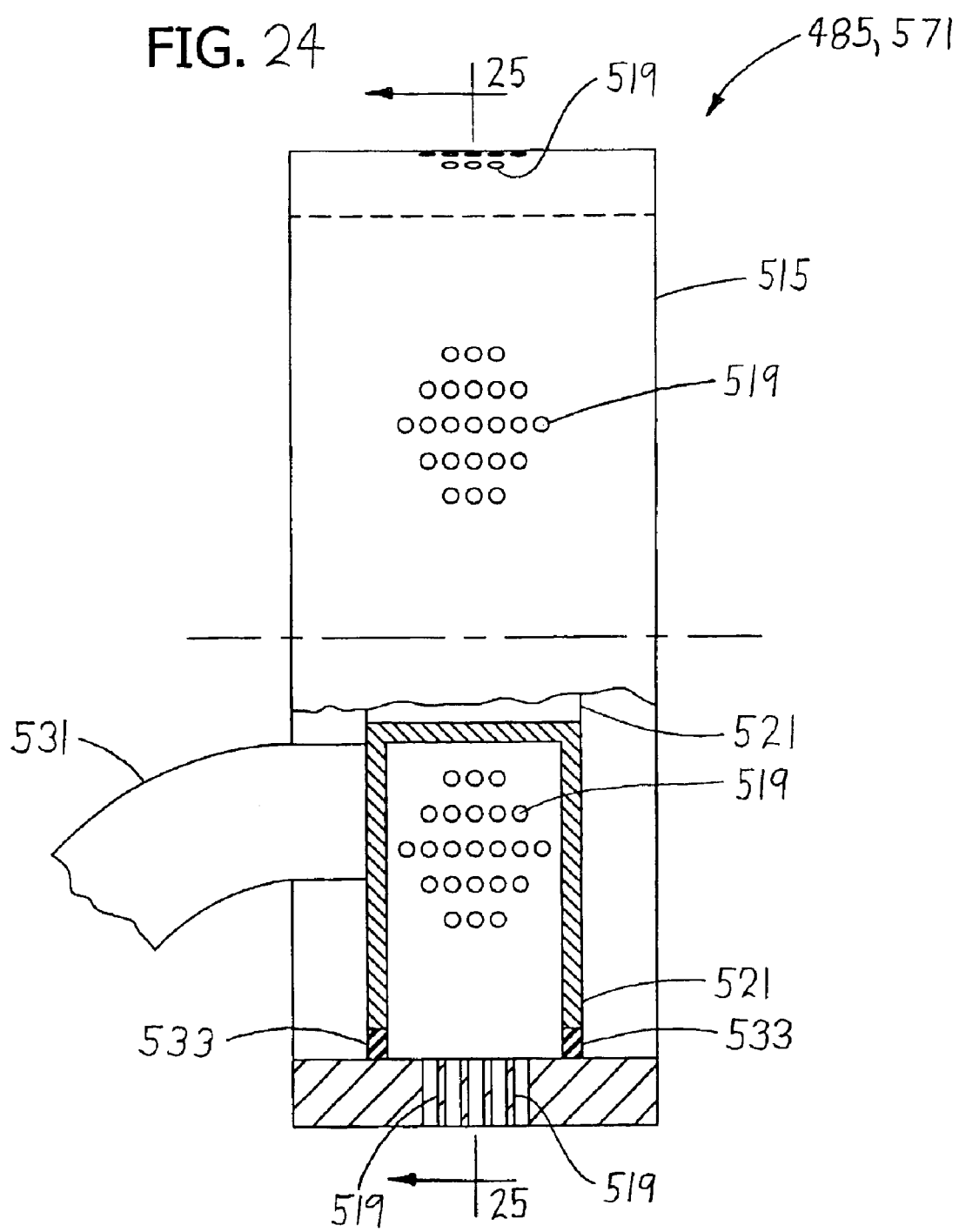
FIG. 24 is an elevation of a first transfer cylinder, with portions being broken away to show a vacuum box inside the cylinder.
Figure 25:
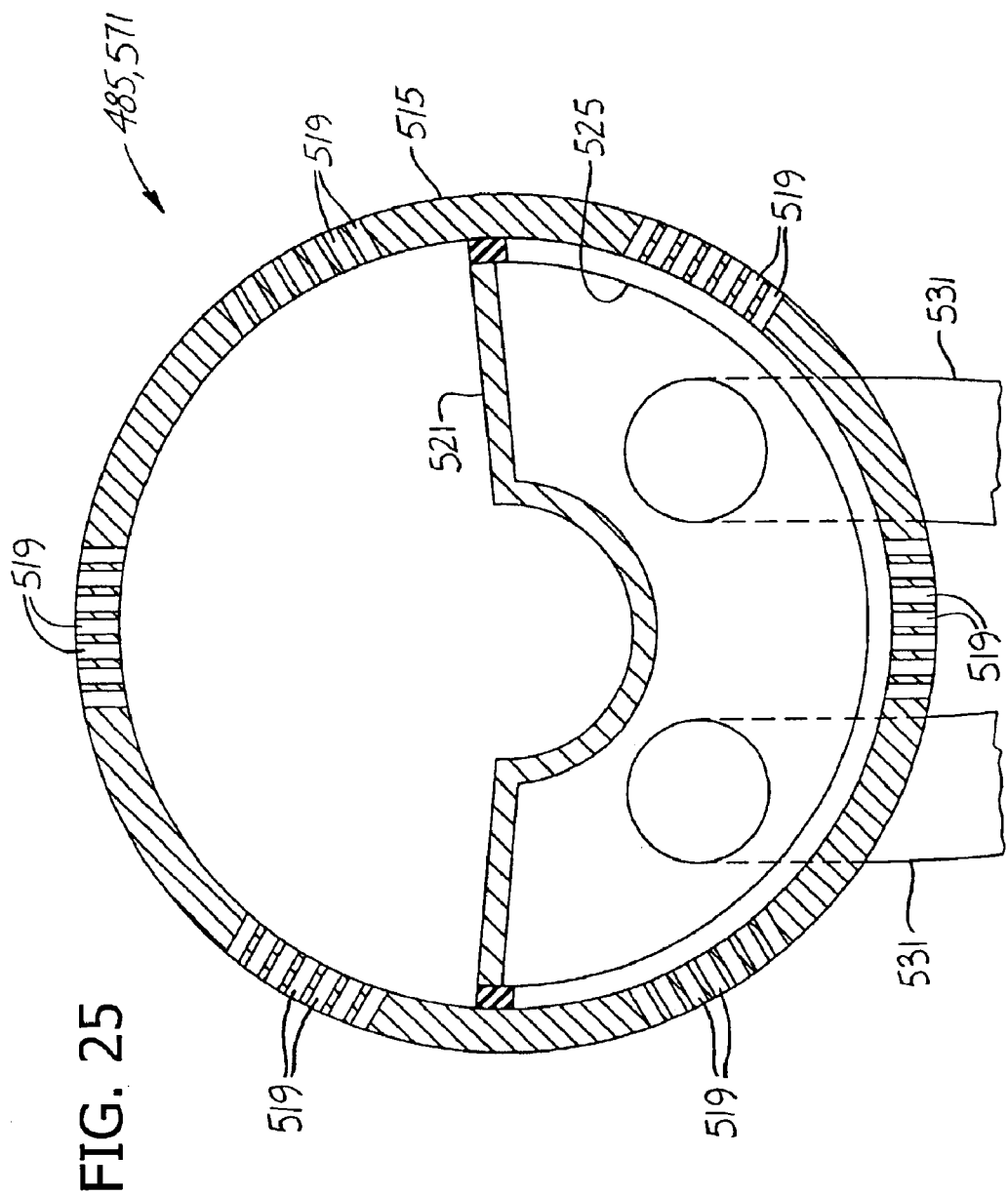
FIG. 25 is a section taken on line 25—25 of FIG. 24.

As shown in FIGS. 24 and 25, the first transfer cylinder 485 comprises a hollow body in the form of a drum 515 having a cylindric outer surface formed with a pattern of vacuum holes 519 generally corresponding to the shapes of absorbent bodies 5 transferred from the knife roll 451. A vacuum box 521 mounted in fixed position inside the drum 515 has an arcuate surface 525 defining a vacuum opening 527 positioned closely adjacent the inside wall 529 of the drum. The vacuum box 519 communicates by means of one or more air ducts 531 with the aforementioned vacuum system so that a negative pressure is generated in the vacuum box to draw air through the vacuum holes 519 in the outer surface of the drum as the drum rotates past the box. Seals 533 around the opening 527 in the vacuum box wipe against the inside wall 529 of the rotating drum 515 to seal against leakage of air. In the embodiment shown in FIG. 18, the vacuum box extends over more than about a 180° (e.g., about 190°) arcuate segment along the lower half of the drum from about the 9:00 position adjacent the first transfer nip TN1 to about a 3:00 position for transfer of the absorbent bodies 5 to the web sealing station 435, as will be described. The vacuum holes 519 in the first transfer cylinder 485 are located and arranged such that absorbent bodies 5 transferred to the first transfer cylinder 485 at the first transfer nip TN1 are vacuum gripped and held in precise position on the transfer cylinder as it rotates in a counterclockwise direction from the nip TN1 to about the 3:00 position. An exemplary pattern of vacuum holes 519 is illustrated in FIG. 24.

In the embodiment shown in FIG. 18, the web sealing station 435 includes sealing apparatus comprising, in one embodiment, a pair of opposing sealing rolls 541, 543 defining a sealing nip SN, one such roll (541) being shown as a lower sealing roll and the other as an upper roll. The upper sealing roll 543 has a smooth, uninterrupted cylindrical surface and is mounted in the same manner as the anvil roll 453 at the first cutting section 431, a power cylinder 547 being provided for this purpose. The lower sealing roll 541 is mounted for rotation in a fixed vertical position and defines a second transfer nip TN2 with the first transfer cylinder 485. The lower sealing roll 541 has a construction similar the knife roll 451, except that the body of the roll has a smooth cylindrical outer surface 551 (FIGS. 26 and 27) formed with a pattern of recesses or pockets 553 therein which are sized and shaped for receiving the absorbent bodies 5 transferred from the first transfer cylinder 485. Each pocket 553 has an outline which is slightly oversize relative to the outline of an absorbent body 5. The pocket 553 has a depth (i.e., in the Z direction) slightly greater than the depth of the absorbent body 5 so that the absorbent body is not compressed at the sealing nip SN. Alternatively, the depth of the pocket 553 can be made less than the thickness of the absorbent body 5 to provide for some compression of the absorbent body at the sealing nip, if desired.

Figure 26:
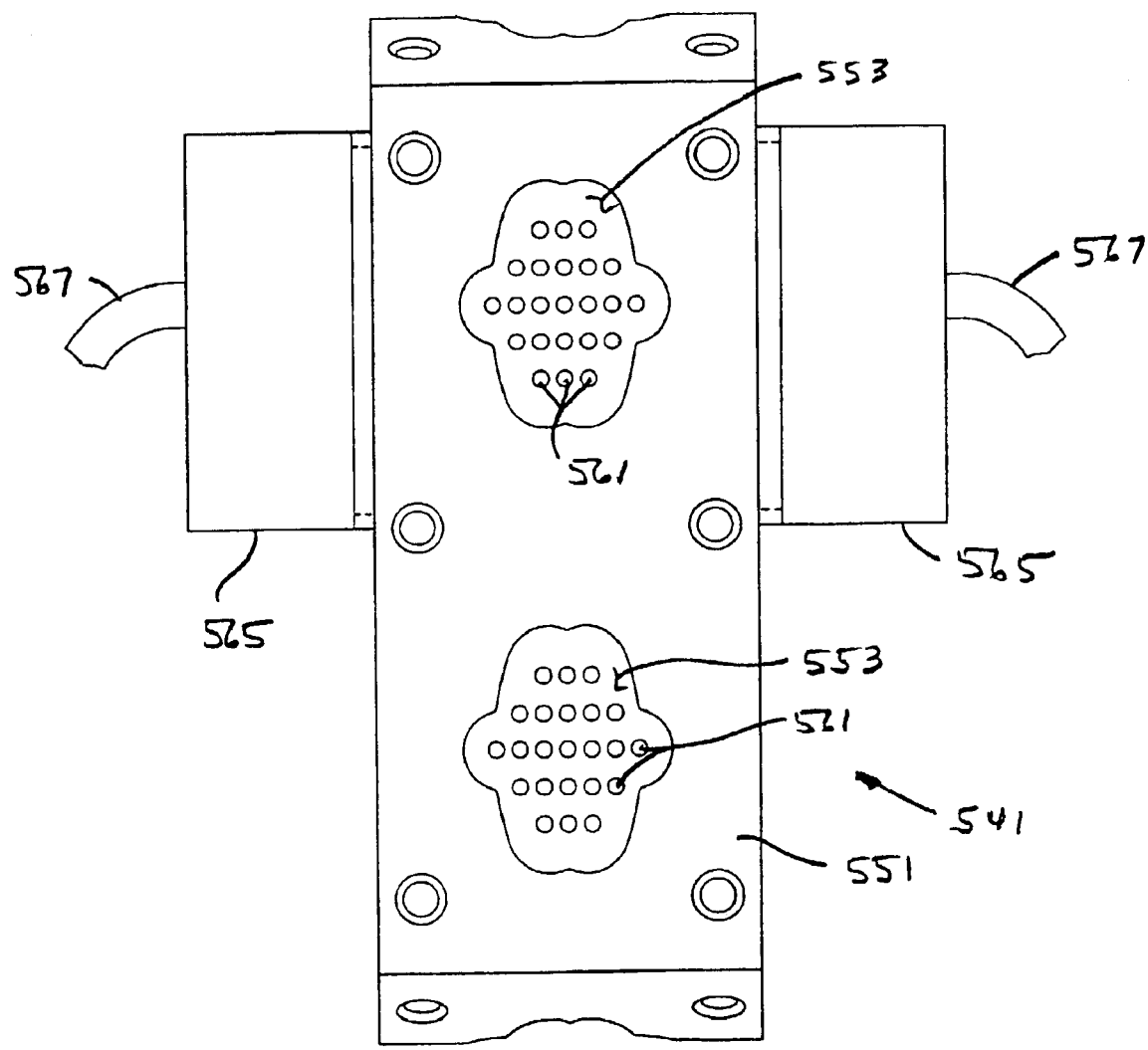
FIG. 26 is a elevation of a sealing roll in the pad making section.

The depth of the pocket 553 can be controlled by placing one or more perforated inserts of predetermined thickness in the pocket. Like the knife roll 451 at the first cutting station 431, the lower sealing roll 541 is also formed (e.g., machined) to have a series of axial and radial vacuum passages 557, 559 therein to create vacuum openings 561 in the outer surface 551 of the roll. Also like the knife roll 451, vacuum boxes 565 are mounted adjacent opposite ends of the lower sealing roll 541 and are connected by air ducts 567 to the vacuum system for generating a vacuum at the vacuum openings 561 on the roll 541. FIG. 26 illustrates a pair of exemplary pockets 553 formed in the outer surface 551 of the lower sealing roll 541.

In the embodiment shown in FIG. 18, the vacuum boxes 565 at the ends of the lower sealing roll 541 extend over more than about a 180° (e.g., about 190°) arcuate segment along the upper half of the roll from about the 9:00 position adjacent the second transfer nip TN2 to about a 3:00 position for transfer of the absorbent bodies 5 and accompanying webs 7W, 9W to a downstream second transfer cylinder 571 defining a third transfer nip TN3 with the lower sealing roll 541. In an alternate embodiment, the vacuum boxes 565 at the ends of the lower sealing roll 541 extend over an arcuate segment along the upper portion of the roll from about the 9:00 position adjacent the second transfer nip TN2 to about a 12:00 position for transfer of the absorbent bodies 5 and accompanying webs. As will be more fully described below, the two sealing rolls 541, 543 function to apply the cover and baffle webs 7W, 9W from the unwind rolls 425, 427 to the absorbent bodies 5 to form the laminated web 437, and then to seal the laminated web for delivery to the third transfer nip TN3.

Apparatus for feeding the cover web 7W for lamination with the absorbent bodies is shown in FIG. 18. This apparatus comprises the unwind supply roll 425 of cover web 7W material, corresponding to the cover layer 7 of a final pad (e.g., pad 1), mounted on a shaft 575 driven by a variable speed motor (not shown). The speed of the motor is controlled so that the rate at which web 7W is fed from roll 425 closely matches the rate at which the blended-fiber web 417 is fed to the pad-making section 31. One aspect of this feed control involves a sensing device 581 downstream from the unwind roll 425 for sensing a change in web tension due, for example, to the decrease in roll diameter as web is fed from the roll, and for signaling the motor to speed up or slow down to maintain a substantially uniform tension in the web corresponding to the desired speed. In one embodiment, the sensing device 581 comprises a dancer bar 583 pivoted on the frame of the machine, a dancer roll 585 rotatable on the bar and in contact with the web 7W, and a potentiometer (not shown) for sensing movement of the bar as a result of changes in web tension. Other sensing devices can be used. The cover web 7W is directed by a series of idler rolls 589 to the lower sealing roll 541 where it is pulled through the second transfer nip TN2.

As the web is pulled through the nip, absorbent bodies 5 are transferred from the first transfer cylinder 485 to the lower sealing roll 541 in a position overlying the cover web 7W to laminate the absorbent bodies on the web and thus form a lamination. The cover web 7W is of an air and fluid-pervious material, so that both the web and the absorbent bodies are subject to the vacuum force applied by the vacuum openings 561 in the sealing roll 541 to hold the web and bodies in precise position on the lower sealing roll (see FIG. 19). Further, the pockets 553 in the outer surface 551 of the lower sealing roll 541 are positioned for receiving the absorbent bodies as they are transferred from the first transfer cylinder 485, the end result being that the cover web and absorbent bodies are held by the vacuum of the lower sealing roll in the pockets and held in this laminated condition for conveyance to the sealing nip SN.

Apparatus for feeding a baffle web 9W for lamination with the cover web 7W and absorbent bodies 5 is also shown in FIG. 18. This apparatus comprises the second unwind supply roll 427 of baffle web material 9W, corresponding to the baffle layer 9 of a final pad (assuming a baffle layer is included), mounted on a shaft 591 driven by a variable speed motor (not shown). The operation and control of this motor is similar to that of the first unwind roll 425 described above and will not be repeated. A web tension sensing device 595 similar to device 581 is provided downstream from the second unwind roll 427. A series of idler rolls 599 direct the baffle web 9W past an applicator 601 which functions, in one embodiment, to apply (e.g., spray) a suitable adhesive (e.g., hot-melt adhesive) to a face of the web 9W to be applied to the absorbent bodies 5 and at locations generally corresponding to the peripheral seal 11 of the final pad, as shown, for example, in FIG. 1. Other types of applicators, adhesives and/or sealing methods may be suitable. Additional idler rolls downstream from the applicator 601 direct the baffle web 9W to the sealing nip SN defined by the sealing rolls 541, 543, where the baffle web is applied over the face of each absorbent body 5 opposite the cover web 7W, with the adhesive on the baffle web facing the lower sealing roll.

As the lamination of webs 7W, 9W and absorbent bodies 5 pass through the sealing nip SN (FIG. 19), pressure is applied by the sealing rolls 541, 543 to bring the adhesive on the baffle web 9W into pressure contact with opposing surfaces of the cover web 7W to seal the cover and baffle webs together around each absorbent body 5. If a hot-melt adhesive system is used, the distance between the applicator 601 and the sealing nip SN should be such that, given the speed at which the baffle web 9W is fed forward, the adhesive is sufficiently heated at the sealing nip to form a proper seal. Alternatively, one or both of the sealing rolls 541, 543 may be heated (ultrasonically or otherwise) to form heat seals around the absorbent bodies.

Figure 19:
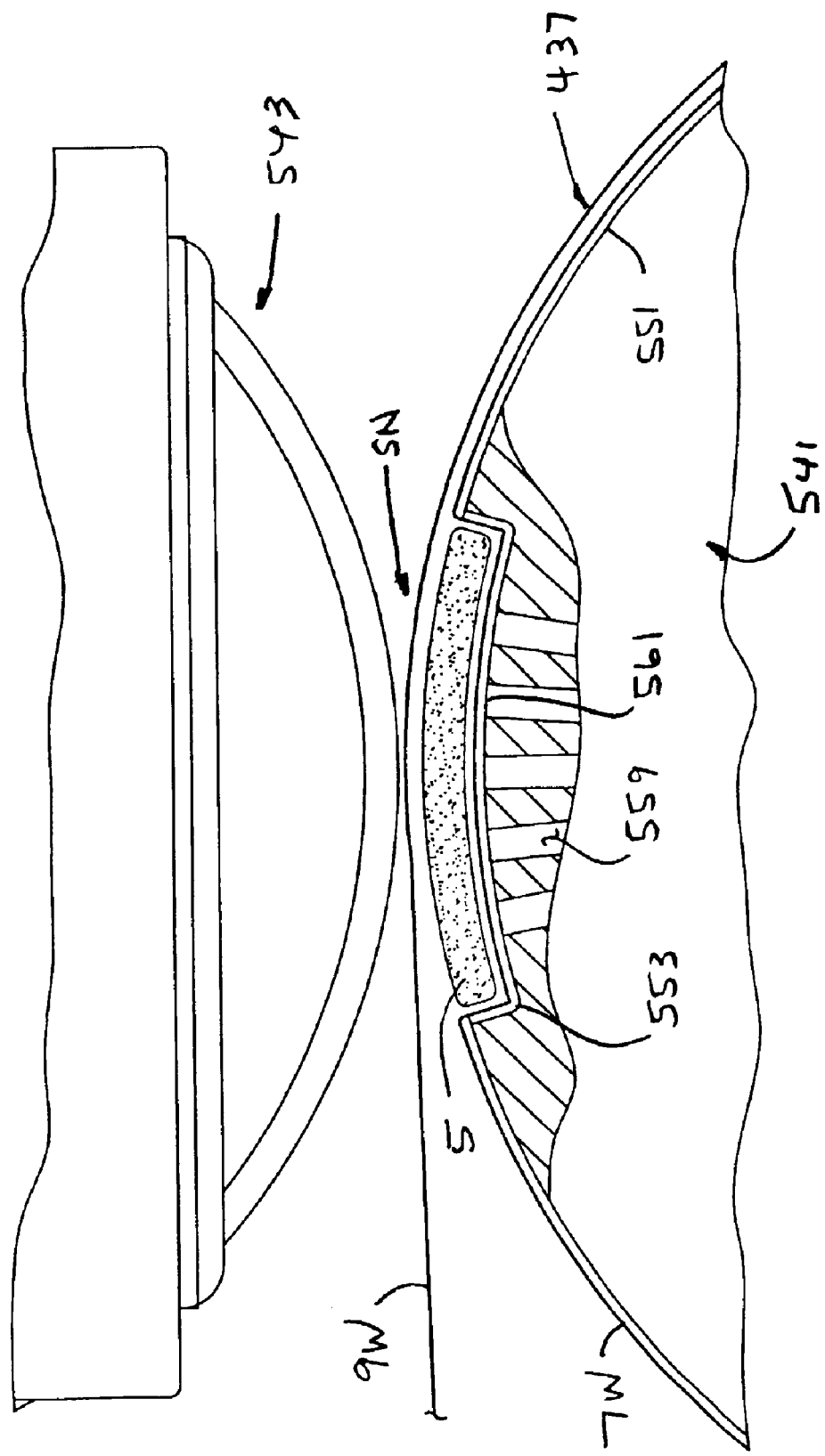
FIG. 19 is a schematic view showing a laminated web passing through a sealing nip.
Figure 27:
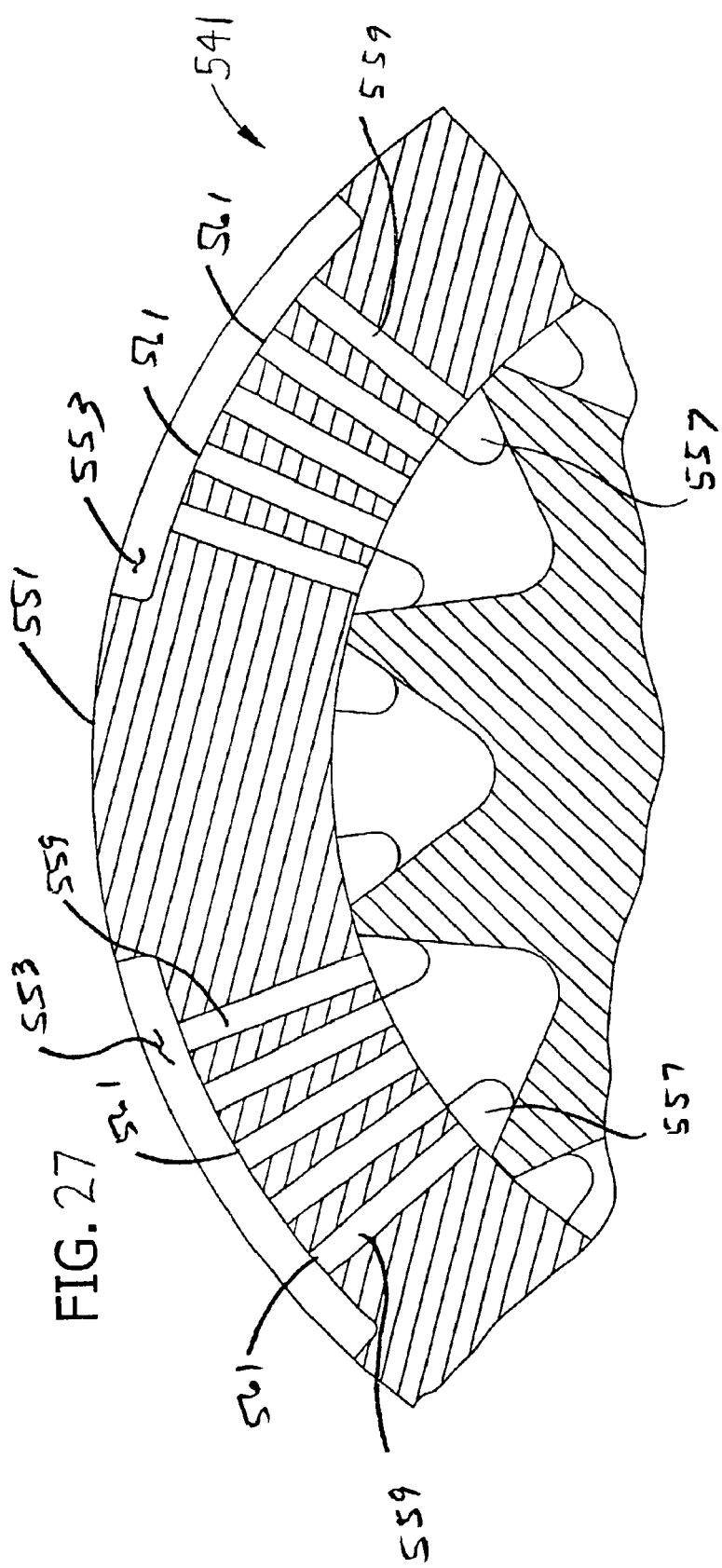
FIG. 27 is a partial sectional view showing the construction of the sealing roll of FIG. 26.

In the preferred embodiment of FIGS. 19, 26 and 27, the vacuum openings 561 in the lower seal roll 541 vacuum grip the sealed laminated web 537. As the sealing roll rotates, it exerts a pulling force on the web and conveys the web in a clockwise direction from the sealing nip SN to about a 3:00 position where the web is transferred to the second transfer cylinder 571 at the third transfer nip TN3. In one embodiment, the construction of the second transfer cylinder 571 is essentially identical to the construction of the first transfer cylinder 485. In the embodiment shown in FIG. 18, the vacuum box 603 inside the second transfer cylinder 571 extends over more than about a 180° (e.g., about 190°) arcuate segment along the lower half of the cylinder from about the 9:00 position adjacent the third transfer nip TN3 to about a 3:00 position for transfer of the sealed laminated web 537 to the second cutting station 441. The vacuum openings (not shown) in the second transfer cylinder 571 are located and arranged such that the web is vacuum gripped and pulled as the cylinder rotates in a counterclockwise direction, while maintaining the web in precise position. In an alternate embodiment, the second transfer cylinder 571 does not have a vacuum box or vacuum openings and the web is transferred to the second transfer cylinder 571 without using vacuum openings.

The second cutting station 441 includes second cutting apparatus comprising, in one embodiment, a second pair of opposing cutting rolls 607, 609 defining a second cutting nip CN2 where the sealed laminated web 537 is cut to form individual pads (e.g., pads 1). In this particular embodiment, the cutting rolls comprise a lower knife roll 607 and an upper anvil roll 609 similar to the two cutting rolls 451, 453 at the first cutting station 431. Preferably, the knife roll 607 at the second cutting station is a vacuum roll having a construction and operation similar to the first knife roll 451 at the first cutting station, except that as shown in FIG. 18, the vacuum boxes 611 at the ends of the roll 607 extend over more than about a 180° arcuate segment along the upper part of the knife roll from about the 9:00 position adjacent a fourth transfer nip TN4 between the knife roll 607 and the second transfer cylinder 571 to about a 3:00 position for transfer of the cut web to a third transfer cylinder 615 at a fifth transfer nip TN5 between the knife roll 607 and the cylinder 615. Alternately, the vacuum boxes 611 at the ends of the roll 607 extend over an arcuate segment along the upper part of the knife roll from about the 12:00 position adjacent the second cutting nip CN2 to about a 3:00 position for transfer of the cut web to the third transfer cylinder 615.

Figure 28:
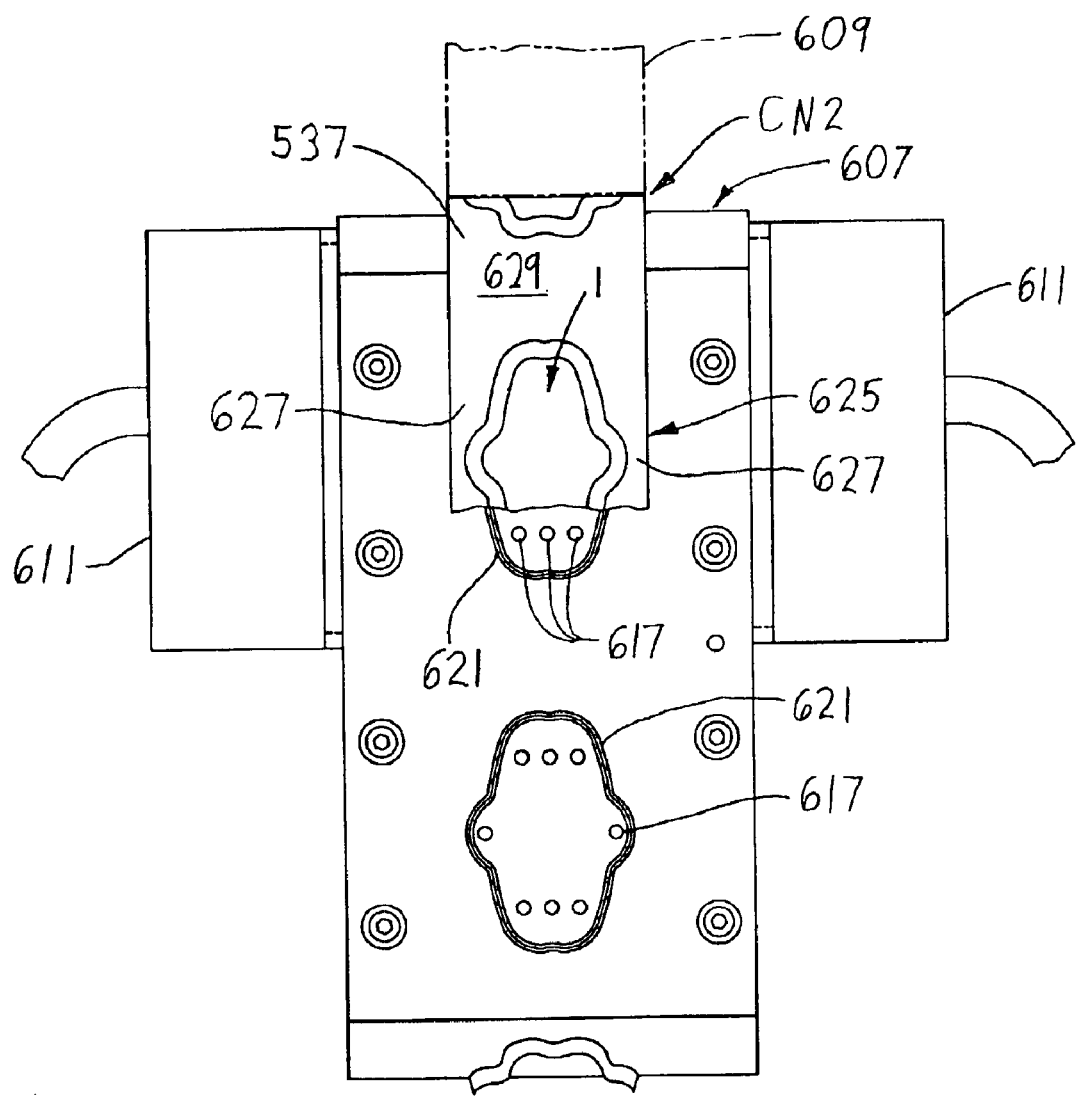
FIG. 28 is an elevation of a knife roll of a second cutting section in the pad making section.

As shown in FIG. 28, the vacuum openings 617 in the outer surface of the knife roll 607 at the second cutting station are arranged and located such that the laminated web 537 is vacuum gripped and held in precise position on the knife roll as the roll rotates in a clockwise direction to pull and convey the web from the fourth transfer nip TN4 to the second cutting nip CN2. The knife roll 607 carries cutter blades (or dies) 621 as shown in FIG. 28, for example, spaced at repeating intervals around the roll. The cutting blades 621 are configured so that, as the laminated web 537 travels through the second cutting nip CN2, the cover and baffle webs 7W, 9W are cut around the absorbent bodies 5 to form individual pads (e.g., interlabial pads 1). Because the cover and baffle webs are typically of a polymer material, the cutting blades 621 preferably have an interference fit with the anvil roll 609 (i.e., no gap or clearance) at the second cutting nip CN2 to ensure that the laminated web is cut completely through. (If different web materials are used, the clearance at CN2 may vary.) The cutting action forms individual pads 1 surrounded by remaining scrap portions 625 of the web, sometimes referred to as trim and typically having a ladder-like appearance. As shown in FIG. 28, the rails of the "ladder", indicated at 627, correspond to the unused extreme side edge margins of the web 537 and the rungs of the "ladder", indicated at 629, correspond to unused portions of the sealed areas of the laminated web. If required or desired, resilient inserts similar to the inserts 507 previously described may be placed inside the cutting blades 621. After cutting at the nip CN2, the pads 1 and trim 625 are vacuum conveyed by the knife roll 607 from the second cutting nip CN2 to the fifth transfer nip TN5 for transfer to the third transfer cylinder 615.

The third transfer cylinder 615 is essentially identical to the first and second transfer cylinders 485, 571 except that the vacuum box 635 (FIG. 29) inside the third transfer cylinder extends only along an arcuate segment of about 90° on the bottom part of the roll from about the 9:00 position at the fifth transfer nip TN5 to about the 6:00 position where the roll forms a sixth transfer nip TN6 with a vacuum conveyor 641 which conveys the pads to the folding section of the machine. Vacuum openings (not shown) in the outer cylindric surface of the third transfer cylinder 615 are located and arranged for vacuum gripping the pads 1 transferred from the knife roll 607 and holding them in predetermined positions relative to one another as the transfer cylinder 615 rotates in a counterclockwise direction to the sixth transfer TN6 nip. The gap between the third transfer cylinder 615 and the vacuum conveyor 641 at the nip TN6 should be no greater than (and preferably slightly less than) the thickness of the pads 1 to insure a clean separation of the pads from the trim 625 created at the second cutting nip CN2. The continuous strip of trim material 625 is removed preferably downstream from the sixth transfer nip TN6 and fed along a path (e.g., at 645 in FIG. 29) to an appropriate waste collector. The pads 1 are deposited on the conveyor 641 in an unfolded condition in which each pad lies flat on the conveyor in a pre-folding position in which the baffle web 9W faces up, the cover web 7W faces down, the major axis A1 of the pad extends generally parallel to the direction of feed, and the pad is generally centered on the conveyor 641 in a transverse CD direction with respect to the conveyor.

To maintain the various cutting rolls, sealing rolls, and transfer cylinders in timed relationship with one another, they are preferably driven by a common drive mechanism. This mechanism includes a drive motor and a drive train connecting the motor to the various rolls and cylinders. The drive train may comprise a series of timing belts and pulleys, for example, or a series of gears or other drive elements, as will be understood by those skilled in this field.

In the embodiment shown in the drawings, the axial length of each of the cutting rolls, sealing rolls and transfer cylinders is sufficient to accommodate only one lane of the absorbent bodies and pads. However, it will be understood that for higher throughput, additional lanes can be established by using wider rolls and cylinders, with accompanying modifications to associated equipment.

Figure 30:
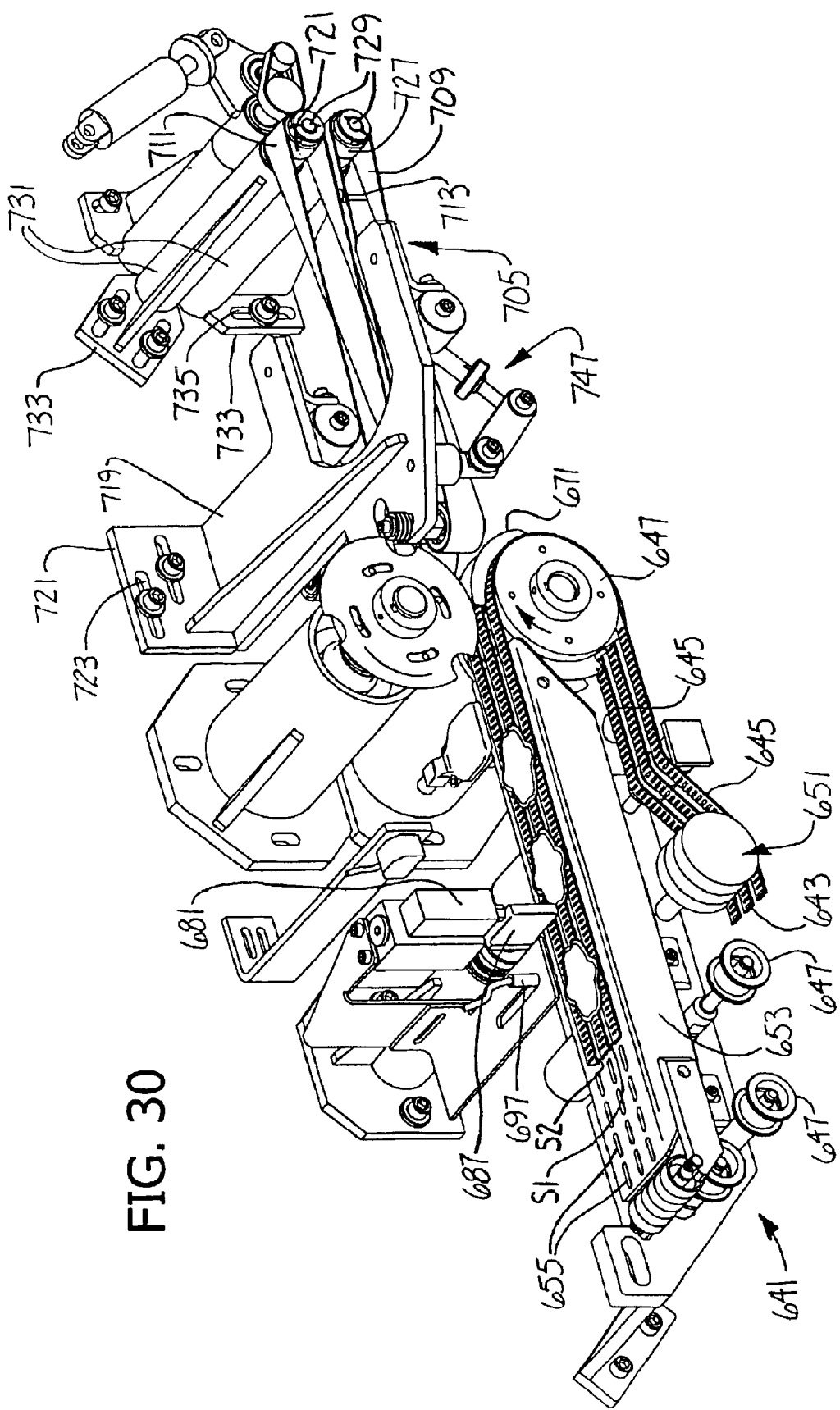
FIG. 30 is a perspective of apparatus of the folding section.

The vacuum conveyor 641 for conveying pads 1 to the folding section 33 comprises, in one embodiment (FIG. 30), three endless vacuum belts, namely, a center belt 643 and a pair of side belts 645 trained around rollers 647 to have generally horizontal, generally parallel, generally co-planar upper reaches spaced from one another to define first and second slots S1, S2. (FIGS. 30 and 32) The belts are perforated and relatively narrow, the overall width of the conveyor being not substantially greater than the width of an unfolded pad 1 carried by the conveyor so that the side belts 645 support respective side sections 1A, 1B of the pad and the center belt 643 supports the center section of the pad. The belts are preferably driven by a common drive 651 (FIG. 30). A vacuum box 653 having vacuum openings 655 in its upper surface is mounted immediately below the upper reaches of the conveyor belts 643, 645 and communicates with a vacuum system by means of an air duct (not shown), the arrangement being such that a vacuum is generated at the perforations in the center and side belts to hold each pad in the stated pre-folded position for delivery to the folding station 33. Other means may be used for conveying the pads from the pad-making section 31 to the folding section 33.

Pads delivered to the folding station by the conveyor are folded by folding apparatus, generally designated 661. In one embodiment (FIGS. 31 and 32), this apparatus includes a hold-down member comprising a rotatable disc 663 mounted for rotation about a generally horizontal axis spaced above the vacuum conveyor 641 to define a gap 665 between the peripheral edge of the disk and the upper reach of the center belt 643. The hold-down disk 663 preferably rotates in the same direction as the conveyance of the pads and at about the same speed, and it contacts each pad to hold it down against the center belt 643 as the pad is conveyed through the gap 665 and folded.

Figure 31:
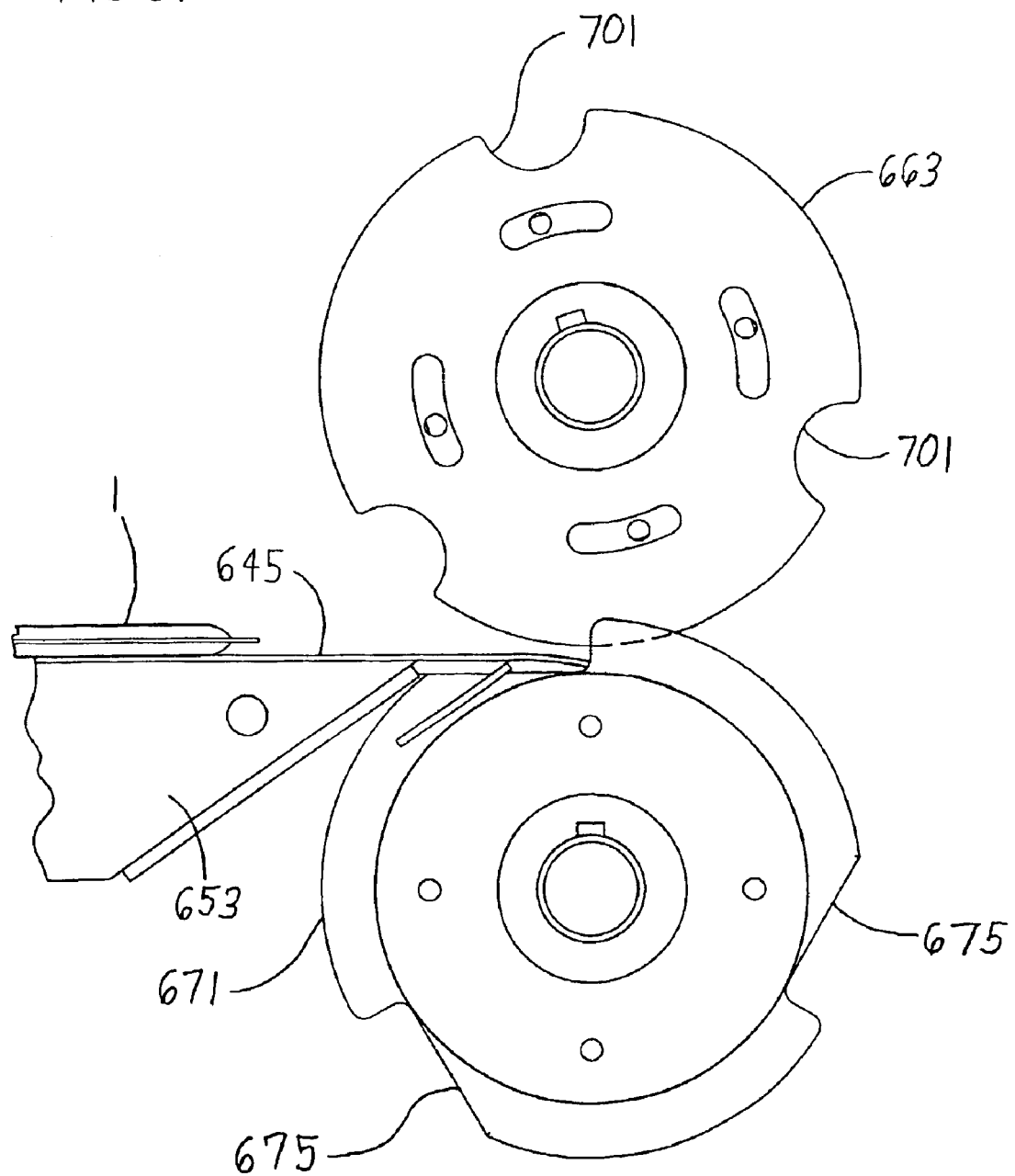
FIG. 31 is an elevation showing hold-down and folding disks of the folding section.
Figure 32:
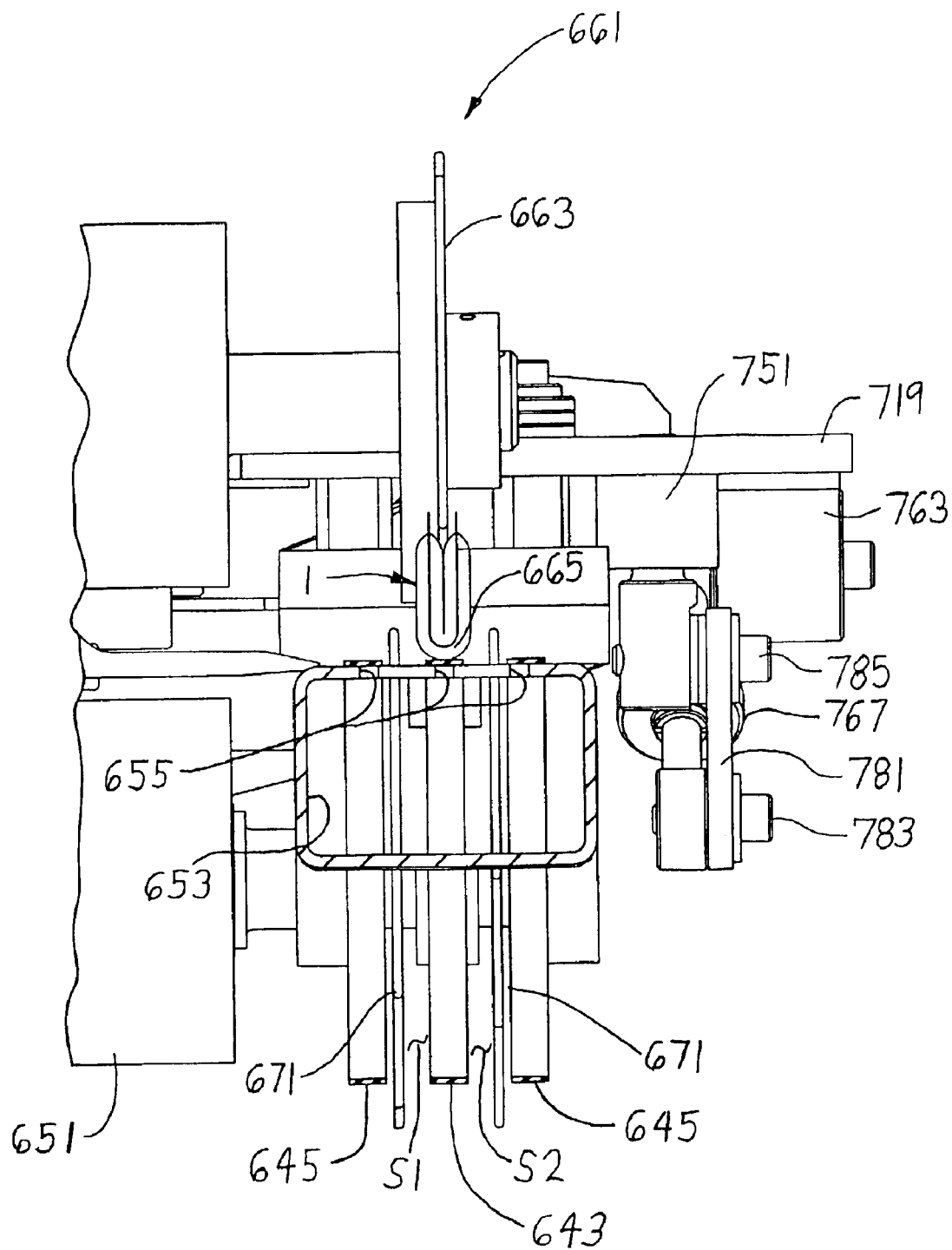
FIG. 32 is a an enlarged vertical section taken on line 32—32 of FIG. 29, showing a pad folded by the folding disks.

The folding apparatus 661 further comprises a plurality of folders comprising, in one embodiment, two folding disks 671 mounted on opposite sides of the hold-down disc for rotation about a horizontal axis spaced below the upper reaches of the belts 643, 645. As shown in FIG. 31, each folding disk 671 is formed with ramps 675 at spaced intervals around its peripheral edge. The ramps 675 on the two disks 671 are adapted to project up through respective slots S1, S2 between the belts 643, 645 and to contact the side sections of the pads 1A, 1B being conveyed as they pass below the hold-down disk 663. The folding discs 671 preferably rotate in the same direction as the hold-down disc 663 so that a respective pair of ramps 675 on the two folding disks contact each pad as it passes through the gap and fold the side sections 1A, 1B up to a position in which they face one another, as shown in FIGS. 4 and 32.

Figure 33:
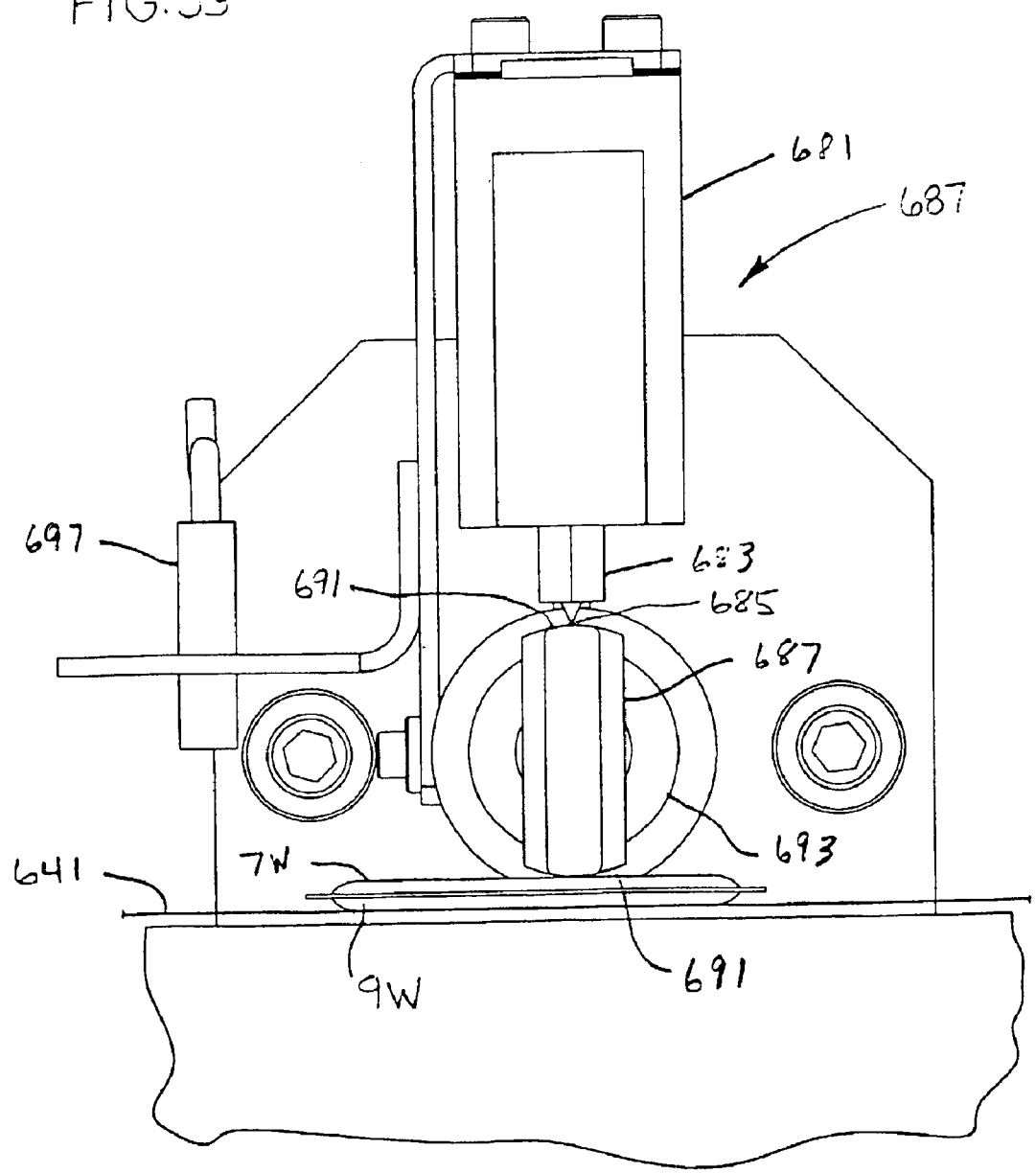
FIG. 33 is an elevation of an adhesive applicator in the folding section.

Optionally, adhesive may be applied to each pad 1 at an appropriate location on the pad (e.g., spot 679 in FIGS. 1 and 3) before it is folded. One embodiment of this option is shown in FIGS. 30 and 33 as comprising a glue dispenser 681 having a nozzle 683 for dispensing a metered amount of adhesive (e.g., in bead form) onto an applicator 687 positioned immediately above the conveyor 641. In the illustrated embodiment, the applicator 687 is generally rectangular in shape and, in the orientation shown, has relatively narrow upper and lower edges 691 for receiving adhesive from the nozzle 683 of the dispenser 681.

The applicator 687 is rotatable by a driven shaft 693 to rotate in timed relation to the movement of the pads 1 on the conveyor 641 to apply a small area of adhesive to the upper surface of each pad at an appropriate location as the pad passes beneath the lower edge 691 of the applicator carrying the adhesive (see FIG. 33). Preferably, the speed of the applicator 687 at its upper and lower edges 691 generally corresponds with the speed of conveyor 641. The dispenser 681 can operate intermittently in timed relation to the driven shaft 693 to deliver discrete quantities of adhesive to the upper edge 691 of the applicator 687 as the lower edge is applying glue to a pad below, or the dispenser can operate continuously to deliver a continuous bead of adhesive from the nozzle 683 that is picked up by the upper edge of the applicator as it moves through the bead.

Alternately, the glue dispenser 681 is positioned such that the nozzle 683 for dispensing a metered amount of adhesive is located adjacent (e.g., about a distance less than the diameter of a bead of adhesive) to the pad 1. The dispenser 681 is intermittently actuated to apply adhesive directly to the product. Preferably, a vacuum force holds the pad to a consistent thickness as it passes the nozzle 683 on the conveyor 641. In one embodiment, a glue dispenser commercially available from Nordson Corporation of Westlake, Ohio is used. It will also be understood that adhesive may be applied by applicators which have other shapes and/or which operate in different ways. Operation of the dispenser and applicator is controlled by a sensor (e.g., a photocell 697) upstream from the dispenser 681 for sensing the presence (or lack of presence) of pads.

To accommodate the application of adhesive to the pads 1, the hold-down disk 663 has a series of openings (e.g., notches 701) extending inward from its outer edge at spaced intervals around the disc. The notches 701 are sized and located to permit the side sections 1A, 1B of each pad to contact one another at the location of the adhesive spot 679 during the folding process. The adhesive assists in maintaining each pad in its folded condition prior to wrapping of the pad and after the pad is removed from its wrapper for use.

After the pads 1 are folded, they are conveyed by a suitable conveyor mechanism, generally designated 705, in their folded condition to the packaging section 35 of the machine. In one embodiment (FIG. 34), the conveyor mechanism 705 comprises a pair of endless transport belts 709, 711 having spaced apart reaches defining a gap 713 for receiving pads 1 delivered from the vacuum conveyor 641 at the folding station 33. The gap 713 is sized such that the transport belts apply a compressive force to the pads sufficient to grip and carry them to the packaging section 35. In one embodiment, the belts 709, 711 are twisted 90 degrees so that they receive the folded pads 1 in a generally vertical orientation and then rotate the pads 90 degrees for delivery to the packaging section 35 in a generally horizontal orientation.

The two transport belts 709, 711 have upstream ends trained around a pair of spaced apart generally vertical rollers 717 (FIG. 34) rotatably mounted on a generally horizontal support plate 719 carried by a bracket 721 with horizontal slots 723 affixed to the frame of the machine, and downstream ends trained around a pair of generally horizontal rollers 727 rotatably mounted on shafts 729 journalled for rotation in bearing housings 731 mounted on two brackets 733 with slots 735 affixed to the frame. Preferably, the shafts 723 carry sprockets connected to a suitable variable speed motor (not shown) by a timing belt for rotation of the shafts by the motor. The slots 723, 735 in the various brackets 721, 733 allow the positions of the belts 709, 711 to be adjusted in vertical and horizontal directions, as needed.

The vertical rollers 717 at the upstream ends of the belts 709, 711 are secured by threaded fasteners 741 received in transversely extending slots 743 in the support plate 719, the fasteners being movable in the slots to allow the spacing between the two belts to be adjusted. A pair of belt guide assemblies, each generally designated 747, maintain the upstream ends of the belts 709, 711 in proper position on their respective vertical rollers 717. In the embodiment shown in FIG. 34, each assembly 747 comprises a guide roller 751 adapted for contact with a respective belt 709, 711, and a linkage mounting the guide roller 751 on the support plate 719.

In the illustrated embodiment, this linkage comprises an L-shaped angle bar 755 affixed to the underside of the support plate 719 by a threaded fastener (not shown) received in a slot 757 in a horizontal leg of the angle bar, an upper tubular arm 761 having a pivot connection 763 with a vertical leg of the angle bar, a lower arm 765 having a telescoping fit with respect to the upper arm 761, a locking collar 767 for securing the upper and lower arms in fixed longitudinal and rotational positions relative to one another, and a lever 781 having a pivot connection 783 at its lower end with the lower arm 765 and a pivot connection 785 at its upper end with a roller support 787 on which the guide roller 751 is rotatably mounted. This linkage enables the position of the guide roller 751 to be adjusted in at least three different dimensions, i.e., in a first dimension corresponding to the machine direction MD by using the slot 757 in the angle bar 755 to vary the position of the bar relative to the plate 719; in a second dimension corresponding to the Z direction by pivoting the upper and lower arms 761, 765 about pivot connection 763 to raise and lower the guide roller 751; and in a third dimension by rotating the lower arm 765 on its longitudinal axis relative to the upper arm 761 to swing the guide roller 751 to an angled position in which its axis of rotation is angled relative to a vertical plane.

By using one or more of these adjustments, the guide roller 751 can be positioned to contact its respective belt 709, 711 at any orientation necessary to prevent the belt from "walking" up or down on its respective vertical roller 717 and thus maintain the belt substantially centered on the roller. The spacing between the belts at their downstream ends can be varied by using the slots 735 in brackets 733 to adjust the position of the horizontal rollers 727. The downstream ends of the transport belts are positioned immediately adjacent the packaging section 35 for delivery of the pads to wrapping apparatus, generally designated 801.

Figure 29:
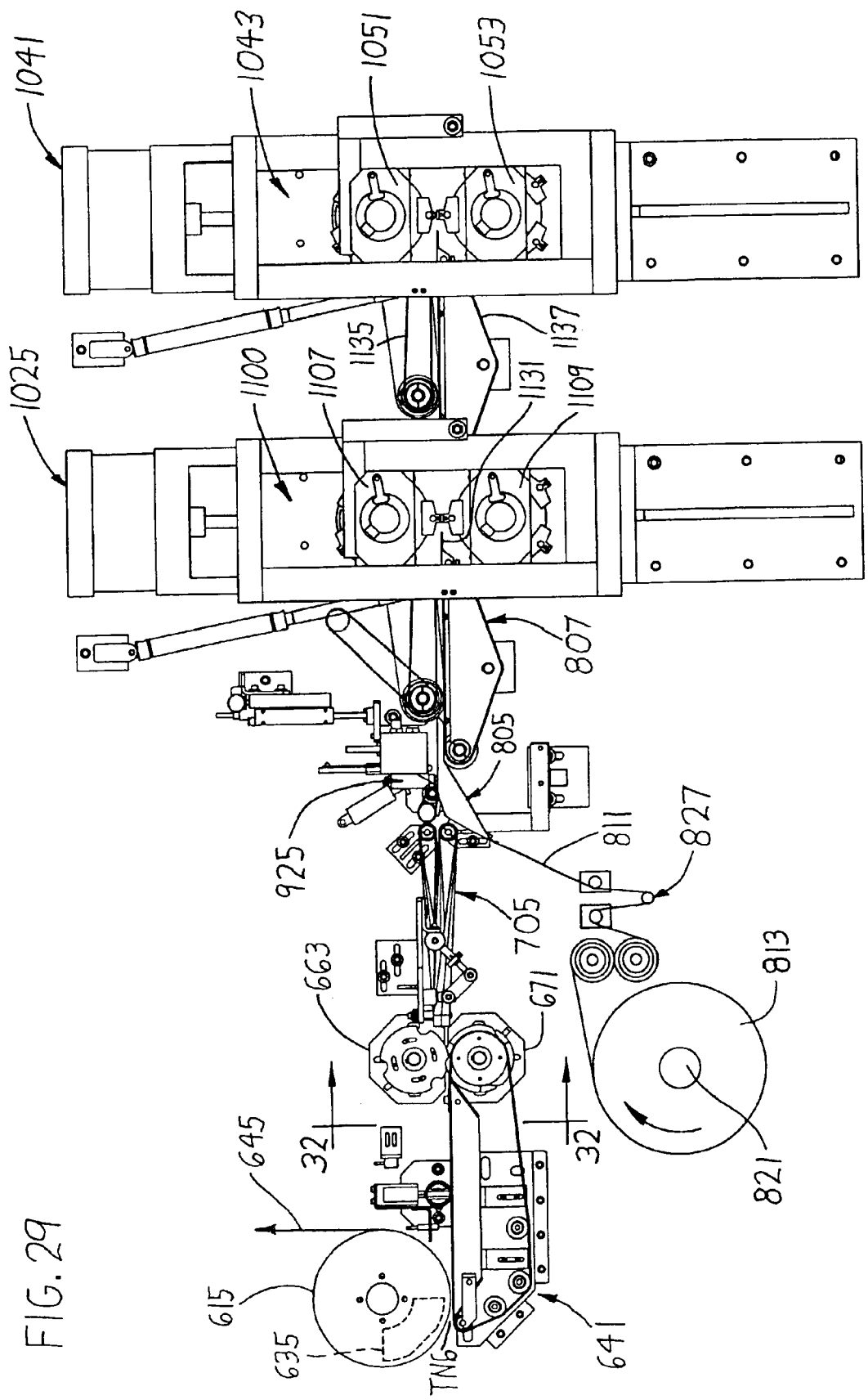
FIG. 29 is an elevation of apparatus of the folding section and packaging section.
Figure 35:
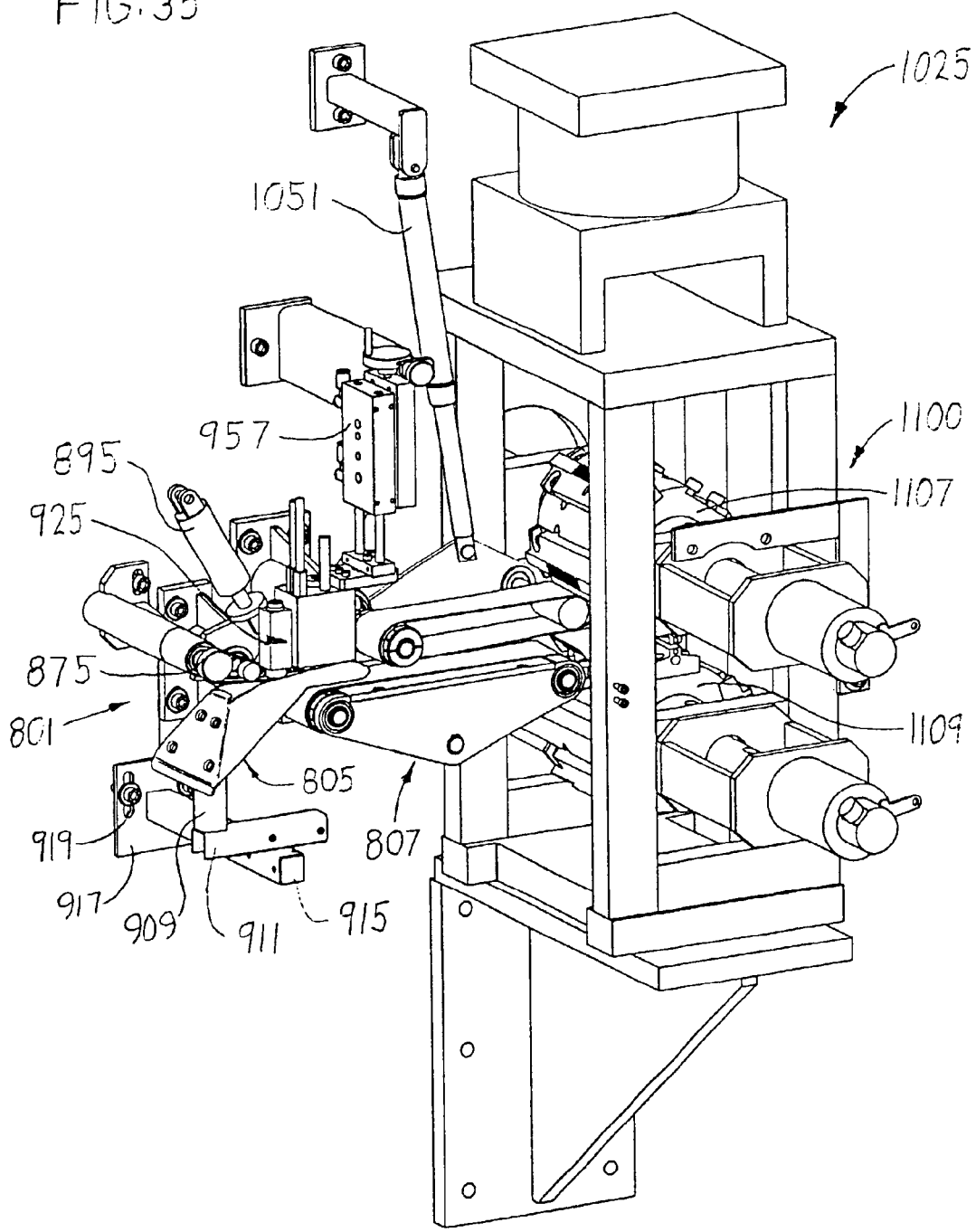
FIG. 35 is a perspective of apparatus of the packaging section.

Referring to FIGS. 29 and 35, the wrapping apparatus 801 includes a forming device, generally designated 805, for receiving pads delivered by the transport belts 709, 711, and web-pulling means generally designated 807 downstream from the forming device 805 for pulling a continuous web 811 of flexible wrapping material (e.g., polyethylene or other suitable material) from a supply roll 813 of such material past the forming device to wrap the pads 1 in a tube 815 of the material which, when later sealed and cut, will form wrappers for the pads. The supply roll of packaging material is supported by a shaft 821 driven by a variable speed motor (not shown) to control the speed at which the web is fed from the roll. The speed of the motor is controlled by a web-tension sensing device 827 similar to the sensing devices described earlier for the unwind rolls 425, 427. In the event the sensing device senses a change in web tension, it signals the motor to rotate the shaft 821 either slower or faster to maintain the speed at which the web 811 is pulled from the roll 813 substantially constant.

Referring to FIGS. 36–40, the forming device 805 comprises first and second web folding members 831, 833 having angled folding edges 831A, 833A adapted for contact by respective opposite side margins M1, M2 of the web 811 as the web is pulled past the folding edges (see FIG. 36), a web guide 837 for guiding the web toward the folding edges, and an opening 839 between the web guide and the folding edges adapted to be spanned by a central portion of the web as the web is pulled past the forming device. In one embodiment, the folding members comprise upper and lower folding plates or boards (also designated 831, 833) having opposing surfaces defining a relatively narrow gap 843 (FIG. 40) extending in the machine direction MD as the web is pulled over the forming device 805. The folding members 831, 833 also have spaced apart side walls 847 which flare down and out from their respective folding plates. The folding edges 831A, 833A at the upstream ends of the plates 831, 833 are angled in opposite directions relative to the direction of web travel and at a suitable angle relative to the direction of web travel, preferably in the range of from about 14° to about 20° and more preferably from about 16° to about 18°. The folding members may have configurations other than as described above.

Figure 37:
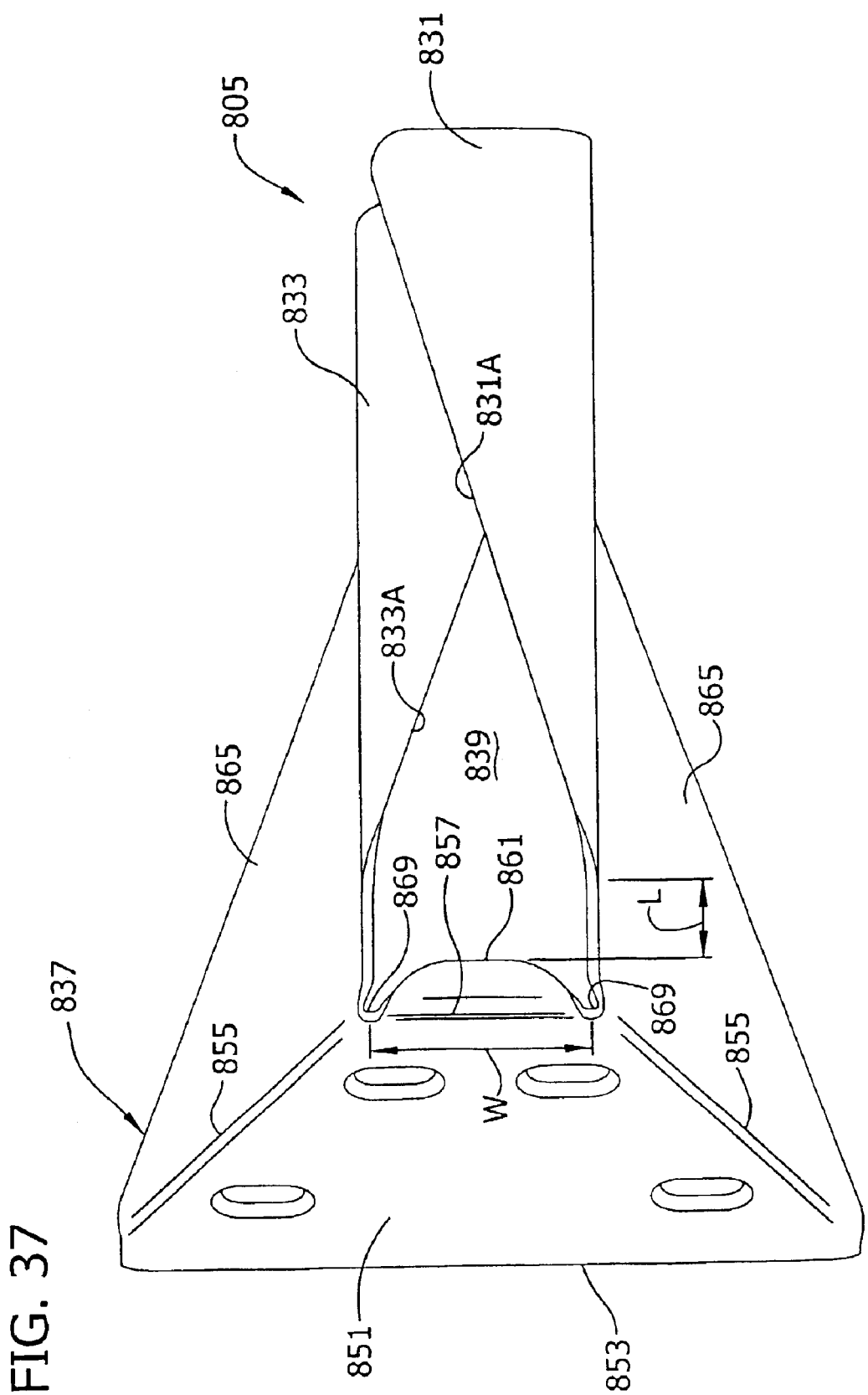
FIG. 37 is a top plan of the forming device.

The web guide 837 comprises, in the embodiment shown in FIG. 37, a generally triangular web contact surface or wall 851 having a base edge 853 and opposite side edges 855 which taper up to an apex 857. The wall 851 is inclined relative to the plane of the opening 839 and is positioned for contact by the web 811 of packaging material pulled from the supply roll 813. A tongue 861 extends from the apex 857 toward the opening 839. The tongue 861 is preferably either generally coplanar with the lower folding plate 833 or spaced below the folding plate a vertical distance less than the thickness of the pad. The web guide also has side walls 865 extending in a downstream direction from respective folding edges 855 to integral junctures with respective side walls 847 of the folding members. For economy, the web guide and folding members are preferably formed as a single piece of bent sheet metal (e.g., 14 gauge 304 stainless steel sheet) although they may be constructed as separate parts.

Figure 36:
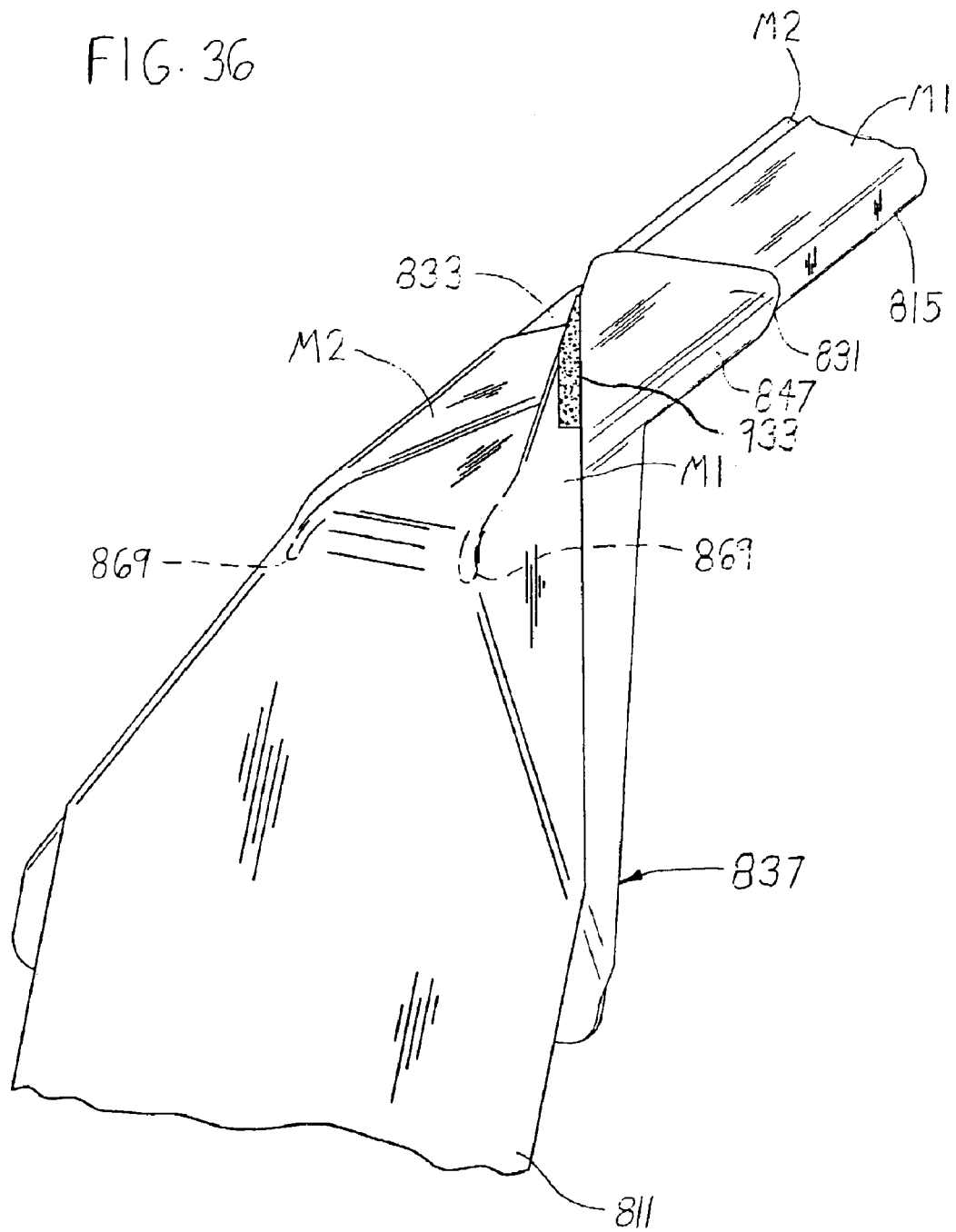
FIG. 36 is a perspective of a forming device for forming a web of material into a tube around pads delivered to the device.
Figure 38:
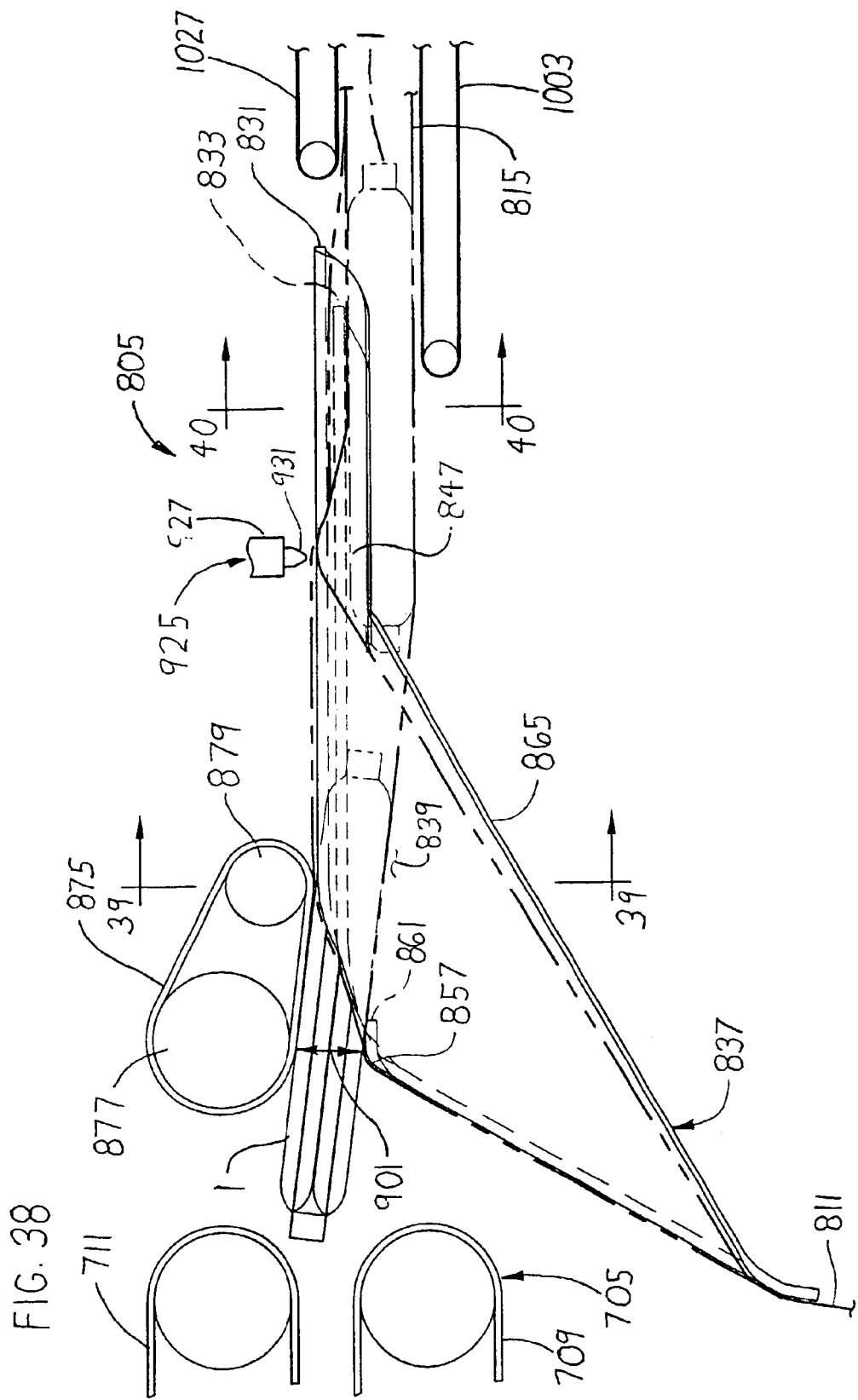
FIG. 38 is a side elevation of the forming device and associated components.

As shown in FIGS. 36 and 38, the tapered folding edges 855 of the web guide 837 serve to initiate the folding of the web 811 and to guide it across the opening 839 toward the folding boards 831, 833 for contact by the angled folding edges 831A, 833A. A pair of notches 869 extend down from the apex 857 of the wall 851 of the web guide on opposite sides of the tongue 861. Being under tension, the web 811 deforms down into these notches 869 as the web is pulled past the forming device 805.

Figure 41:
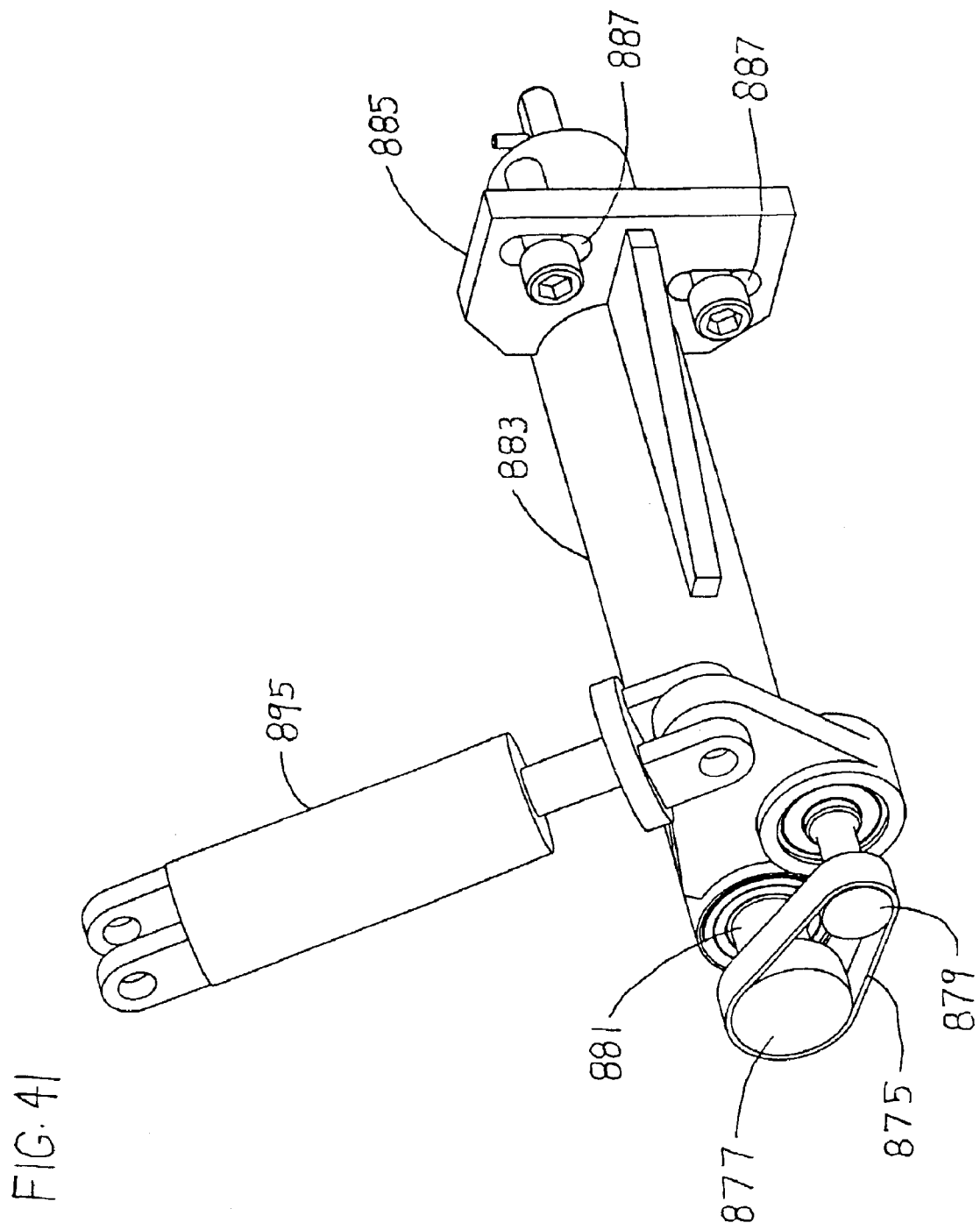
FIG. 41 is a perspective of an endless belt for applying a downward force on pads as they move across the forming device.

The wrapping apparatus 801 also preferably includes what may be referred to as a force-applying device which, in the preferred embodiment, comprises a relatively short narrow endless belt 875 extending over the forming device 805 generally along the central portion of the web 811. (The purpose of this belt will be described later.) The belt 875 is supported by a pair of rollers 877, 879, one or both of which are driven to move the belt 875 at the same speed as the web 811 moves past the forming device 805. In the embodiment shown in FIG. 41, the upstream roller 877 is mounted on a driven shaft 881 rotatable in a bearing housing 883 secured by a bracket 885 with slots 887 to the frame of the machine. The downstream roller 879 is rotatable in a bearing housing 891 carried by a support plate 893. A power actuator (e.g., power cylinder 895) is connected to the support plate 873 for pivoting the support plate and the downstream roller 877 relative to the bearing housing 883 to vary the position of the belt 875 as needed for maintenance and for adjustment relative to the forming device 805.

Referring to FIG. 38, the upstream end of the endless belt 875 is positioned above the web guide 837 to define a gap 901 for receiving pads from the transport conveyor 705. Pads fed one at a time into the gap 901 are carried by the moving web 811 and the belt 875 in the machine direction MD across the opening 839 and past the folding boards 831, 833. In the embodiment shown in the drawings, the upstream roller 877 of the belt 875 is disposed over the apex 857 and tongue 861 of the web guide 837, and the downstream roller 879 positioned generally over the opening 839. The lower reach of the belt 875 is inclined downward in the machine direction MD and forms an inclined surface which is positioned for contact by the pads. Thus, as each pad 1 moves past the tongue 861 and over the opening 839, it is forced down against the web and moved to a level where it will pass below the lower folding plate 833.

Figure 39:
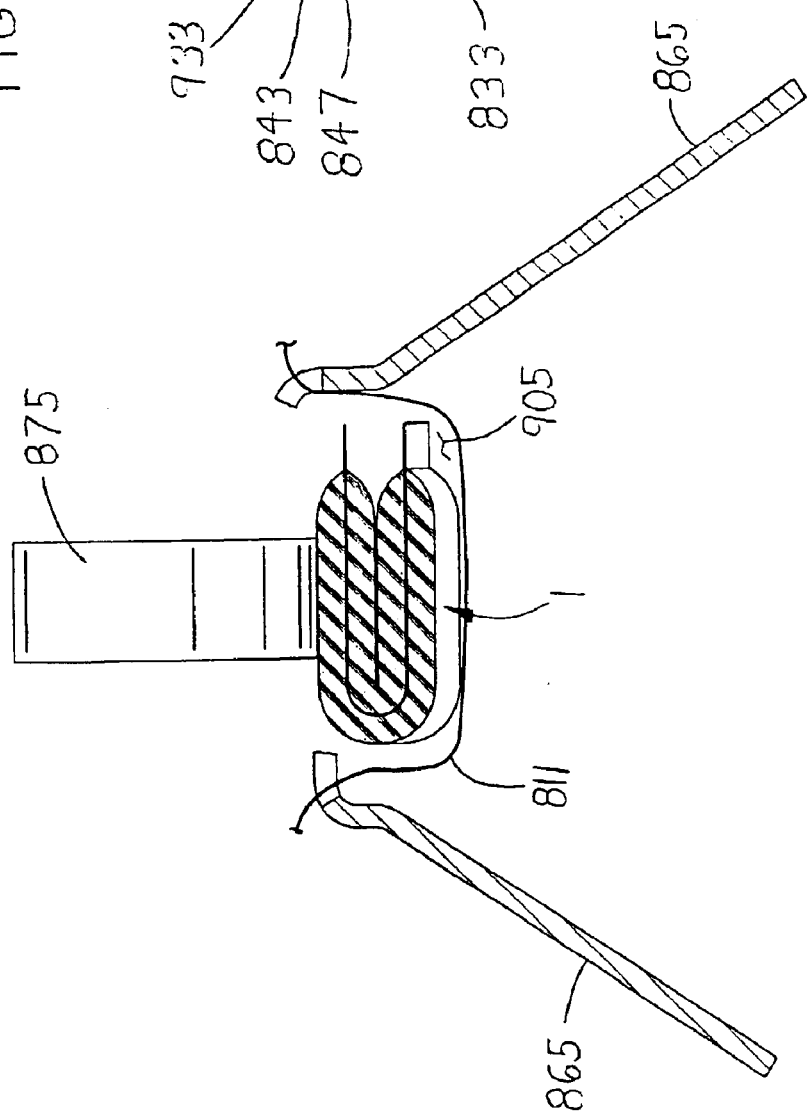
FIG. 39 is a vertical section taken on line 39—39 of FIG. 38.

This downward force causes the web in the area of the opening 839 to "cup" so that a pocket or depression 905 is formed in the web for cradling the pads (see FIG. 39). The cupping action is preferably accompanied by a resilient deformation or stretching of the web any, in a preferred embodiment, by a resilient compression of the pad, e.g., to a point where the pad has a compressed thickness in the range of 50–100% of the uncompressed thickness of the pad and more preferably about 95% or greater. As a result, the web 811 is tightly wrapped around the pads as the web is pulled past the folding edges 831A, 833A of the folding plates 831, 833 to form the aforementioned tube 815 around the pads. In addition to applying a downward force in Z direction, the friction between the belt 875 and the pads 1 subjects the pads to a pushing force in the machine direction MD to assist in the movement of the pads toward the folding boards.

Figure 38A:
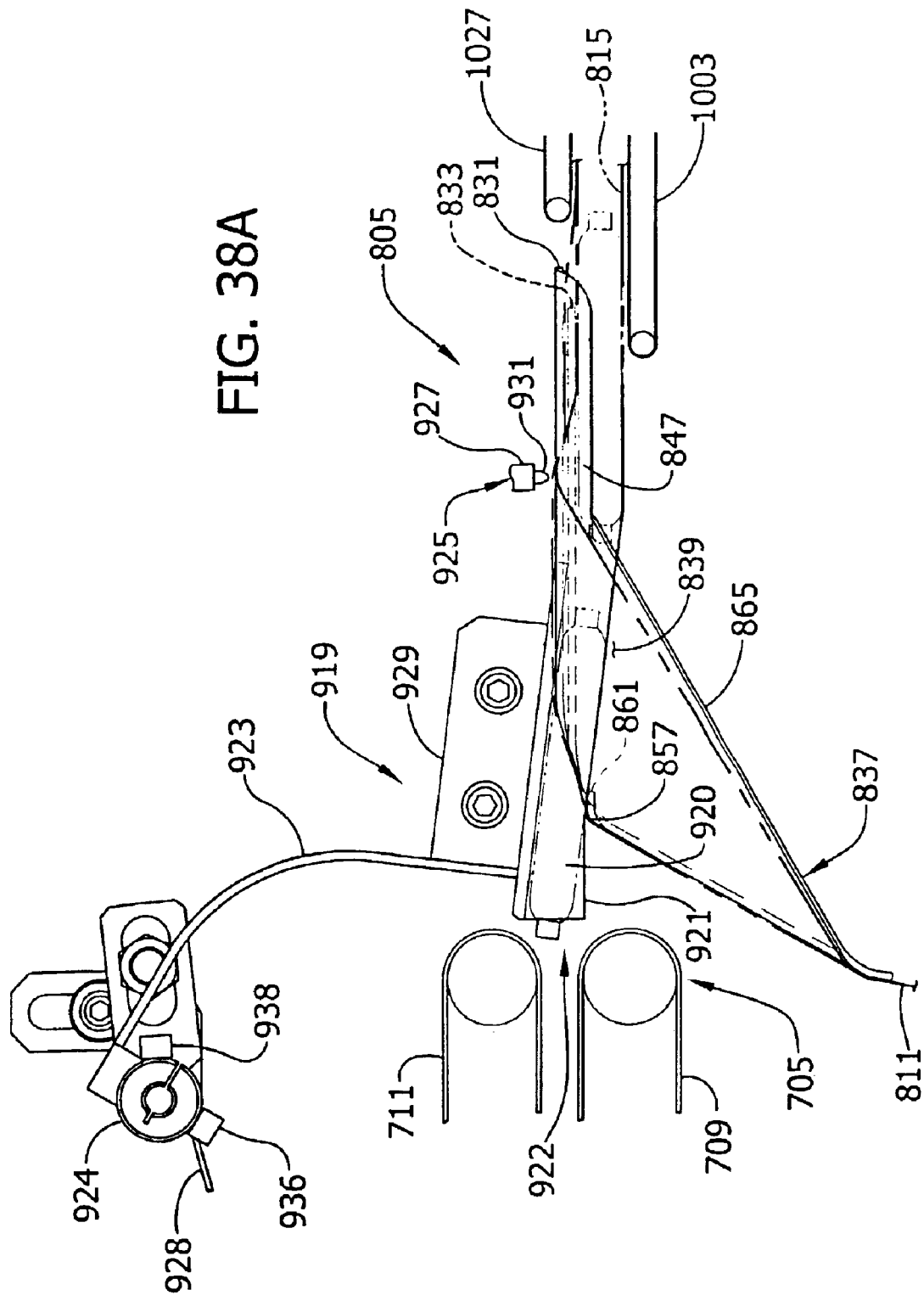
FIG. 38A is a side elevation of an alternate embodiment of the forming device and associated components.
Figure 38B:
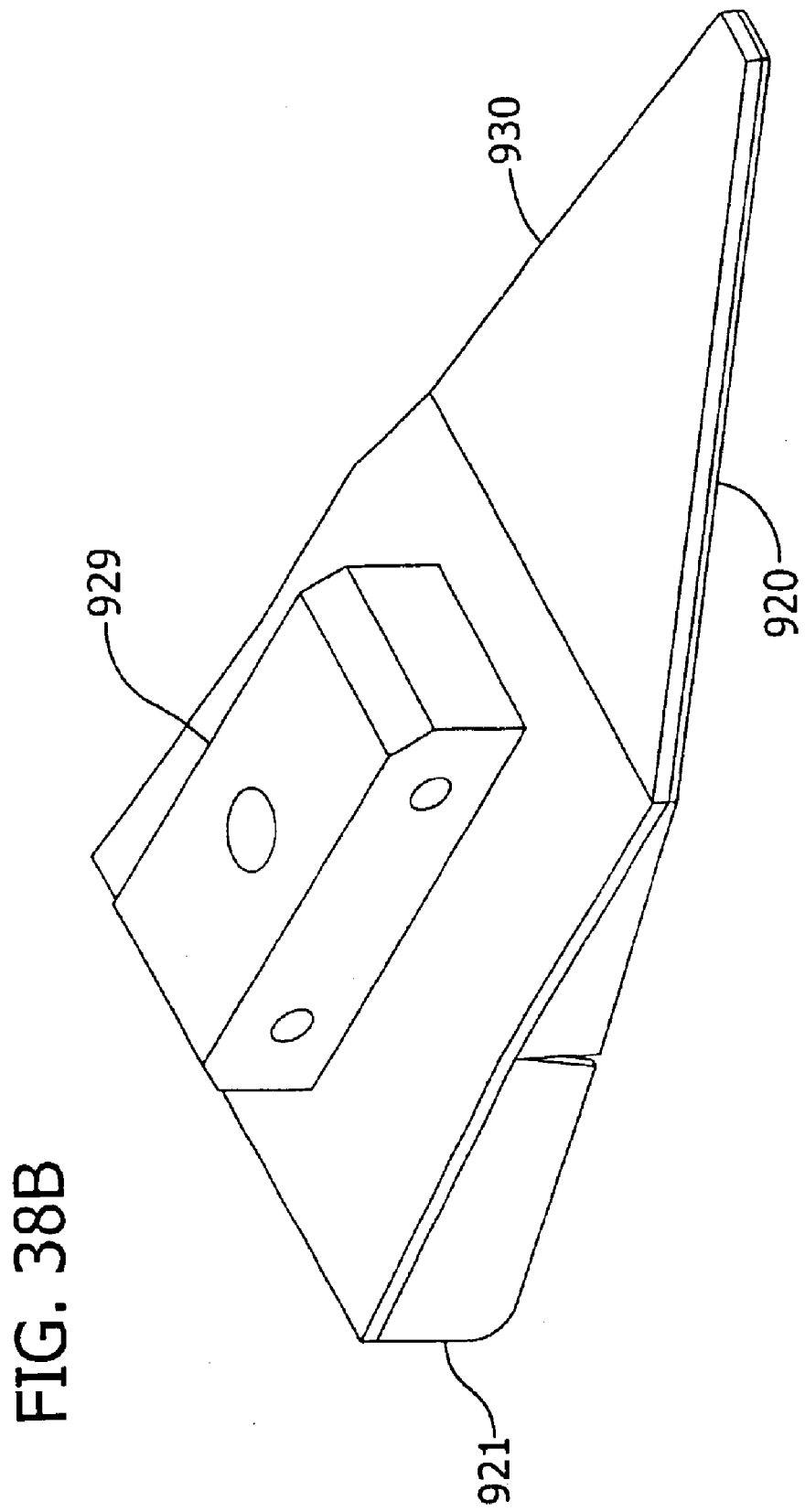
FIG. 38B is a perspective of a hold down plate for applying a downward force on pads as they move across the forming device.
Figure 38C:
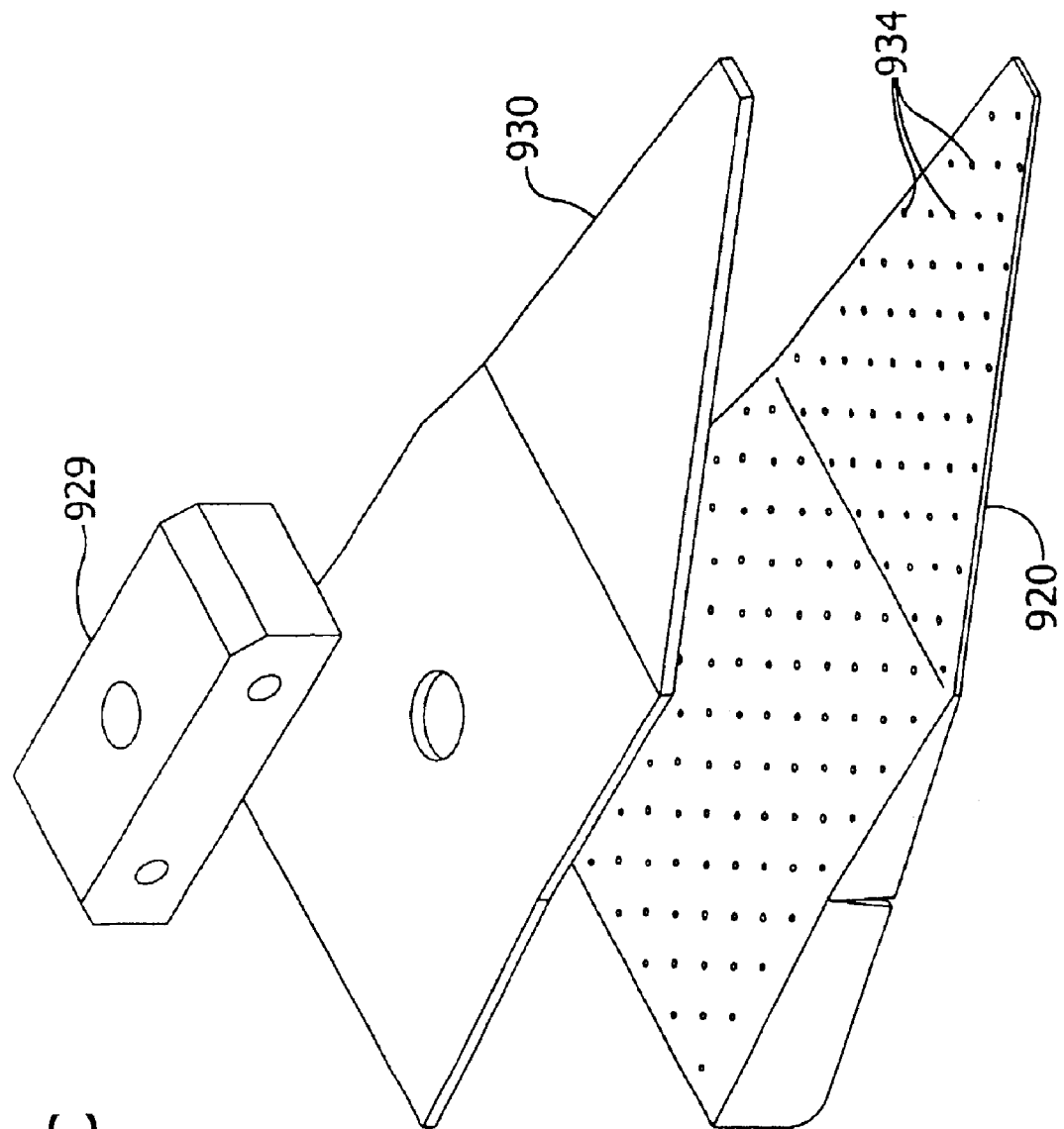
FIG. 38C is an exploded perspective of the hold down plate of FIG. 38B illustrating air holes in the hold down plate.

FIGS. 38A–38C illustrate an alternate force-applying device, generally designated 918, for applying a downward force on the pads. The device is positioned above the web guide 837 and comprises a hold down plate 920 having downwardly extending side flanges 921 which define a channel 922 for receiving pads from the transport conveyor 705. Pads fed one at a time into the channel 922 are carried by the moving web 811 in the machine direction MD across the opening 839 and past the folding boards 831, 833. In the embodiment shown in the drawings, the hold down plate 920 has a lower surface which is inclined downward in the machine direction MD and is positioned for contact by the pads. Thus, as each pad 1 moves past the tongue 861 and over the opening 839, it contacts the lower surface of the hold down plate 920 and is forced down against the web 811 and moved to a level where it will pass below the lower folding plate 833 as explained above.

As illustrated in FIG. 38A, the hold down plate 920 is carried at the lower end of a rigid arm having an upper end pivoted at 924 to the frame of the machine for movement between a lowered position as shown in FIG. 38A in which the hold down plate is properly positioned with respect to the web guide 837, and a raised position (not shown), the two ranges of pivotal movement being established by two stops 936, 938. A torsion spring 928 urges the arm toward its lowered position. In one embodiment, a proximity switch (not shown) is mounted adjacent the arm 923. A backed-up or jammed condition of pads 1 in the channel 922 causes an upward force on the hold down plate 920 and a corresponding movement of the arm 923 against the bias of the spring 928. This movement triggers the proximity switch, alerting operators of the jammed condition or stops the movement of transport conveyor 705.

Preferably, as shown in FIGS. 38B and 38C, the device 918 also includes a plenum member (e.g., plate 930) which overlies the hold down plate 920 and defines a plenum chamber above the plate, and an air fitting 929 on the plenum member 930 for supply of pressurized air from a suitable source to the plenum chamber. The hold down plate 920 is perforated with air holes 934 through which air is directed to form an air film between the hold down plate 920 and the pads 1 as they pass beneath the plate. The air film reduces friction between the pads and the hold down plate 920 as the pads move toward the folding boards 831, 833. Additionally, it will be understood that other devices may be used for applying the stated pressing force on the pads.

The web guide 837, opening 839 and folding members 831, 833 shown in the drawings can assume other shapes without departing from the scope of this invention. For example, the length and shape of the tongue 861 can vary. Further, the size of the opening 839 can vary, although it is preferred that the opening have a width W in the cross direction CD (transverse to the direction of web travel) about 97% of the width of each of the pads, and a length L in the machine direction MD of about 18% of the length of each pad.

The position of the forming device 805 is preferably adjustable in the machine direction MD, cross direction CD, and Z direction. While this adjustment can be achieved in various ways, one such way is illustrated in FIG. 35. In this particular embodiment, the forming device 805 is mounted on a post 909 affixed at its lower end to a channel 911 extending in the machine direction MD. The channel, in turn, is attached to a cross rail 915 which is supported by a mounting plate 917 with slots 919 fastened to the frame of the machine. The channel and rail 911, 915 are provided with fastener openings to permit adjustment of the forming device in the MD and CD directions, and the slots 919 provide for adjustment of the device in the Z direction. Thus, the position of the forming device can be adjusted in the MD, CD and Z directions, as needed.

Referring to FIG. 38, an adhesive applicator, generally designated 925, is provided at the forming device 805 for applying a suitable adhesive to at least one margin M1, M2 of the web 811 before or as it is folded to secure the tube 815 around the pads 1 after exit from the forming device 805. In one embodiment, the applicator 925 comprises a gun 927 capable of dispensing a suitable adhesive (e.g., a hot-melt glue) through a nozzle 931 positioned close to the web 811 (e.g., within 0.003 to 0.004 in.) for the transfer of adhesive to margin M1 of web as the web moves past the nozzle 931 and before the margin is overlapped with the opposite margin M2 of the web. Preferably, the nozzle transfers a continuous bead or stripe of adhesive to the web, as indicated at 933 in FIGS. 36 and 40, but it will be understood that the adhesive may be intermittently applied in the web, if desired. The adhesive dispensed from the nozzle 931 is preferably in extruded bead form, but it may also be sprayed. In one embodiment, an air supply line 932 provides a pressure source to open the gun 927 and an air supply line 934 provides a pressure source to close the gun 927.

Figure 42:
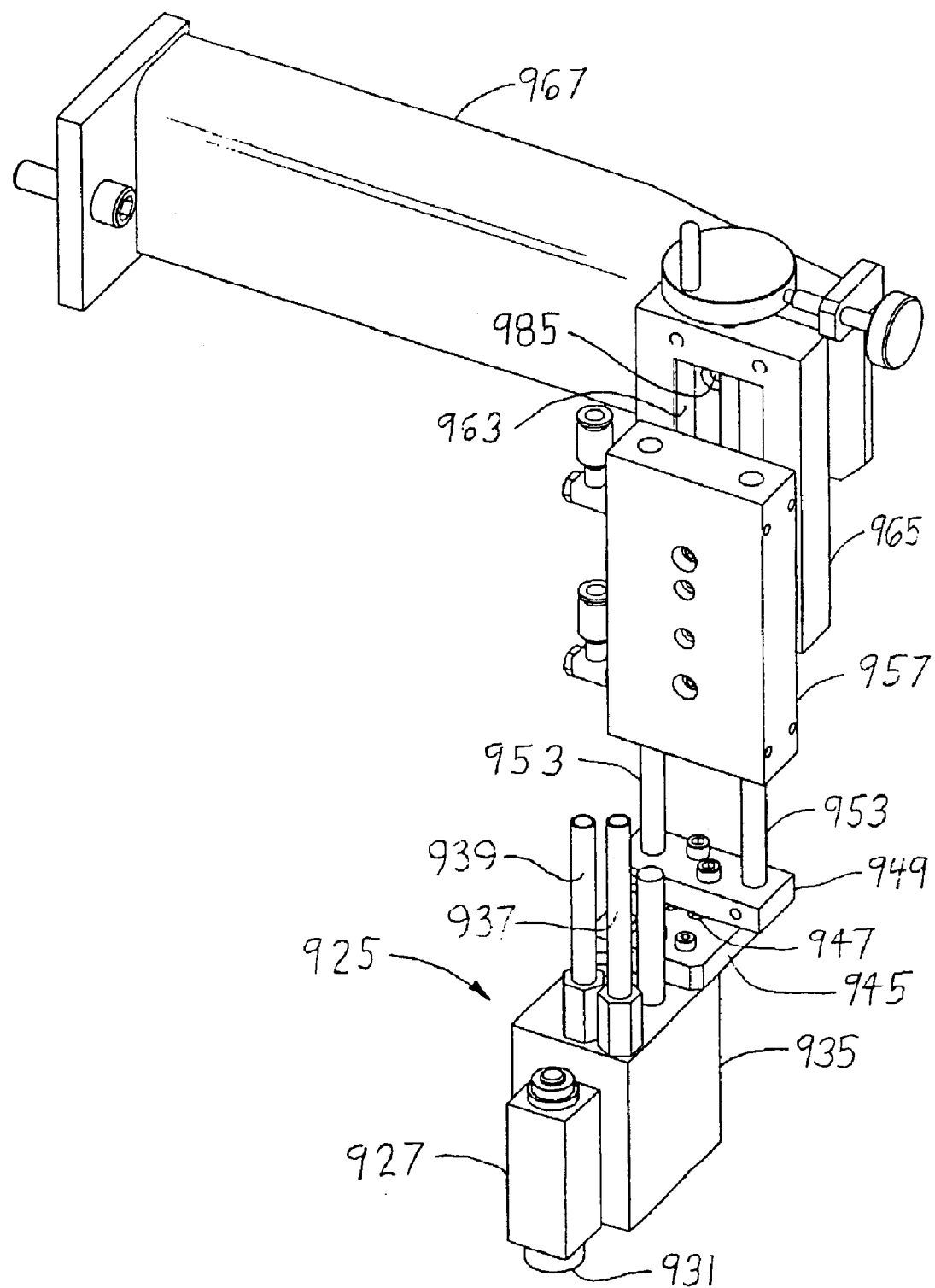
FIG. 42 is a perspective of an applicator for applying adhesive to the web as it moves over the forming device.
Figure 43:
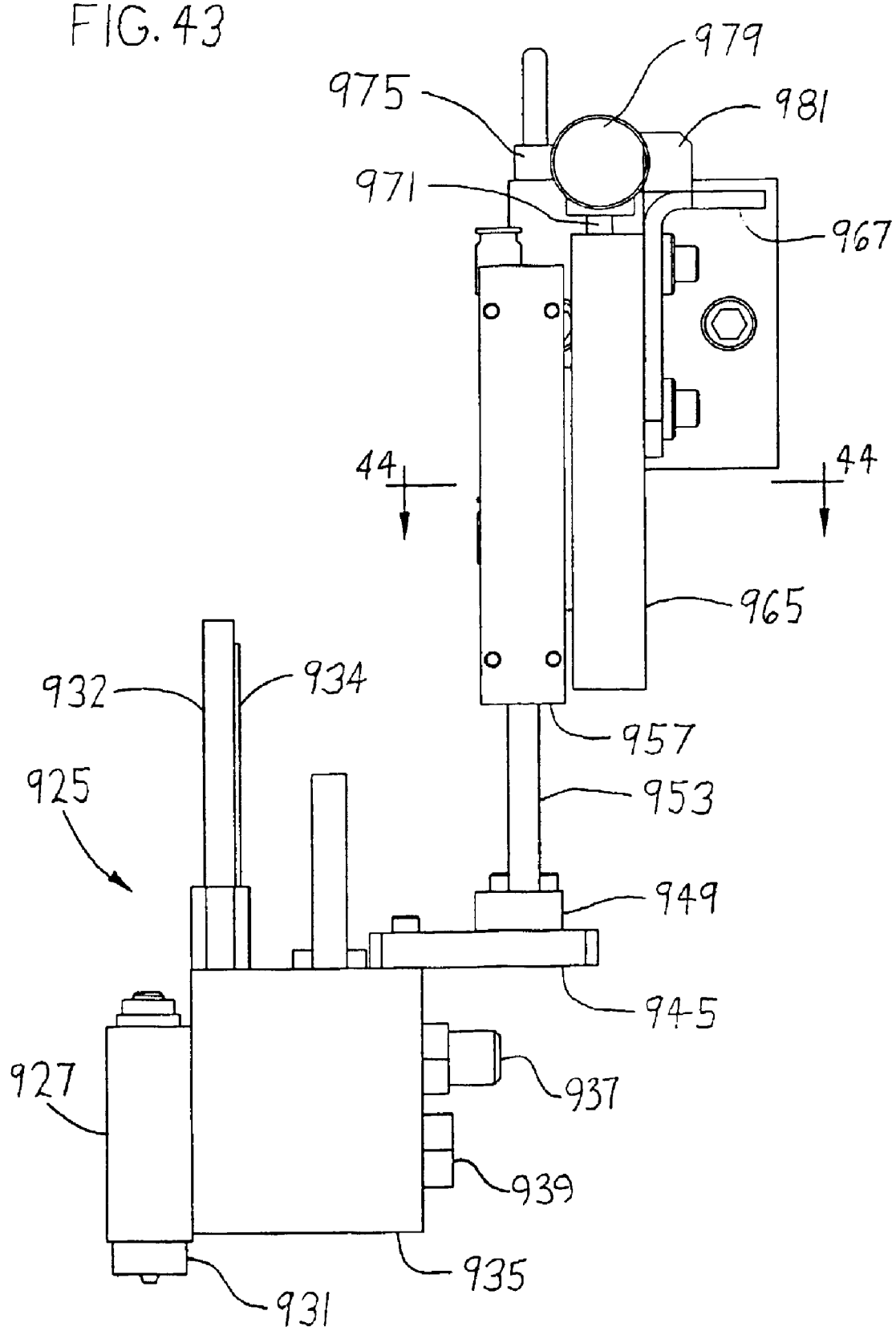
FIG. 43 is a front elevation of the applicator of FIG. 42.
Figure 44:
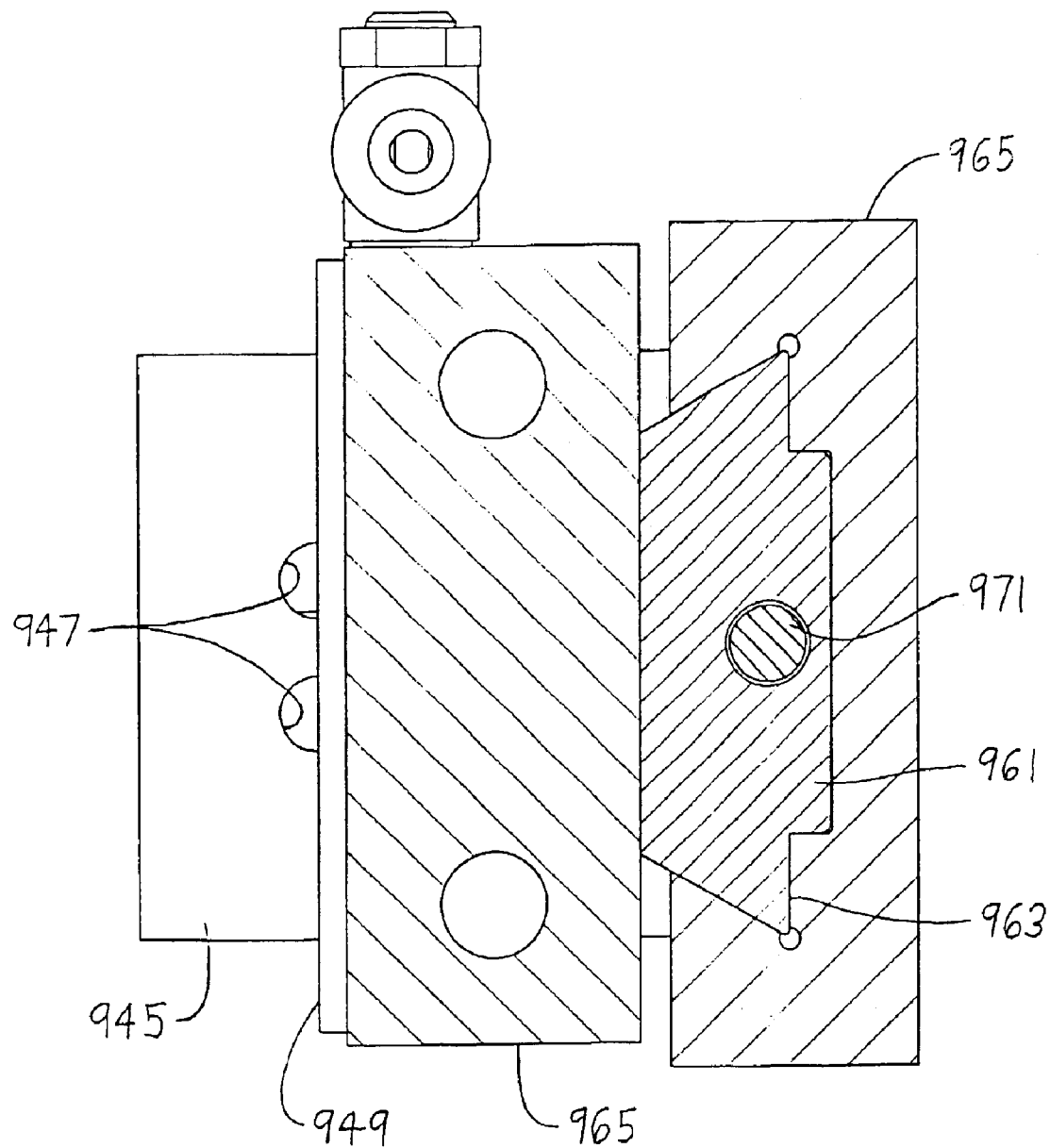
FIG. 44 is a horizontal section on line 44—44 of FIG. 43.

In the embodiment shown in FIGS. 42–44, the applicator further comprises a housing 935 connected to an adhesive supply line 937 for the delivery of adhesive to the gun and, optionally, to a pressure air line 939 (e.g., 20 psi air) for the delivery of air under pressure for dispensing of the adhesive through the nozzle 931. The position of the nozzle is adjustable in the Z direction to vary the spacing between the nozzle and the web, as needed.

FIGS. 42–44 illustrate one possible way to achieve this adjustment. In this particular embodiment, the housing 935 of the applicator is attached by means of a bracket 945 with slots 947 to a crosshead 949 bridging the piston rods 953 of a power actuator 957. The actuator, in turn, is mounted on a tongue 961 slidable in a vertical groove 963 in a mounting block 965 attached to an L-shaped bracket 967 affixed to the frame. A screw shaft 971 (FIG. 44) rotatable in the mounting block 965 extends through a threaded bore 971 in the tongue 961, the arrangement being such that rotation of the screw draft 971 by a handwheel 975 causes the tongue and actuator 957 to move in a vertical direction. Thus, the position of the adhesive applicator 925 in the Z direction can be roughly adjusted by extension and retraction of the piston rod 953, and more finely adjusted by rotation of the handwheel 975.

When the spacing between the nozzle 931 and the web 811 is set, a thumbscrew 979 threaded through a bar 981 affixed to the bracket 967 is tightened against the handwheel 975 to lock the screw shaft 971 against rotation until a further adjustment is needed. The bracket 967 holding the mounting block 965 has horizontal slots 985 (FIG. 42) to enable the position of the nozzle 931 to be varied in the CD direction extending transversely of the web. Adjustment in the MD direction is effected by means of slots 947. Other mechanisms can be used to provide for adjustment of the position of the applicator 925 relative to the web 811.

Alternatively, the adhesive gun 927 can be positioned for dispensing adhesive for application to the opposite margin M2 of the web after it has been folded over to a position overlying the pads but before margin M1 has been folded face-to-face with M2. A notch (not shown) may be provided in the lower folding board 833 for this purpose. A portion of this notch extends upstream from the angled folding edge 831A of the upper folding board 831, leaving the folded-over margin M2 of the web exposed for application of an adhesive from the gun 927. After the adhesive is applied, the upper folding board 831 folds the other margin M1 of the web over the underlying margin M2 as the web is pulled past the folding boards.

The web-pulling means 807 for pulling the web 811 past the forming device 805 comprises, in one embodiment (FIGS. 35 and 45), a vacuum conveyor, generally designated 1001, in the form of an endless perforated belt 1003 (the perforations being omitted in FIG. 45 for simplicity) trained around upstream and downstream rollers 1007, 1009, at least one of which (e.g., roller 1007) is rotated by a drive shaft 1011 mounted in a bearing housing 1013 secured to a bracket 1015 on the frame. A vacuum box or manifold 1019 is supported on the frame below the upper reach of the belt 1003 and has openings 1021 in its upper surface for drawing a vacuum through the belt to grip the tubular wrapper 815 formed by the forming device 805, thus providing the force necessary for pulling the web 811 in the machine direction MD over the forming device and for feeding the tubular wrapper containing the pads to a wrapper sealing station 1025 downstream from the forming device 805.

Figure 45:
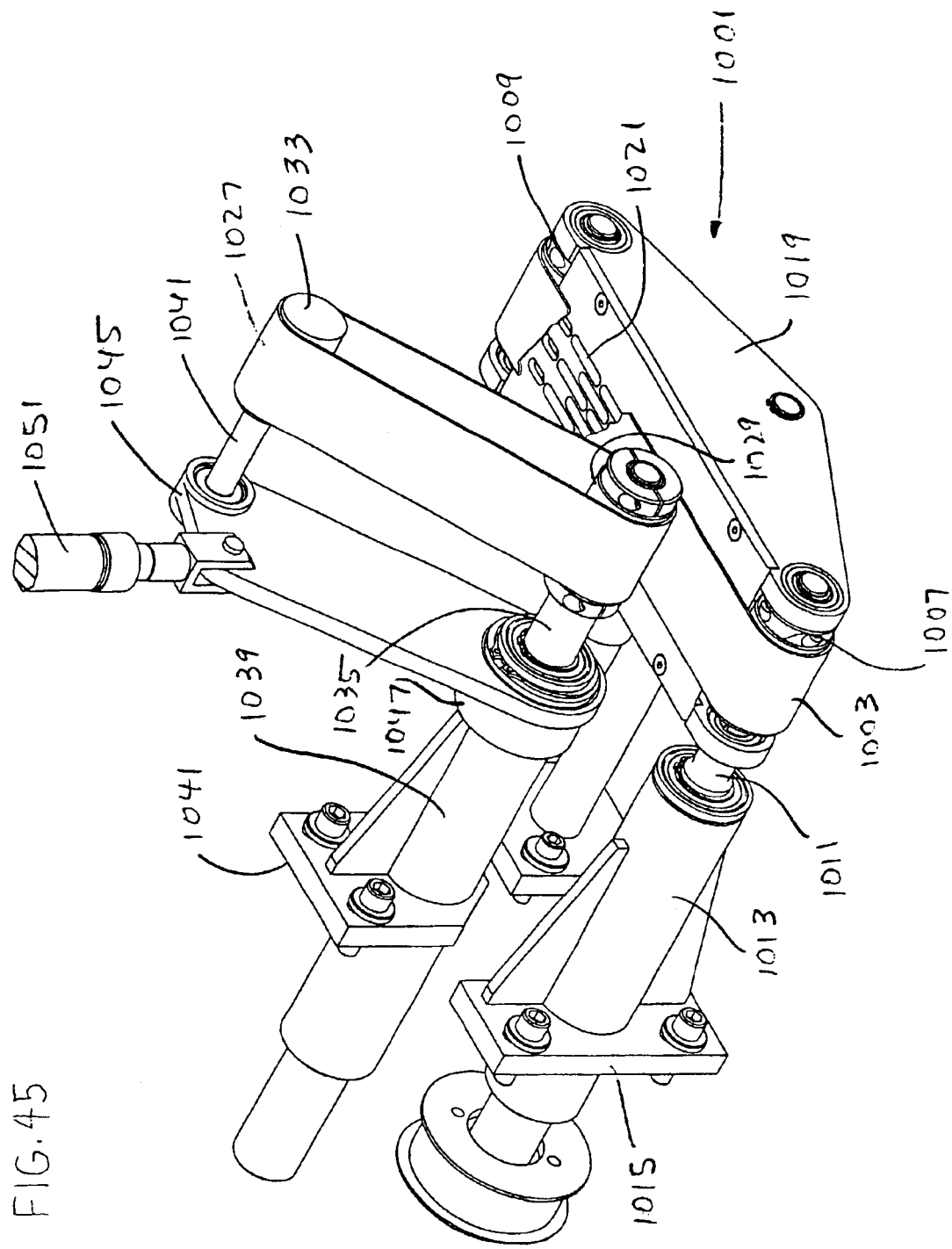
FIG. 45 is a perspective of a conveyor for conveying wrapped pads from the forming device to the sealing rolls, the conveyor being shown in a raised position.

The conveyor 1001 also includes an upper endless compression belt 1027 supported by upstream and downstream rollers 1029 and 1033, respectively. As shown in FIG. 45, the upstream roller 1029 is driven by a shaft 1035 rotatable in a bearing housing 1039 affixed to a bracket 1041 fastened to the frame of the machine. The downstream roller 1033 is supported by a shaft 1041 journalled in a bearing plate 1045 having a pivot connection 1047 with the bearing housing 1039. The bearing plate 1045 is pivotable about the connection by means of a power actuator (e.g., cylinder 1051) to move the compression belt 1027 between a lowered position in which the lower reach of the belt is substantially parallel or having a small decline with respect to the upper reach of the lower belt 1003, as shown in FIG. 35, and a raised position as shown in FIG. 45. When in its lowered position, the compression belt 1027 applies a compressive force to the tubular wrapper 815 to press the overlapping margins M1, M2 of the wrapper together to form a good adhesive seal along the tube, and also to assist in the feed of the wrapper in the machine direction MD. The compression belt 1027 can be raised when not in use, as for maintenance.

Figure 46:
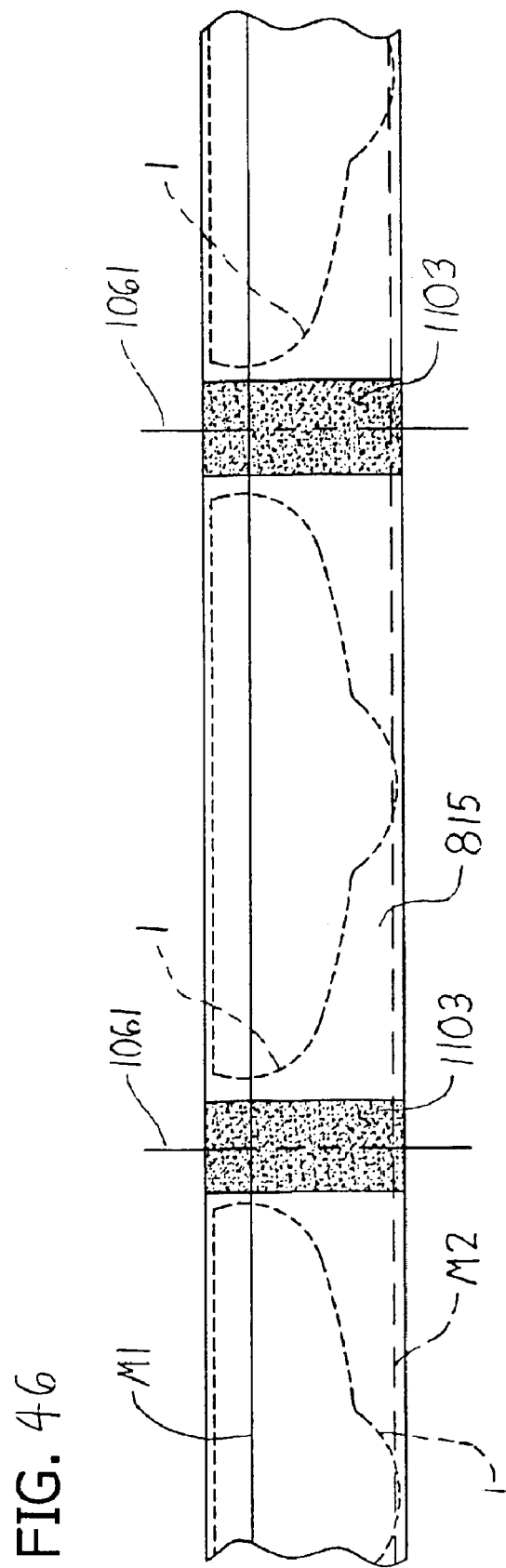
FIG. 46 is a schematic plan view of a series of pads wrapped in a tubular wrapper.
Figure 47:
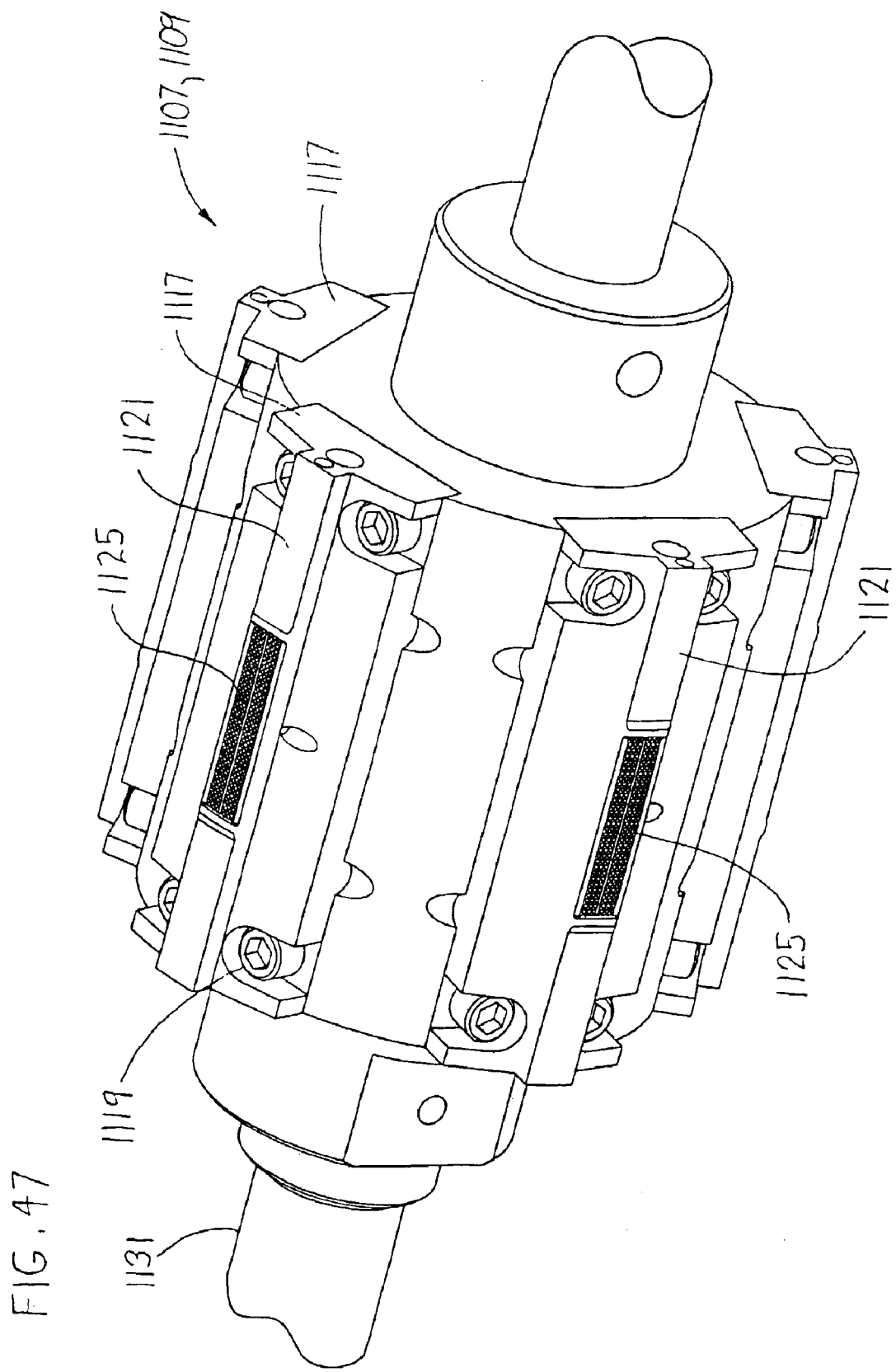
FIG. 47 is a perspective of a sealing roll.

Sealing apparatus, generally designated 1100 in FIG. 35, is provided at the sealing station 1025 for sealing the tubular wrapper 815 between the pads 1 in seal areas 1103 extending transversely with respect to the tube 815 in the CD direction (see FIG. 46). Referring now to FIGS. 35 and 47, the sealing apparatus 1100 comprises upper and lower sealing rolls indicated at 1107 and 1109, respectively, each of which carries a plurality of sealing jaws 1113 extending axially along the circumference of the roll at spaced intervals around the roll (e.g., six sealing jaws at 60° intervals around the roll). Each jaw 1113 comprises a base 1117 fastened to the roll in conventional fashion, as by threaded fasteners 1119, and a sealing bar 1121 projecting out from the base having a heated sealing area 1125.

A heating element (not shown) is embedded in the bar for heating the sealing area 1125 of the bar to a temperature sufficient to soften the wrapper material. The rolls 1107, 1109 are driven by suitable drive mechanisms 1131 to rotate in timed and synchronized relation to one another so that the heated sealing jaws 1113 on the two rolls sequentially move into registration with one another and simultaneously contact opposing (e.g., upper and lower) surfaces of the tubular wrapper 815 at intervals spaced along the web to press the surfaces together and form the seal area 1103 between the pads, as will be understood by those skilled in this field. The operation of the heating elements is controlled by temperature sensors embedded in the sealing bars 1121 adjacent the heating elements. Preferably, the sealing areas 1125 of the sealing bars 1121 are textured (e.g., roughened) to mechanically deform the opposing surfaces of the tubular wrapper 815 and thus establish a mechanical bond between the surfaces to hold them together prior to complete cooling of the seal. A supporting surface 1131 is provided immediately upstream of the sealing rolls 1107, 1109 for supporting the tubular wrapper as it enters the nip of the rolls.

The tubular wrapper 815 is pulled between the two sealing rolls 1107, 1109 by suitable means, such as a pair of upper and lower endless belts 1135, 1137 similar to the endless belts 1003, 1027 previously described immediately upstream from the sealing station 1025. These belts 1135, 1137 may also function to feed the sealed wrapper 815 to a cutting station 1041 where cutting apparatus 1043 is provided for cutting the sealed tubular wrapper at the seal areas 1103 to form individual wrapped pads.

Referring to FIG. 29, the cutting apparatus 1043 comprises, in one embodiment, a pair of upper and lower cutting rolls designated 1051 and 1053, respectively. The construction of these rolls is similar to that of the sealing rolls 1107, 1109, except that the sealing jaws on one roll are replaced by cutting blades and the sealing jaws on the other roll are replaced by anvil bars which support the web for cutting by the blades, in a conventional manner. Rotation of the cutting rolls 1051, 1053 is timed and synchronized to cut through the tubular wrapper 815 at the seal area 1103. As shown schematically in FIG. 46, the cut 1061 across each seal area is generally at the middle of the seal (in the machine direction MD) so that one cut simultaneously forms the trailing seal of one wrapper and the leading seal of the following wrapper. The individually wrapped pads are then discharged into a suitable receptacle 1065 (FIG. 16) or onto a conveyor for transport to an optional collating station where the pads may be grouped by hand or by a suitable collating mechanism for further packaging in cartons or the like.

The operation of the apparatus described above to carry out the methods of the invention will now be described. Raw fibers (e.g., cotton and rayon) are weighed out and mixed in the desired proportion in the fiber blending section 21 of the system. This process is initiated by loading fibers of one material (e.g., cotton) on the in-feed conveyor 67 of the first weighing apparatus 41 (see FIG. 7) for delivery to its respective weigher 77, and by loading fibers of another material (e.g., rayon) on the in-feed conveyor of the second weighing apparatus 43 for delivery to its respective weigher. The weighers 77 are operable to weigh out quantities of these fibers in correct proportion by weight (e.g., 1120 grams of cotton and 480 grams of rayon) and to unload them onto the conveyor 91 for delivery to the blend opener 47.

In one embodiment, the unloading is timed so that the downstream weigher 77 unloads its weighed-out batch of fibers directly on top of the batch unloaded by the upstream weigher 77, so that a single pile of fibers containing the correct proportions of fibers is delivered to the blend opener 47 (see FIG. 8). Fibers fed into the blend opener are opened and mixed, to some extent, and then transported through air duct 49 to the air separator 51 (FIG. 9). There, the air and fiber fines are separated from the longer fibers and delivered to the fines collector 57. The longer fibers are conveyed to the rotary air lock 144 which rotates at the necessary speed to feed the longer fibers to the inlet of the fine opener 55 at the desired rate. The fine opener 55 (FIG. 10) further separates and mixes the fibers and delivers them to the feed chute 221 via the air duct 61.

The fibers entering the inlet section 229 of the feed chute 221 (FIG. 11) are entrained in a stream of air and directed into the upper chute 231 where they collect above the feed and beater rolls 245, 247. Air entering the upper chute 231 exits through the porous wall 237 of the chute. The feed and beater rolls 245, 247 rotate to perform a separation and blending operation on the fibers before they are delivered to the accumulation chute 263 in a substantially separated ("opened") and mixed condition, with the fibers of one type being blended with the fibers of the other type. The feed of the fibers down in the accumulation chute 263 is assisted by the oscillation of the shaker plate 267. Further, the frequency and amplitude of the oscillation can be varied to control the density of the fibers delivered to the compression rolls 291 adjacent the outlet 227 of the feed chute.

As the fibers pass between these two rolls 291, they are formed into a layer 295 of desired thickness for deposit on the transfer device 301 leading to the forming section 27 of the machine (FIG. 13). The thickness of the layer 295 and the speed at which it is delivered is controlled by the size of the gap 293 between the compression rolls 291 and the speed of the rolls, respectively. For example, the layer 295 may have a thickness of about 2 in. and the rolls may have a surface speed of about 6 fpm. The density of the layer 295 (e.g., weight per unit length) is controlled at least in part by the height of the column of fibers in the accumulation chute 263, the amplitude and frequency of the oscillation of the shaker plate 267, the compressive force applied by the compression rolls 291, and the speed of the rolls 291. Preferably, the density of the fibers discharged from the feed chute 221 is in the range of 0.005–0.16 g/cc, more preferably in the range of 0.010–0.030 g/cc, and even more preferably in the range of 0.013–0.019 g/cc. The layer 295 of blended fibers delivered from the feed chute 221 may be relatively wide, e.g., 40 in. wide, although this dimension may vary considerably. If sufficiently compacted, the layer 295 may be in the form of an integral web capable of independently maintaining its body and shape. However, the layer may also be a thickness of loosely compacted (or non-compacted) fibers combining to form a body the shape of which is not self-sustaining.

The layer 295 of fibers from the feed chute 221 gravitates down the slide 301 (or is conveyed in some other manner, as by an endless conveyor) for delivery to the gap 319 between the feed roll 315 and the adjacent guide surface 317, as shown in FIG. 14. The rotating feed roll 315 serves to feed the layer 295 of blended fibers to the fiberizing roll (e.g., lickerin roll 321) which breaks up the fibers. After this fiberizing operation, the fibers fall and are swept into the inlet of the air chamber 347 where they are air laid onto the forming surface 337 of the conveyor 335 and reformed into a layer 343 having a width generally corresponding to the final width of the absorbent body in the pad (e.g., body 5 in pad 1). As noted previously, the fibers making up this reformed layer 343 are randomly oriented and blended into a substantially homogenous mixture having strength in MD and CD directions, and further having the ability to effectively absorb and distribute fluid deposited on the material. The thickness of the reformed layer 343 is controlled by the speed of the reforming conveyor 335, which is variable, and by the amount of fibers delivered into the air chamber 347 for deposit on the foraminous forming surface 337 of the conveyor.

As thus reformed, the layer 343 is transported to the compression belt 401 where the fibers are lightly compressed, and then to the compression rolls 407, 409 where the fibers are more severely compressed into the aforementioned continuous web 417 of absorbent material having a thickness generally corresponding to the thickness of the absorbent body (e.g., body 5) in the final product (FIG. 17). The compression belt 401 may be eliminated, if not needed. The thickness of the web 417 is controlled primarily by the spacing between the two compression rolls 407, 409. Following compression, the web is conveyed to the pad-making section 31 of the system.

At the pad-making section (FIG. 18), the web 417 is fed in the machine direction MD between the two cutting rolls 451, 453 at the first cutting station 431, where the web is cut to form individual absorbent bodies 5, an exemplary shape of which is illustrated in FIG. 20. The web is then vacuum conveyed by the knife roll 451 to the first transfer nip TN1 where the absorbent bodies are transferred to the first transfer cylinder 485, while maintaining the bodies in precise position relative to one another. The trim (waste material) 491 from the cutting operation is preferably removed after the transfer by means of the vacuum duct 493 for delivery of the trim to a suitable collector, not shown. Meanwhile, the absorbent bodies 5 are vacuum conveyed by the first transfer cylinder 485 to the second transfer nip TN2.

The cover web 7W is also fed from the unwind roll 425 to the second transfer nip TN2, where bodies 5 are successively transferred from the first transfer cylinder 485 to positions on the cover web overlying respective pockets 553 in the sealing roll 541. The bodies 5 and underlying web 7W are drawn by the vacuum openings 561 into the pockets 553 and held in place as they are conveyed to the sealing nip SN. If a baffle web 9W is used, it is combined with the cover web 7W and absorbent bodies 5 at the sealing nip SN, as described previously (FIG. 19), and the sealed laminated web 437 is then vacuum conveyed to the third transfer nip TN3 where it is transferred to the second transfer cylinder 571. The second transfer cylinder 571 vacuum grips the laminated web and conveys it to the fourth transfer nip TN4 where the web 437 is transferred to the lower cutting roll 607 for vacuum conveyance of the web to the second cutting nip CN2 at the second cutting station 441. There, the two cutting rolls 607, 609 cut the laminated web 437 around the absorbent bodies 5 to form individual pads (e.g., pads 1) which are held by the vacuum openings 617 in the lower roll 607 as the web is conveyed to the fifth transfer nip TN5. The pads 1 are transferred at TN5 to the third transfer cylinder 615, which conveys the pads and deposits them on the 3-belt vacuum conveyor 641 in an orientation where the pads preferably lie flat on the conveyor with the baffle layer 9 of the pad facing up (if a baffle layer is used), with the central section of the pad supported by the center belt 643, and with the side sections 1A, 1B of the pad supported by the side belts 645. The trim or waste portion of the web (indicated at 625 in FIG. 28) is removed by allowing the trim to follow around the third transfer cylinder 615 for delivery to a suitable collector, or by pulling it straight down from the fifth transfer nip TN5 for disposal.

Figure 34:
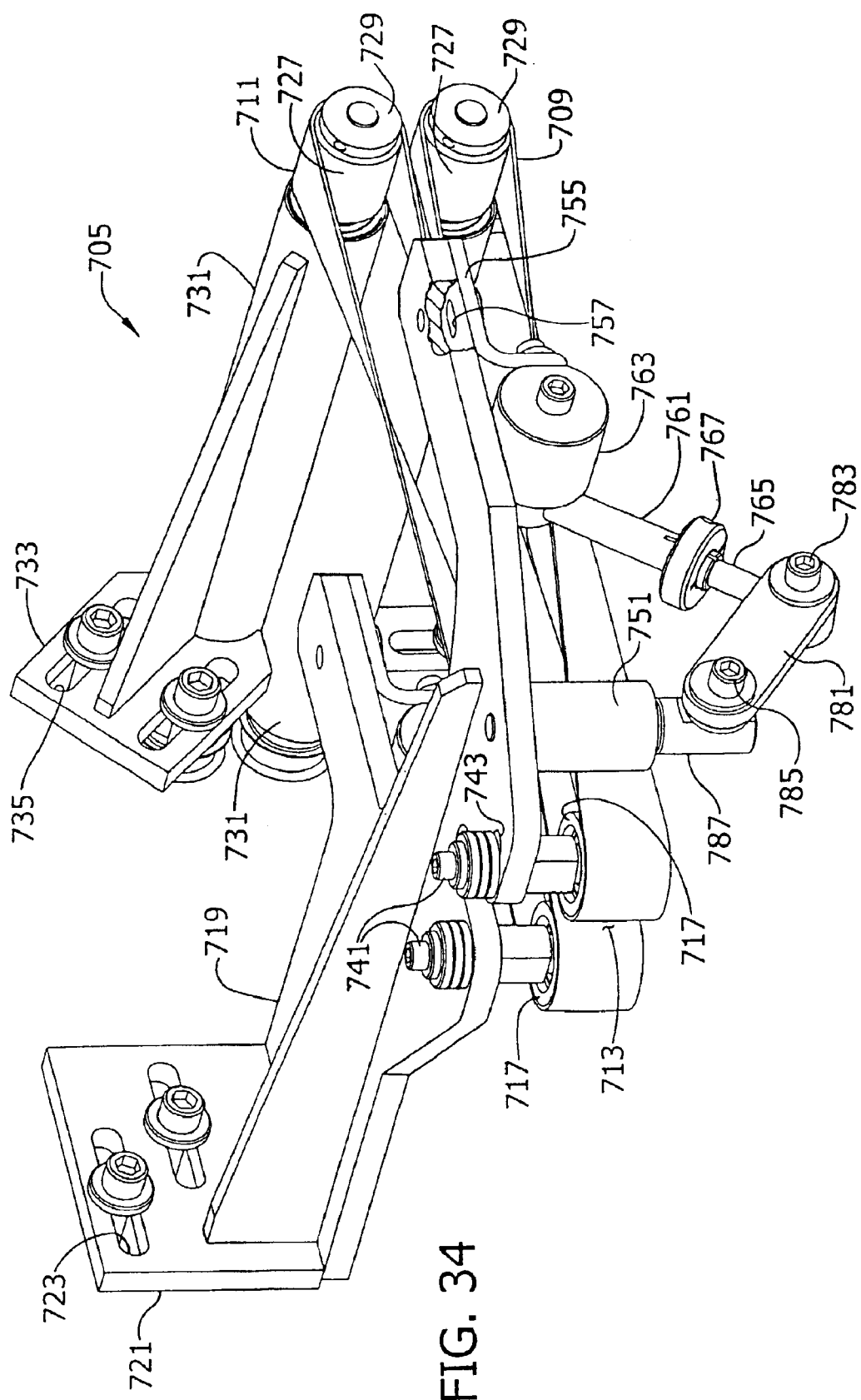
FIG. 34 is a perspective of a conveyor for transporting pads from the folding section to the packaging section.

The vacuum conveyor 641 conveys the pads 1 to the folding section 33 while maintaining the pads in fixed positions relative to one another. At the folding section (FIG. 30) the side sections 1A, 1B of each pad are folded up by the two folding disks 671 while the center section of the pad is held down by the hold-down disk 663. As thus folded, the pad appears as shown in FIG. 3, with the pad preferably lying in a generally upright (e.g., vertical) orientation. Prior to folding, an adhesive such as a hot-melt glue may be applied to the upper surface of the pad (e.g., the baffle layer 9) by the applicator 687, so that when the two side sections 1A, 1B are folded face to face, the adhesive will secure the pad in its folded condition. After each pad 1 is folded, and while it is still being held upright by the folding disks 663, it is fed into the gap 713 between the transport belts 709, 711 for conveyance to the packaging section 35 (FIG. 34). The 90° twist in the belts 709, 711 functions to rotate the pads 1 to a generally horizontal orientation for delivery to the forming device 805. The position of the guide rolls 751 can be adjusted, if necessary, to maintain the twist belts properly centered on the vertical rollers 717 at the upstream ends of the belts.

At the packaging section 35, the web 811 of flexible wrapping material is pulled over the forming device 805 by the web-pulling means 807, with the web first advancing over the web guide 837 and then past the folding boards 831, 833 (see FIGS. 36 and 38). As the web 811 is pulled over the forming device, pads 1 are fed from the transport belts 709, 711, one at a time, into the gap 901 between the tongue 861 of the web guide and the overhead belt 875, the latter moving at the same speed as the web. As each pad enters this gap, it is conveyed with the web in the machine direction MD over the opening 839 between the tongue 861 and the folding boards 831, 833. As the pad moves over the opening 839, the downwardly inclined lower reach of the belt 875 applies a force on the pad 1 to press it into the central portion of the web 811, causing the web to cup and, preferably, to stretch somewhat in the cross direction CD, as best illustrated in FIG. 39. This cupping of the web creates a volume in the web, i.e., a depression or groove or pouch 905, to begin the formation of the tubular wrapper 815 around the pad. The force applied to the pad 1 is sufficient to cause the web 811 and underlying central portion of the web to move down to a position where the top of the pad will clear the lower folding board 833. This position can be adjusted by operation of the power cylinder 895 to pivot the belt 879 up or down relative to the folding device 805. As noted previously, other force-applying devices (e.g., an inclined stationary surface) can be used to initiate the formation of the tubular wrapper 815 around the pads.

Figure 40:
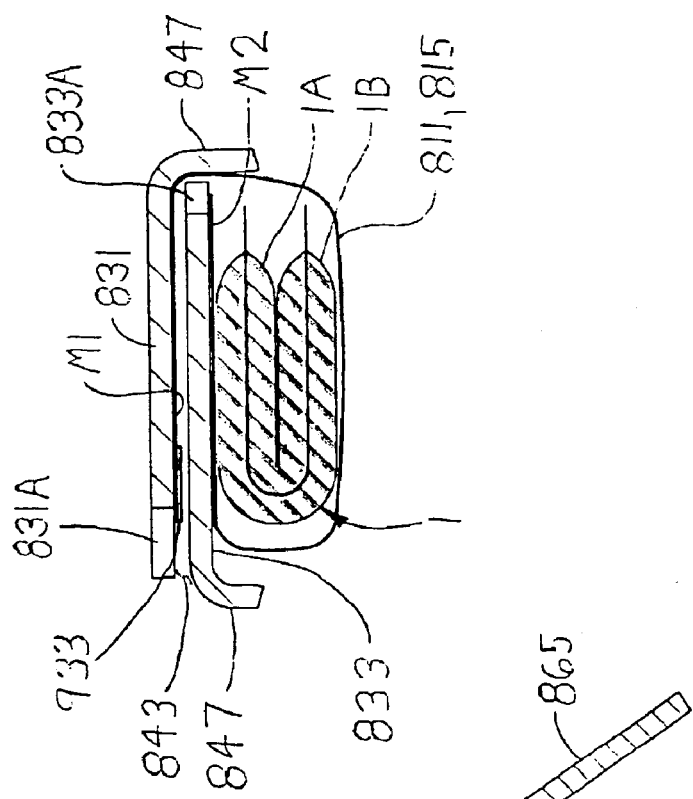
FIG. 40 is a vertical section taken on line 40—40 of FIG. 38.

As the pad 1 and central portion of the web 811 move below the lower folding board 833, the side margins M1, M2 of the web engage respective folding edges 831A, 833A of the folding boards and are folded into face to face relation, as shown in FIG. 40, to form the tubular wrapper 815 around the pad. In the embodiment shown in FIG. 40, the side margins M1, M2 of the web are folded so that the facing surfaces of the margins are constituted by opposite faces of the web 811 to form a so-called overlap seam on the tube 815. However, it will be understood that the side margins M1, M2 could be folded to make a fin seam where the facing surfaces of the margins are constituted by the same face of the web 811. In either event, adhesive 933 is applied to at least one of the side margins M1, M2 by the applicator 925 before the margins are folded into face to face relation, the adhesive being on the surface of the side margin which will eventually face the opposing side margin after the folding operation is complete. The spacing between the nozzle 931 of the applicator 925 and the surface of the web 811 to which the adhesive is applied is preferably such that the web draws a continuous bead of uniform volume (or a series of intermittent spots of uniform volume) from the nozzle as the web passes the nozzle. Alternatively, the adhesive may be sprayed or otherwise applied to the web 811.

The tubular wrapper 815 containing the pads 1 is pulled in the machine direction MD by the vacuum belt 1003 (FIG. 45), which in the preferred embodiment provides the primary force for pulling the web 811 over the forming device 805. As the newly-formed tubular wrapper 815 passes between the vacuum belt 1003 and the overhead compression belt 1027, it is subjected to a compressive force to adhere the side margins M1, M2 of the web together to form a longitudinal seam extending the length of the tubular wrapper before the tube is fed between the two sealing rolls 1107, 1109 at the sealing station 1025. As the two sealing rolls rotate, the sealing bars 1121 on the upper roll 1107 move into sequential registration with the sealing bars 1121 on the lower roll 1109 to seal the tube in the seal areas 1103 between the pads (see FIG. 46). The tubular wrapper tube containing the pads is pulled through the sealing station 1025 by the vacuum belt 1137 and compression belt 1135 downstream from the sealing station. These belts also serve to feed the sealed tube to the cutting station 1041 where the cutting rolls 1051, 1053 cut across the tube at the sealed areas 1103 to form individually wrapped pads. As noted previously, further packaging operations can be performed, if desired.

For efficiency, the various sections of the apparatus of the invention should be run at compatible speeds which enable substantially continuous operation (at least 85% of the time) of all sections without interruption. That is, upstream sections should not be run at excessively high speeds which will exceed the capacity of downstream sections, nor at excessively slow speeds which will starve the downstream sections.

While the apparatus and methods have been described in the context of making interlabial pads of the type shown in FIG. 1, the features of the invention can be used to make other types of articles, absorbent or otherwise.

When introducing elements of the invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. An apparatus for wrapping pads, said apparatus comprising:
    a forming device over which a web of flexible wrapping material is adapted to be pulled in tension, said forming device comprising:
        first and second folding members having angled folding edges adapted for contact by respective opposite side margins of the web as the web is pulled past the folding edges;
        a web guide for guiding the web toward the folding edges;
        an opening between the web guide and the folding edges adapted to be spanned by a central portion of the web as the web is pulled past the forming device;
    a device for placing a series of pads, one after another, on the web as it is pulled past the forming device so that the pads move with the web over the opening and past the folding edges of the forming device; and
    a device for applying a force to the pads to force the pads against the central portion of the web as the pads move across said opening, said force being sufficient to cup the web to position the pads for travel past the first and second folding members with concurrent folding of the side margins of the web by respective folding edges to form a tube around the pads.

2. The apparatus as set forth in claim 1 further comprising apparatus for sealing and cutting said tube to form individual wrappers for the pads.

3. The apparatus as set forth in claim 1 wherein said force applied to the pads is sufficient to stretch the web to effect a tight wrap of the web around the pads as the tube is formed.

4. The apparatus as set forth in claim 1 wherein said force-applying device comprises an inclined surface adapted for contact by said pads to force the pads into the central portion of the web.

5. The apparatus as set forth in claim 4 wherein said inclined surface has one or more air holes therein for directing air from an air source to establish an air film between the surface and the pads.

6. The apparatus as set forth in claim 1 wherein said force-applying device is movable in the direction of web travel to exert a pushing force against the pads in the direction of web travel.

7. The apparatus as set forth in claim 6 wherein said force-applying device comprises an inclined surface adapted for contact by said pads to force the pads into the central portion of the web.

8. The apparatus as set forth in claim 6 wherein said force-applying device comprises an endless belt having an inclined reach positioned for contact by said pads.

9. The apparatus as set forth in claim 1 wherein said pads are resiliently compressible, and wherein said force applied to the pads is sufficient to resiliently compress the pads.

10. The apparatus as set forth in claim 9 wherein said force is sufficient to compress the pads to have a compressed thickness in the range of 50–99% of an uncompressed thickness of the pad.

11. The apparatus as set forth in claim 1 wherein said folding members comprises upper and lower folding plates having spaced apart generally parallel opposing surfaces defining a relatively narrow gap extending in the direction of web travel as the web is pulled past the forming device, said gap being adapted to receive said at least one side margin of the web as the web is folded to form said tube.

12. The apparatus as set forth in claim 1 wherein said web guide comprises a wall adapted for contact by said web, said wall being angled relative to the plane of said opening and having a base edge and side edges tapering to an apex, and a tongue extending from the apex toward said opening.

13. The apparatus as set forth in claim 12 further comprising a pair of notches in said wall extending from said apex toward said base edge on opposite sides of the tongue, portions of said web deforming into said notches as the web is pulled over the wall and said tongue.

14. The apparatus as set forth in claim 1 wherein said web guide and folding members are formed as a single piece of bent sheet metal.

15. The apparatus as set forth in claim 1 wherein said folding members are adapted to fold said opposite side margins into face to face overlapping relation, and wherein said wrapping apparatus further comprises an adhesive applicator for applying adhesive to one of said web side margins to form an adhesive bond between the side margins when they are overlapped.

16. The apparatus as set forth in claim 15 wherein said adhesive applicator is operable to apply adhesive to one side margin at a location upstream from said folding edges.

17. The apparatus as set forth in claim 1 wherein said pads are interlabial pads.

18. A method of wrapping pads, said method comprising:
    pulling a web of flexible wrapping material past a forming device having folding edges adapted for contact by respective opposite side margins of the web as the web is pulled past the folding edges, a web guide for guiding the web toward the folding edges, and an opening between the web guide and the folding edges adapted to be spanned by a central portion of the web as the web is pulled past the forming device;
    placing a series of pads, one after another, on the web as the web is pulled so that the pads move with the web across the opening and past the folding edges of the forming device; and applying a force to the pads to force them against the central portion of the web as the pads move across said opening, said force being sufficient to cup the web to position the pads and central portion of the web for travel past the first and second folding members with concurrent folding of the side margins of the web by respective folding edges to form a tube around the pads.

19. The method as set forth in claim 18 further comprising sealing and cutting the tube to form individual wrappers for the pads.

20. The method as set forth in claim 18 wherein said tube is formed around each pad so that opposite side margins of the web overlap one another.

21. The method as set forth in claim 18 wherein said forcing step comprises moving the pads against a surface inclined in the direction of web travel to force the pads against the web.

22. The method as set forth in claim 21 wherein said forcing step further comprises establishing an air film between said inclined surface and the pads.

23. The method as set forth in claim 18 wherein said force applied to each pad is sufficient to resiliently stretch the web to effect a tight wrap of the web around the pad as the tube is formed.

24. The method as set forth in claim 18 wherein said pads are resiliently compressible, and wherein said force is sufficient to resiliently compress the pads.

25. The method as set forth in claim 24 wherein said force is sufficient to compress the pads to have a compressed thickness in the range of 50–99% of an uncompressed thickness of the pad.

26. The method as set forth in claim 18 wherein said folding members fold said opposite side margins into face-to-face overlapping relation, and wherein said method further comprises applying an adhesive to one of said web side margins to form an adhesive bond between the side margins when they are overlapped.

27. The method as set forth in claim 26 further comprising applying said adhesive to said one web side margin at a location upstream from said folding edges.

28. An apparatus for wrapping pads, said apparatus comprising:
    means for pulling a web of flexible wrapping material past a forming device having folding edges adapted for contact by respective opposite side margins of the web as the web is pulled past the folding edges, a web guide for guiding the web toward the folding edges, and an opening between the web guide and the folding edges adapted to be spanned by a central portion of the web as the web is pulled past the forming device;
    means for placing a series of pads, one after another, on the web as the web is pulled so that the pads move with the web across the opening and past the folding edges of the forming device; and
    means for applying a force to the pads to force them against the central portion of the web as the pads move across said opening, said force being sufficient to cup the web to position the pads and central portion of the web for travel past the first and second folding members with concurrent folding of the side margins of the web by respective folding edges to form a tube around the pads.

29. An interlabial pad wrapped using the method of claim 18.

* * * * *